(12) United States Patent
Jiao et al.

US007968094B2

(10) Patent No.: US 7,968,094 B2
(45) Date of Patent: Jun. 28, 2011

(54) USE OF ANTI-TISSUE FACTOR ANTIBODIES FOR TREATING THROMBOSES

(75) Inventors: Jin-An Jiao, Fort Lauderdale, FL (US); Hing C. Wong, Fort Lauderdale, FL (US); Esperanza Liliana Nieves, Newark, DE (US); Luis A. Mosquera, Miami, FL (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/184,205

(22) Filed: Jul. 31, 2008

(65) Prior Publication Data
US 2009/0092602 A1    Apr. 9, 2009

Related U.S. Application Data

(60) Division of application No. 10/310,113, filed on Dec. 4, 2002, now abandoned, which is a continuation-in-part of application No. 09/990,586, filed on Nov. 21, 2001, now abandoned.

(60) Provisional application No. 60/343,306, filed on Oct. 29, 2001.

(51) Int. Cl.
*A61K 39/395*    (2006.01)

(52) U.S. Cl. ............... 424/146.1; 424/133.1; 424/141.1; 424/143.1; 514/13.7; 514/14.3

(58) Field of Classification Search .................... None
See application file for complete search history.

(56) References Cited

U.S. PATENT DOCUMENTS

| | | | |
|---|---|---|---|
| 4,644,055 A | 2/1987 | Kettner et al. |
| 4,816,567 A | 3/1989 | Cabilly et al. |
| 5,122,458 A | 6/1992 | Post et al. |
| 5,168,062 A | 12/1992 | Stinski |
| 5,171,662 A | 12/1992 | Sharma |
| 5,216,132 A | 6/1993 | Basi |
| 5,223,427 A | 6/1993 | Edgington et al. |
| 5,225,539 A | 7/1993 | Winter |
| 5,385,839 A | 1/1995 | Stinski |
| 5,437,864 A | 8/1995 | Edgington et al. |
| 5,530,101 A | 6/1996 | Queen et al. |
| 5,534,254 A | 7/1996 | Huston et al. |
| 5,552,300 A | 9/1996 | Makrides et al. |
| 5,589,173 A | 12/1996 | O'Brien et al. |
| 5,639,641 A | 6/1997 | Pedersen et al. |
| 5,693,762 A | 12/1997 | Queen et al. |
| 5,766,886 A | 6/1998 | Studnicka et al. |
| 5,861,267 A | 1/1999 | Su |
| 5,869,046 A | 2/1999 | Presta et al. |
| 5,879,677 A | 3/1999 | del Zoppo |
| 5,889,157 A | 3/1999 | Pastan et al. |
| 5,958,713 A | 9/1999 | Thastrup et al. |
| 5,985,279 A | 11/1999 | Waldmann et al. |
| 5,986,065 A | 11/1999 | Wong et al. |
| 5,997,867 A | 12/1999 | Waldmann et al. |
| 6,001,978 A | 12/1999 | Edgington et al. |
| 6,054,297 A | 4/2000 | Carter et al. |
| 6,117,639 A | 9/2000 | Germann et al. |
| 6,245,884 B1 | 6/2001 | Hook |
| 6,274,142 B1 | 8/2001 | O'Brien et al. |
| 6,287,366 B1 | 9/2001 | Derive et al. |
| 6,309,636 B1 | 10/2001 | do Couto et al. |
| 6,331,415 B1 | 12/2001 | Cabilly et al. |
| 6,333,167 B1 | 12/2001 | Quinet et al. |
| 6,555,319 B2 | 4/2003 | Wong et al. |
| 6,593,291 B1 | 7/2003 | Green et al. |
| 6,610,293 B1 | 8/2003 | Fischer et al. |
| 6,677,436 B1 | 1/2004 | Sato et al. |
| 6,703,494 B2 | 3/2004 | Kirchhofer et al. |
| 6,986,894 B2 | 1/2006 | O'Brien et al. |
| 7,749,498 B2 | 7/2010 | Jiao et al. |
| 7,824,677 B2 | 11/2010 | Wong et al. |
| 2002/0025508 A1 | 2/2002 | Fechteler et al. |
| 2002/0065327 A1 | 5/2002 | Jiao et al. |
| 2003/0082636 A1 | 5/2003 | Wong et al. |
| 2003/0087372 A1 | 5/2003 | DelaCruz et al. |
| 2003/0109680 A1 | 6/2003 | Wong et al. |
| 2003/0119075 A1 | 6/2003 | Kirchhofer et al. |
| 2003/0124117 A1 | 7/2003 | Refino et al. |
| 2003/0176664 A1 | 9/2003 | Jiao et al. |
| 2004/0033200 A1 | 2/2004 | Ezban et al. |
| 2004/0126816 A1 | 7/2004 | Kirchhofer et al. |
| 2004/0229282 A1 | 11/2004 | Wong et al. |
| 2005/0089929 A1 | 4/2005 | Jiao et al. |
| 2005/0271664 A1 | 12/2005 | Wong et al. |
| 2006/0039901 A1 | 2/2006 | Jiao et al. |
| 2006/0159675 A1 | 7/2006 | Jiao et al. |
| 2006/0235209 A9 | 10/2006 | Jiao et al. |
| 2009/0041766 A1 | 2/2009 | Jiao et al. |
| 2009/0092602 A1 | 4/2009 | Jiao et al. |
| 2009/0136501 A1 | 5/2009 | Jiao et al. |
| 2009/0252726 A1 | 10/2009 | Jiao et al. |

FOREIGN PATENT DOCUMENTS

EP     0 239 400 A2    9/1987
(Continued)

OTHER PUBLICATIONS

Alberts et al. (2002). *The Cell*, Garland Science 4th edition, pp. 161, Fig. 3-42.
Albrecht et al. (1992). "An ELISA for Tissue Factor Using Monoclonal Antibodies," *Blood Coagulation and Fibrinolysis* 3:263-270.
Almus et al. (1990). "Properties of Factor VIIa/Tissue Factor Complexes in an Umbilical Vein Model," *Blood* 76(2):354-360.
Amirkhosravi et al. (2001). *Suppl. To J. of Thrombosis and Haemostasis* Abstract: OC1021.
Ardaillou et al. (1992). "Glomerular Tissue Factor Stimulates Thromboxane Synthesis in Human Platelets via Thrombin Generation," *Kidney International* 41:361-368.
Asadullah, K. et al. (Dec. 1999). "The Pathophysiological Role of Cytokines in Psoriasis," *Drugs of Today* 35(12):913-924.

(Continued)

*Primary Examiner* — Michael Szperka
(74) *Attorney, Agent, or Firm* — Morrison & Foerster LLP

(57) ABSTRACT

Disclosed is a method for preventing or treating thrombosis in a mammal such as a primate and particularly a human patient. A preferred method includes administering to the mammal a therapeutically effective amount of at least one humanized antibody, chimeric antibody, or fragment thereof that binds specifically to human tissue factor (TF). Additional methods and kits are provided.

24 Claims, 14 Drawing Sheets

FOREIGN PATENT DOCUMENTS

| | | |
|---|---|---|
| EP | 0 239 400 A3 | 9/1987 |
| EP | 0 239 400 B1 | 9/1987 |
| EP | 0 420 937 B1 | 4/1991 |
| EP | 1 069 185 A1 | 1/2001 |
| JP | 4-502408 T | 5/1992 |
| JP | 1-503438 A | 11/1998 |
| JP | 2001-516214 T | 9/2001 |
| WO | WO-89/12463 A1 | 12/1989 |
| WO | WO-90/07861 A1 | 7/1990 |
| WO | WO-91/18019 A1 | 11/1991 |
| WO | WO-94/05328 A1 | 3/1994 |
| WO | WO-96/13593 A2 | 5/1996 |
| WO | WO-96/13593 A3 | 5/1996 |
| WO | WO-96/18105 A1 | 6/1996 |
| WO | WO-96/40921 A1 | 12/1996 |
| WO | WO-98/40408 A1 | 9/1998 |
| WO | WO-98/51321 A1 | 11/1998 |
| WO | WO-99/43713 A1 | 9/1999 |
| WO | WO-00/18398 A1 | 4/2000 |
| WO | WO-01/27079 A2 | 4/2001 |
| WO | WO-01/30333 A2 | 5/2001 |
| WO | WO-01/70984 A2 | 9/2001 |
| WO | WO-01/70984 A3 | 9/2001 |
| WO | WO-03/029295 A1 | 4/2003 |
| WO | WO-03/037911 A2 | 5/2003 |
| WO | WO-03/037911 A3 | 5/2003 |
| WO | WO-2005/004793 A2 | 1/2005 |
| WO | WO-2005/004793 A3 | 1/2005 |
| WO | WO-2005/004793 C2 | 1/2005 |
| WO | WO-2005/072126 A2 | 8/2005 |
| WO | WO-2005/072126 A3 | 8/2005 |

OTHER PUBLICATIONS

Barstad et al. (1995). "Procoagulant Human Monocytes Mediate Tissue Factor/Factor VIIa-Dependent Platelet-Thrombus Formation when Exposed to Flowing Nonanticoagulated Human Blood," *Arteriosclerosis, Thrombosis, and Vascular Biology* 15(1):11-16 (1995).
Beers et al. (1999). *The Merck Manual of Diagnosis and Therapy*, 17th edition, Merck Research Laboratories, pp. 1654-1681.
Benedict et al. (Feb. 1995). "Monoclonal Antibody to Tissue Factor Inhibits Intravascular Thrombosis without Impairing Extravascular Hemostasis," *JACC* Abstract 1012-1104, p. 366A.
Benhar et al. (1994). "Rapid Humanization of the Fv of Monoclonal Antibody B3 by Using Framework Exchange of the Recombinant Immunotoxin B3(Fv)-PE38," *Proc. Natl. Acad. Sci. USA* 91:12051-12055.
Bernhard, G.R. et al. (2001). "Efficacy and Safety of Recombinant Human Activated Protein C for Severe Sepsis," *The New England Journal of Medicine* 344:699-709.
Berzofsky, J.A. et al. (1993). "Immunogenicity and Antigen Structure," Chapter 8 in *Fundamental Immunology*, Paul, W.E. ed., Raven Press: New York, NY, p. 242.
Bird, R.E. et al. (Oct. 21, 1988). "Single-Chain Antigen-Binding Proteins," *Science* 242(4877):423-426.
Bjoern et al. (1991). "Human Plasma and Recombinant Factor VII," *The Journal of Biological Chemistry* 266(17):11051-10057.
Bokarewa et al. (Sep. 2002). "Intra-Articular Tissue Factor/Factor VII Complex Induces Chronic Arthritis," *Inflamm. Res.* 51(9):471-477.
Booy et al. (2006). "Monoclonal and Bispecific Antibodies as Novel Therapeutics," *Arch. Immunol. Ther. Exp.* 54:85-101.
Boulianne et al. (1984). "Production of Functional Chimeric Mouse/Human Antibody," *Nature* 312:643-646.
Broze, G.J., Jr. (1982). "Binding of Human Factor VII and VIIa to Monoytes," *J. Clin. Invest.* The American Society for Clinical Investigation, Inc. 70:526-535.
Bruggemann et al. (1989). "The Immunogenicity of Chimeric Antibodies," *J. Exp. Med.* 170:2153-2157.
Busso, N. et al. (Mar. 2003). "Role of the Tissue Factor Pathway in Synovial Inflammation," *Arthritis Rheum.* 48(3):651-659.
Cacia et al. (1996). "Isomerization of an Aspartic Acid Residue in the Complementarity-Determining Regions of a Recombinant Antibody to Human IgE: Identification and Effect on Binding Affinity," *Biochemistry* 35:1897-1903.
Camerer et al. (2000). "Tissue Factor—And Factor X-Dependent Activation of Protease-Activated Receptor 2 by Factor VIIa," *Proc. Natl. Acad. Sci. USA* 97(10):5255-5260.
Carraway, M.S. et al. (May 1, 2003). "Blockade of Tissue Factor," *American Journal of Respiratory and Critical Care Medicine* 167(9):1200-1209.
Carson et al. (1985). "Monoclonal Antibodies against Bovine Tissue Factor, which Block Interaction with Factor VII," *Blood* 66(1):152-156.
Carson et al. (1987). "An Inhibitory Monoclonal Antibody against Human Tissue Factor," *Blood* 70(2):490-493.
Carter et al. (1992). "Humanization of an Anti-p185HER2 Antibody for Human Cancer Therapy," *Proc. Natl. Acad. Sci. USA* 89:4285-4289.
Casipit et al. (1998). "Improving the Binding Affinity of an Antibody Using Molecular Modeling Site Directed Mutagenesis," *Protein Science* 7:1671-1680.
Cate et al. (1993). "The Activation of Factor X and Prothrombin by Recombinant Factor VIIa In Vivo is Mediated by Tissue Factor," *The Journal of Clinical Investigation* 92:1207-1212.
Caulfield, M.J. et al. (1992). "A Pathogenic Monoclonal Antibody, G8, is Characteristic of Antierythrocyte Autoantibodies from Coombs'-Positive NZB Mice," *The Journal of Immunology* 148(7):2069-2073.
Chapman et al. (1988). "Regulation of the Procoagulant Activity within the Bronchoalveolar Compartment of Normal Human Lung," *Am. Rev. Respir. Dis.* 137(6):1417-1425.
Chattopadhyay et al. (1992). "Molecular Recognition of Sites on Factor Xa which Participate in the Prothrombinase Complex," *The Journal of Biological Chemistry* 267(17):12323-12329.
Chothia, C. et al. (Dec. 1, 1988). "The Outline Structure of the T-Cell Alpha Beta Receptor," *The EMBO Journal* 7(12):3745-3755.
Clarke et al. (1992). "The First Epidermal Growth Factor Domain of Human Coagulation Factor VII is Essential for Binding with Tissue Factor," *Federation of European Biochemical Societies* 298(2,3):206-310.
Clarke, S. et al. (Oct. 1, 1990). "The BALB/c Secondary Response to the Sb Site of Influenza Virus Hemagglutinin. Nonrandom Silent Mutuation and Unequal Numbers of VH and Vk Mutations," *The Journal of Immunology* 145(7):2286-2296.
Co et al. (1991). "Humanized Antibodies for Antiviral Therapy," *Proc. Natl. Acad. Sci. USA* 88:2869-2873.
Collen et al. (1995). "New Thrombolytic Agents and Strategies," *Bailliere's Clinical Haematology* 8(2):425-435.
Colman, P.M. (1994). "Effects of Amino Acid Sequence Changes on Antibody-Antigen Interactions," *Research in Immunology* 145:33-36.
Contrino et al. (1994). "In Situ Characterization of Antigenic and Functional Tissue Factor Expression in Human Tumors Utilizing Monoclonal Antibodies and Recombinant Factor VIIa as Probes," *American Journal of Pathology* 145(6):1315-1322.
Couto et al. (1995). "Anti-BA46 Monoclonal Mc3: Humanization Using a Novel Positional Consensus and In Vivo and In Vitro Characterization," *Cancer Research* 55:1717-1722.
Couto et al. (1995). "Designing Human Consensus Antibodies with Minimal Positional Templates," *Cancer Research (Suppl.)* 55:5973s-5977s.
Cruse et al. (1995). *Illustrated Dictionary of Immunology*, CRC Press.
Database EMBL: MMG8LC, Accession #X60425, Oct. 21, 1991 Description "G8 (ANTI-MRBC) V(L), J(L)" XP-002305737.
Drake et al. (1989). "Functional Tissue Factor is Entirely Cell Surface Expressed on Lipopolysaccharide-Stimulated Human Blood Monocytes and a Constitutively Tissue Factor-Producing Neoplastic Cell Line," *The Journal of Cell Biology* 109:389-395.
Drake et al. (1989). "Selective Cellular Expression of Tissue Factor in Human Tissues," *American Journal of Pathology* 134(5):1087-1097.
Erlich, J.H. et al. (Mar. 1997). "Tissue Factor Initiates Glomerular Fibrin Deposition and Promotes Major Histocompatibility Complex Class II Expression in Crescentic Glomerulonephritis," *American Journal of Pathology* 150(3)873-880.
Esmon, C.T. (2001). "Role of Coagulation Inhibitors in Inflammation," *Thrombosis and Haemostasis* 86(1)51-56.

Faber et al. (2001). "A Novel Method to Determine the Topology of Peroxisomal Membrane Proteins In Vivo Using the Tobacco Etch Virus Protease," *The Journal of Biological Chemistry* 276(39):36501-36507.

Faelber, K. et al. (Oct. 12, 2001). "The 1.85 Å Resolution Crystal Structures of Tissue Factor in Complex with Humanized Fab D3h44 and of Free Humanized Fab D3h44: Revisiting the Solvation of Antigen Combining Sites," *J. Mol. Biol.* 313(1):83-97. (Client).

Fair et al. (Aug. 25, 1987). "Cooperative Interaction between Factor VII and Cell Surface-Expressed Tissue Factor," *The Journal of Biological Chemistry* 262:11692-11698.

Faulk et al. (1990). "Tissue Factor: Identification and Characterization of Cell Types in Human Placentae," *Blood* 76(1):86-96.

Fay et al. (2005). "Mutating Factor VIII: Lessons from Structure to Function," *Blood Reviews* 19:15-17.

Final Office Action mailed Sep. 9, 2004, for U.S. Appl. No. 09/990,586, filed Nov. 21, 2001, 12 pages.

Final Office Action mailed Sep. 6, 2006, for U.S. Appl. No. 10/310,113, filed Dec. 4, 2002, 18 pages.

Final Office Action mailed Sep. 6, 2006, for U.S. Appl. No. 11/087,528, filed Mar. 22, 2005, 19 pages.

Final Office Action mailed Jan. 16, 2007, for U.S. Appl. No. 10/618,338, filed Jul. 11, 2003, 11 pages.

Final Office Action mailed Dec. 10, 2007, for U.S. Appl. No. 11/087,528, filed Mar. 22, 2005, by Wong et al., 12 pages. (25.03).

Final Office Action mailed Feb. 1, 2008, for U.S. Appl. No. 10/310,113, filed Dec. 4, 2002, 14 pages.

Final Office Action mailed Jun. 19, 2008, for U.S. Appl. No. 10/618,338, filed Jul. 11, 2003, 12 pages.

Fiore, M.M. et al. (Dec. 15, 1992). "An Unusual Antibody that Blocks Tissue Factor/Factor VIIa Function by Inhibiting Cleavage Only of Macromolecular Substrates," *Blood* 80(12):3127-3134.

Flössel et al. (1994). "Immunohistochemical Detection of Tissue Factor (TF) on Paraffin Sections of Routinely Fixed Human Tissue," *Histochemistry* 101:449-453.

Foote et al. (1992). "Antibody Framework Residues Affecting the Conformation of the Hypervariable Loops," *J. Mol. Biol.* 224:487-499.

Francis et al. (2002). "Effect of Antihemostasis Agents on Experimental Tumor Dissemination," *Sem. in Thrombosis and Haemostasis* 28(1):29-38.

Furmaniak-Kazmierczak, E. et al. (Aug. 1994). "Studies of Thrombin-Induced Proteoglycan Release in the Degradation of Human and Bovine Cartilage," *J. Clin. Invest.* 92(2):472-480.

Gascoigne, N.R. et al. (May 1987). "Secretion of a Chimeric T-Cell Receptor-Immunoglobulin Protein," *Proc. Natl. Acad. Sci. USA* 84(9):2936-2940.

George et al. (1988). Chapter 12 in *Macromolecular Sequencing & Synthesis*, pp. 127-149.

Gorman et al. (1991). "Reshaping a Therapeutic CD4 Antibody," *Proc. Natl. Acad. Sci. USA* 88:4181-4185.

Gouault-Heilmann et al. (1975). "The Procoagulant Factor of Leukaemic Promyelocytes: Demonstration of Immunologic Cross Reactivity with Human Brain Tissue Factor," *British Journal of Haematology* 30:151-158.

Grabowski et al. (1993). "The Functional Expression of Tissue Factor by Fibroblasts and Endothelial Cells under Flow Conditions," *Blood* 81(2):3265-3270.

Grégoire, C. et al. (Sep. 15, 1991). "Engineered Secreted T-Cell Receptor Alpha Beta Heterodimers," *Proc. Natl. Acad. Sci. USA* 88(18):8077-81.

Griffiths et al. (1993). "Human Anti-Self Antibodies with High Specificity from Phage Display Libraries," *The EMBO Journal* 12(2):725-734.

Groves, D.J. et al. (Feb. 1987). "Production of an Ovine Monoclonal Antibody to Testosterone by an Interspecies Fusion," *Hybridoma* 6(1):71-76.

Hamaguchi et al. (1991). "FDP D-Dimer Induces the Secretion of Interleukin-1, Urokinase-Type Plasminogen Activator, and Plasminogen Activator Inhibitor-2 in a Human Promonocytic Leukemia Cell Line," *Blood* 77(1):94-100.

Hanes et al. (2000). "Picomolar Affinity Antibodies from a Fully Synthetic Naïve Library Selected and Evolved by Ribosome Display," *Nature Biotechnology* 18:1287-1292.

Hoffman et al. (1994). "Human Monocytes Support Factor X Activation by Factor VIIa, Independent of Tissue Factor: Implications for the Therapeutic Mechanism of High-Dose Factor VIIa in Hemophilia," *Blood* 83(1):38-42.

Houston, D.S. (2002). "Tissue Factor—A Therapeutic Target for Thrombotic Disorders," *Expert Opinion on Therapeutic Targets* 6(2):159-174.

Huang et al. (1998). "The Mechanism of an Inhibitory Antibody on TF-Initiated Blood Coagulation Revealed by the Crystal Structures of Human Tissue Factor, Fab 5G9 and TF5G9 Complex," *J. Mol. Biol.* 275:873-894. (client).

Huston, J.S. et al. (Aug. 1988). "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85(16):5879-5883.

Imamura et al. (1993). "Role of Macrophage Tissue Factor in the Development of the Delayed Hypersensitivity Reaction in Monkey Skin," *Cellular Immunology* 152:614-622.

International Search Report mailed on May 7, 1998, for PCT Application No. PCT/US98/04644, filed on Mar. 10, 1998, three pages. (25.40).

International Search Report mailed on Jun. 30, 2003, for PCT Application No. PCT/US02/034727, filed on Oct. 29, 2002, three pages. (26.40).

International Search Report mailed on May 18, 2005, for PCT Application No. PCT/US04/17900, filed on Jun. 4, 2004, two pages. (27.40).

Ishihara, K. et al. (Aug. 2002-Oct. 2002). "IL-6 in Autoimmune Disease and Chronic Inflammatory Proliferative Disease," *Cytokine * Growth Factor Reviews* 13(4-5):357-368.

Ito et al. (1993). "Characterization of Functionally Important Regions of Tissue Factor by Using Monoclonal Antibodies," *J. Biochem.* 114(5):691-696.

Jager et al. (1993). "Current Status of Cancer Immunodetection with Radiolabeled Human Monoclonal Antibodies," *Seminars in Nuclear Medicine* XXIII(2):165-179.

James et al. (2002). "Inhibition of Tissue Factor Activity Reduces the Density of Cellular Network Formation in an In Vitro Model of Angiogenesis," *Biochemical Society Transactions* 30(2):217-221.

Janeway, C.A. Jr. et al. (1997). "Structure of the Antibody Molecule and Immunoglobulin of Genes," Chapter 3 in "Part II, The Recognition of Antigen," in *Immunobiology*, 3$^{rd}$ edition, Garland Press, 3:1-3:11.

Janeway et al. (1997). *Immunobiology*, 3$^{rd}$ edition, Garland Press, 3:7-3:11.

Jang (1992). "Antithrombotic Effect of a Monoclonal Antibody against Tissue Factor in a Rabbit Model of Platelet-Mediated Arterial Thrombosis," *Arteriosclerosis and Thrombosis* 12(8):948-954.

Jones, P.T. et al. (May 29, 1986-Jun. 4, 1986). "Replacing the Complementarity-Determining Regions in a Human Antibody with Those from a Mouse," *Nature* 321(6069):522-525.

Junghans, R.P. et al. (Dec. 1, 1993). "Pharmacokinetics and Bioactivity of 1,4,7,10-tetra-azacyclododecane off′,N″,N″″-tetraacetic acid (DOTA)-bismuth-conjugated anti-Tac Antibody for Alpha-Emitter (212Bi) Therapy," *Cancer Res.* 52(23):5683-5689.

Kao et al. (1993). "Chimeric Antibodies with Anti-Dextran-Derived Complementarity-Determining Regions and Anti-p-Azophenylarsonate-Derived Framework Regions," *The Journal of Immunology* 151:1968-1979.

Kappler, J. et al. (Aug. 30, 1994). "Binding of a Soluble Alpha Beta T-Cell Receptor to Superantigen/Major Histocompatibility Complex Ligands," *Proc. Natl. Acad. Sci. USA* 91(18):8462-8466.

Kincaid-Smith, P. (1975). "Participation of Intravascular Coagulation in the Pathogenesis of Glomerular and Vascular Lesions," *Kidney International* 7:242-253.

Kirchhofer, D. et al. (Dec. 2000). "Epitope Location on Tissue Factor Determines the Anticoagulant Potency of Monoclonal Anti-Tissue Factor Antibodies," *Thrombosis and Haemostatis* 84(6):1072-1081.

Kirchhofer et al. (2001). "The Tissue Factor Region that Interacts with Factor Xa in the Activation of Factor VII," *Biochemistry* 40:675-682.

Knappik et al. (2000). "Fully Synthetic Human Combinatorial Antibody Libraries (HuCAL) Based on Modular Consensus Frameworks and CDRs Randomized with Trinucleotides," *J. Mol. Biol.* 296:57-86.

Konigsberg et al. (2001). "The TF:VIIa Complex: Clinical Significance, Structure-Function Relationships and its Role in Signaling and Metastasis," *Thrombosis Haemostasis* 86:757-771.

Kozbor, D. et al. (1983). "The Production of Monoclonal Antibodies from Human Lymphocytes," *Immunology Today* 4:72-79.

Kumar et al. (1991). "Identification of Molecular Sites on Factor VII which Mediate its Assembly and Function in the Extrinsic Pathway Activation Complex," *The Journal of Biological Chemistry* 266(2):915-921.

Kumar et al. (1993). "Specific Molecular Interaction Sites on Factor VII Involved in Factor X Activation," *Eur. J. Biochem.* 217:509-518.

Kurucz, I. et al. (May 1, 1993). "A Bacterially Expressed Single-Chain Fv Construct from the 2B4 T-Cell Receptor," *Proc. Natl. Acad. Sci. USA* 90(9):3830-3834.

Leong et al. (2001). "Adapting Pharmacokinetic Properties of a Humanized Anti-Interleukin-8 Antibody for Therapeutic Applications Using Site-Specific Pegylation," *Cytokine* 16(3):106-119.

Levi et al. (1994). "Inhibition of Endotoxin-Induced Activation of Coagulation and Fibrinolysis by Pentoxifylline or by a Monoclonal Anti-Tissue Factor Antibody in Chimpanzees," *The Journal of Clinical Investigation, Inc.* 93:114-120.

Lewis, A.P. et al. (1993). "Generation of Humanized Monoclonal Antibodies by 'Best Fit' Framework Selection and Recombinant Polymerase Chain Reaction," *Year Immunol.* 7:110-118.

Lin, A.Y. et al. (Aug. 10, 1990). "Expression of T Cell Antigen Receptor Heterodimers in a Lipid-Linked Form," *Science* 249(4969):677-679.

Lobuglio et al. (1989). "Mouse/Human Chimeric Monoclonal Antibody in Man: Kinetics and Immune Response," *Proc. Natl. Acad. Sci. USA* 86:4220-4224.

Maekawa et al. (1993). "Complement-Dependent Immunosuppressive Anti-Tissue Factor Monoclonal Antibody: The Establishment of Monoclonal Antibodies and their Effect on Mixed Lymphocyte Reaction," *Transplantation Proceedings* 25(4):2713-2715.

Maimone, D. et al. (Jan. 1993). "T Cell Lymphokine-Induced Secretion of Cytokines by Monocytes from Patients with Multiple Sclerosis," *Cellular Immunology* 146(1):96-106.

Mariuzza, R.A. et al. (May 5, 1989). "Secretion of a Homodimeric V Alpha C Kappa T-Cell Receptor-Immunoglobulin Chimeric Protein," *Journal of Biological Chemistry* 264(13):7310-7316.

Martin et al. (1995). "Tissue Factor: Molecular Recognition and Cofactor Function," *The FASEB Journal* 9:852-859.

Martin et al. (Jun. 15, 1994). "Activation of Factor X by Factor VIIa on Monocyte Cell Surfaces," *Blood* 83(12):3828-3829.

Marty, I. et al. (Mar. 2001). "Amelioration of Collagen-Induced Arthritis by Thrombin Inhibition," *Journal of Clin. Invest.* 107(5):531-640.

Masuda et al. (1996). "Association of Tissue Factor with a γ Chain Homodimer of the IgE Receptor Type I in Cultured Human Monocytes," *Eur. J. Immunol.* 26:2529-2532.

Mateo et al. (1997). "Humanization of a Mouse Monoclonal Antibody that Blocks the Epidermal Growth Factor Receptor: Recovery of Antagonistic Activity," *Immunotechnology* 3:71-81.

Matthay, M.A. (2001). "Severe Sepsis—A New Treatment with Both Anticoagulant and Antiinflammatory Properties," *The New England Journal of Medicine* 344:759-762.

McGee et al. (1991). "Functional Difference between Intrinsic and Extrinsic Coagulation Pathways," *The Journal of Biological Chemistry* 266(13):8079-8085.

Mechtcheriakova, D. et al. (Jan. 2001). "Specificity, Diversity, and Convergence in VEGF and TNF-α Signaling Events Leading to Tissue Factor Up-Regulation via EGR-1 in Endothelial Cells," *The FASEB Journal* 15:230-242.

Medline Encyclopedia definition of "sepsis" located at <http://www.nlm.nih.gov/medlineplus/print/ency/article/000666.htm....>, last visited on Jul. 20, 2007, 3 pages.

Merriam-Webster Online Dictionary, downloaded Oct. 11, 2005, World Wide Web at m-w.com, Definition of Thrombosis, 2 pages.

Miller, D.L. et al. (Jun. 2002). "Extrinsic Coagulation Blockade Attenuates Lung Injury and Proinflammatory Cytokine Release after Intratracheal Lipopolysaccharide," *American Journal of Respiratory Cell and Molecular Biology* 26(6):650-658.

Minnema, M.C. et al. (Feb. 15, 2000). "Recombinant Human Antithrombin III Improves Survival and Attenuates Inflammatory Responses in Baboons Lethally Challenged with *Escherichia coli*," *Blood* 95(4):1117-1123.

More, L. et al. (Aug. 1993). "Immunohistochemical Study of Tissue Factor Expression in Normal Intestine and Idiopathic Inflammatory Bowel Disease," *J. Clin. Pathol.* 46:703-708.

Morris, R. et al. (Jan. 1994). "Thrombin in Inflammation and Healing: Relevance to Rheumatoid Arthritis," *Annals of the Rheumatic Diseases* 53:72-79.

Morrison et al. (1984). "Chimeric Human Antibody Molecules: Mouse Antigen-Binding Domains with Human Constant Region Domains," *Proc. Natl. Acad. Sci. USA* 81:6851-6855.

Morrison, S. (1985). "Transfectomas Provide Novel Chimeric Antibodies," *Science* 229:1202-1207.

Morrison, S.L. (1992). "In Vitro Antibodies: Strategies for Production and Application," *Ann. Rev. Immunol.* 10:239-265.

Morrison, S.L. et al. (1989). "Genetically Engineered Antibody Molecules," *Advances in Immunology* 44:65-93.

Morrissey et al. (1988). "Monoclonal Antibody Analysis of Purified and Cell-Associated Tissue Factor," *Thrombosis Research* 52:247-261.

Morrissey et al. (1988). "Resolution of Monomeric and Heterodimeric Forms of Tissue Factor, the High-Affinity Cellular Receptor for Factor VII," *Thrombosis Research* 50:481-493.

Morrow, D.A. et al. (Apr. 2005). "Potent Inhibition of Thrombin with a Monoclonal Antibody Against Tissue Factor (Sunol-cH36): Results of the PROXIMATE-TIMI 27 Trial," *European Heart Journal* 26(7):682-688.

Mueller et al. (1992). "Expression of Tissue Factor by Melanoma Cells Promote Efficient Hemaotgenous Metasasis," *Proc. Natl. Acad. Sci. USA* 89:11832-11836.

Muller et al. (1994). "Structure of the Extracellular Domain of Human Tissue Factor: Location of the Factor VIIa Binding Site," *Biochemistry* 33:10864-10870.

Nakano, S. et al. (Mar. 1999-Apr. 1999). "Characteristics of the Protease Activity in Synovial Fluid from Patients with Rheumatoid Arthritis and Osteoarthritis," *Clinical and Experimental Rheumatology* 17:161-170.

Nemerson et al. (1986). "An Ordered Addition, Essential Activation Model of the Tissue Factor Pathway of Coagulation: Evidence for a Conformational Cage," *Biochemistry* 25:4020-4033.

Ngo, C.V. (2007, e-pub. Dec. 27, 2006). "CNTO 859, A Humanized Anti-Tissue Factor Monoclonal Antibody, is a Potent Inhibitor of Breast Cancer Metastasis and Tumor Growth in Xenograft Models," *Int. J. Cancer* 120:1261-1267.

Noguchi et al. (1989). "Correlation between Antigenic and Functional Expression of Tissue Factor on Surface of Cultured Human Endothelial Cells Following Stimulation by Lipopolysaccharide Endotoxin," *Thrombosis Research* 55:87-97.

Non-Final Office Action mailed Mar. 11, 2004, for U.S. Appl. No. 09/990,586, filed Nov. 21, 2001, 12 pages.

Non-Final Office Action mailed Sep. 22, 2004, for U.S. Appl. No. 10/293,417, filed Nov. 12, 2002, six pages.

Non-Final Office Action mailed Oct. 21, 2005, for U.S. Appl. No. 10/310,113, filed Dec. 4, 2002, 27 pages.

Non-Final Office Action mailed Mar. 24, 2006, for U.S. Appl. No. 11/087,528, filed Mar. 22, 2005, 13 pages.

Non-Final Office Action mailed Jun. 14, 2006, for U.S. Appl. No. 10/618,338, filed Jul. 11, 2003, 12 pages.

Non-Final Office Action mailed Apr. 4, 2007, for U.S. Appl. No. 11/087,528, filed Mar. 22, 2005, 15 pages.

Non-Final Office Action mailed May 11, 2007, for U.S. Appl. No. 10/310,113, filed Dec. 4, 2002, 14 pages.

Non-Final Office Action mailed Sep. 6, 2007, for U.S. Appl. No. 10/618,338, filed Jul. 11, 2003, eight pages.

Non-Final Office Action mailed Feb. 4, 2008, for U.S. Appl. No. 10/764,140, filed Jan. 22, 2004, 12 pages.
Non-Final Office Action mailed Sep. 15, 2008, for U.S. Appl. No. 11/122,622, filed May 5, 2005, 13 pages.
Non-Final Office Action mailed Feb. 4, 2009, for U.S. Appl. No. 10/618,338, filed Jul. 11, 2003, eight pages.
Non-Final Office Action mailed Dec. 30, 2009, for U.S. Appl. No. 12/136,718, filed Jun. 10, 2008, 12 pages.
Novotny, J. et al. (Oct. 1, 1991). "A Soluble, Single-Chain T-Cell Receptor Fragment Endowed with Antigen-Combining Properties," *Proc. Natl. Acad. Sci. USA* 88(19):8646-8650.
Oi, V.T. et al. (1986). "Chimeric Antibodies," *BioTechniques* 4(3):214-221.
Ollivier et al. (1998). "Tissue Factor-Dependent Vascular Endothelial Growth Factor Production by Human Fibroblasts in Response to Activated Factor VII," *Blood* 91(8):2698-2703.
Olsson, L. et al. (1983). "Human-Human Monoclonal Antibody-Producing Hybridomas: Technical Aspects," *Methods in Enzymology* 92:3-16.
Onda, T. et al. (Dec. 1995). "A Phage Display System for Detection of T Cell Receptor-Antigen Interactions," *Molecular Immunology* 32(17-18):1387-1397.
Østerud et al. (1979). "The Interaction of Human Blood Coagulation Factor VII and Tissue Factor: The Effect of Anti Factor VII, Anti Tissue Factor and Diisopropylfluorophosphate," *Biochemical and Biophysical Research Communications* 88(1):59-67.
Osterud, B. et al. (Jun. 2000). "Induction of Tissue Factor Expression in Whole Blood: Lack of Evidence for the Presence of Tissue Factor Expression in Granulocytes," *Thrombosis Haemostasis* 83:861-867.
Owens et al. (1994). "The Genetic Engineering of Monoclonal Antibodies," *Journal of Immunological Methods* 168:149-165.
Padlan (1990). "On the Nature of Antibody Combining Sites: Unusual Structural Features that May Confer on these Sites an Enhanced Capacity for Binding Ligands," *Proteins* 7:112-124.
Padlan (1991). "A Possible Procedure for Reducing the Immunogenicity of Antibody Variable Domains while Preserving their Ligand-Binding Properties," *Molecular Immunology* 28(4/5):489-498.
Padlan (1994). "Anatomy of the Antibody Molecule," *Molecular Immunology* 31(3):169-217.
Palmerini, T. et al. (Oct. 19, 2004). "Monocyte-Derived Tissue Factor Contributes to Stent Thrombosis in an In Vitro System," *J. Am. Coll. Cardio.* 44(8):1570-1577.
Parmley, S.F. et al. (Dec. 20, 1988). "Antibody-Selectable Filamentous Fd Phage Vectors: Affinity Purification of Target Genes," *Gene* 73(2):305-318.
Pawashe et al. (Jan. 1994). "A Monoclonal antibody against Rabbit Tissue Factor Inhibits Thrombus Formation in Stenotic Injured Rabbit Carotid Arteries," *Tissue Factor and Intravascular Thrombosis* 74(1):56-63.
Ploplis et al. (Jul. 15, 1987). "Initiation of the Extrinsic Pathway of Coagulation—Association of Factor VIIa with a Cell Line Expressing Tissue Factor," *The Journal of Biological Chemistry* 262:9503-9508.
Portolano, S. et al. (Feb. 1, 1993). "Lack of Promiscuity in Autoantigen-Specific H and L Chain Combinations as Revealed by Human H and L Chain 'Roulette'," *J. Immunology* 150(3):880-887.
Poster Presentation: *Experimental Biology* 2001, Mar. 31-Apr. 4, 2001, Orlando, Florida, Anti-Tissue Factor Antibodies, Poster No. 946: "Immunotherapy of Cancer," 14 pages.
Presta et al. (2001). "Generation of a Humanized, High Affinity Anti-Tissue Factor Antibody for Use as a Novel Antithrombotic Therapeutic," *Thrombosis Haemostasis* 85:379-389.
Price et al. (2004). "Tissue Factor and Tissue Factor Pathway Inhibitor," *Anaesthesia* 59:483-492.
Queen et al. (1989). "A Humanized Antibody that Binds to the Interleukin 2 Receptor," *Proc. Natl. Acad. Sci. USA* 86:10029-10033.
Queen et al. (1989). "Cell-Type Specific Regulation of a k Immunoglobin Gene by Promoter and Enhancer Elements," *Immunological Reviews* 89:49-68.

Ragni, M. et al. (May 15, 1996). "Monoclonal Antibody against Tissue Factor Shortens Tissue Plasminogen Activator Lysis Time and Prevents Reocclusion in a Rabbit Model of Carotid Artery Thrombosis," *Circulation* 93(10):1913-1918.
Rangel-Frausto, M.S. (2005). Sepsis: Still Going Strong, *Archives of Medical Research* 36:672-681.
Rao, L.V. et al. (Oct. 1, 1989). "Purification and Characterization of Rabbit Tissue Factor," *Thrombosis Research* 56:109-118.
Rehemtulla et al. (Jun. 5, 1991). "The Integrity of the Cysteine 186-Cysteine 209 Bond of the Second Disulfide Loop of Tissue Factor is Required for Binding of Factor VII," *The Journal of Biological Chemistry* 266(16):10294-10299.
Reichart (2001). "Monocolonal Antibodies in the Clinic," *Nature Biotechnology* 19:819-822.
Reichmann et al. (1988). "Reshaping Human Antibodies for Therapy," *Nature* 332:323-327.
Riewald et al. (2001). "Mechanistic Coupling of Protease Signaling and Initiation of Coagulation by Tissue Factor," *Proc. Natl. Acad. Sci. USA* 98(14):7742-7747.
Roberston (2002). "Genentech Awarded Critical Antibody Patent," *Nature Biotechnology* 20:108.
Roguska et al. (1994). "Humanization of Murine Monoclonal Antibodies through Variable Domain Resurfacing," *Protein Engineering* 9(10):895-904.
Roguska et al. (1996). "A Comparison of Two Murine Monoclonal Antibodies Humanized by CDR-Grafting and Variable Domain Resurfacing," *Protein Engineering* 9(10):895-904.
Rudikoff et al. (1982). "Single Amino Acid Substitution Altering Antigen-Binding Specificity," *Proc. Natl. Acad. Sci. USA* 79:1979-1983.
Ruf et al. (1991). "An Anti-Tissue Factor Monoclonal Antibody which Inhibits TF-VIIa Complex is a Potent Anticoagulant in Plasma," *Thrombosis and Haemostasis*, F.K. Schattauer Verlagsgesellschaft mbH (Stuttgart) 66(5):529-533.
Ruf et al. (1991). "Antibody Mapping of Tissue Factor Implicates Two Different Exon-Encoded Regions in Function," *Biochem. J.* 278:729-733.
Ruf et al. (1999). "Tissue Factor Signaling," *Thrombosis and Haemostasis* 82(2):175-182.
Ruf et al. (Apr. 1994). "Structural Biology of Tissue Factor, the Initiator of Thrombogenesis In Vivo," *The FASEB Journal* 8:385-390.
Ruf et al. (Aug. 25, 1991). "Characterization of Factor VII Association with Tissue Factor in Solution—High and Low Affinity Calcium Binding Sites in Factor VII Contribute to Functionally Distinct Interactions," *The Journal of Biological Chemistry* 26:15719-15725.
Ruf et al. (Feb. 5, 1991). "Phospholipid-Independent and -Dependent Interactions required for Tissue Factor Receptor and Cofactor Function," *The Journal of Biological Chemistry* 266:2158-2166.
Ruf et al. (Nov. 5, 1992). "Tissue Factor Residues 157-167 are Required for Efficient Proteolytic Activation of Factor X and Factor VII," *The Journal of Biological Chemistry* 267(31):22206-22210.
Ruf et al. (Oct. 1991). "Two Sites in the Tissue Factor Extracellular Domain Mediate the Recognition of the Ligand Factor VIIa," *Proc. Natl. Acad. Sci. USA* 88:8430-8434.
Ryan et al. (Aug. 15, 1992). "Tumor Necrosis Factor-Induced Endothelial Tissue Factor is Associated with Subendothelial Matrix Vesicles but is not Expressed on the Apical Surface," *Blood* 80(4):966-974.
Sakai et al. (Jun. 15, 1989). "Binding of Human Factors VII and VIIa to a Human Bladder Carcinoma Cell Line (J82)—Implications for the Initiation of the Extrinsic Pathway of Blood Coagulation," *The Journal of Biological Chemistry* 264(17):9980-9988.
Salatti et al. (1993). "Modulation of Procoagulant Activity of Extracellular Endothelial Matrix by Anti-Tissue Factor Antibody and the Synthetic Peptide Arg-Gly-Asp-Val. Experiments with Flowing Non-Anticoagulated Human Blood," *Blood Coagulation and Fibrinolysis* 4:881-890.
Saldanha et al. (1999). "A Single Backmutation in the Human kIV Framework of a Previously Unsuccessfully Humanized Antibody Restores the Binding Activity and Increases the Secretion in cos Cells," *Molecular Immunology* 36:709-719.

Sandset et al. (Sep. 15, 1991). "Immunodepetion of Extrinsic Pathway Inhibitor Sensitizes Rabbits to Endotoxin-Induced Intravascular Coagulation and the Generalized Schwartzman Reaction," *Blood* 78(6):1496-1502.

Schlueter, C.J. et al. (Mar. 15, 1996). "Specificity and Binding Properties of a Single-Chain T Cell Receptor," *Journal of Molecular Biology* 256(5):859-869.

Schopf, R.E. et al. (1993). "Enhanced Procoagulant Activity of Mononuclear Leukocytes in Patients with Atopic Dermatitis and Psoriasis," *Arch. Dermatol. Res.* 285:305-309.

Segal, J. et al. (Dec. 2000). "Tissue Factor Activity in Patients with Systemic Lupus Erythematosus: Association with Disease Activity," *The Journal of Rheumatology* 27:2827-2832.

Shearman et al. (1991). "Construction, Expression and Characterization of Humanized Antibodies Directed against the Human α/β T Cell Receptor," *The Journal of Immunology* 147:4366-4373.

Shen, B.Q. et al. (Feb. 16, 2001). "Vascular Endothelial Growth Factor KDR Receptor Signaling Potentiates Tumor Necrosis Factor-Induced Tissue Factor Expression in Endothelial Cells," *The Journal of Biological Chemistry* 276(7):5281-5286.

Skopouli et al. (1995). "Cytokines in Sjogren's Syndrome," *Annales de Medecine Interne* 146(4):219-222.

Smith, G.P. et al. (1993). "Libraries of Peptides and Proteins Displayed on Filamentous Phage," *Methods in Enzymology*, 217:228-257.

Soo Hoo, W.F. et al. (May 15, 1992). "Characterization of a Single-Chain T-Cell Receptor Expressed in *Escherichia coli,*" *Proc. Natl. Acad. Sci. USA* 89(10):4759-63.

Speidel et al. (Jan. 1996). "Procoagulant Activity on Injured Arteries and Associated Thrombi is Mediated Primarily by the Complex of Tissue Factor and Factor VIIa," *Pathophysiology and Natural History, Coronary Artery Disease* 7(1):58-62.

Stephens et al. (1994). "Production of Tissue Factor by Monocyte Progenitor Cells," *Thrombosis Research* 76(1):33-45.

Sturm et al. (1992). "Immunohistological Detection of Tissue Factor in Normal and Abnormal Human Mammary Glands Using Monoclonal Antibodies," *Virchows Archive A Pathological Anatomy and Histopathology* 421:79-86.

Tan et al. (2002). "Superhumanized Antibodies: Reduction of Immunogenic Potential by Complementarity-Determining Region Grafting with Human Germline Sequences: Application to an Anti-CD28," *The Journal of Immunology* 169:1119-1125.

Taylor et al. (1987). "Protein C Prevents the Coagulopathic and Lethal Effects of *Escherichia coli* Infusion in the Baboon," *J. Clin. Invest.* 79:918-925.

Taylor, F.B. (2001). "Staging of the Pathophysiologic Responses of the Primate Microvasculature to *Escherichia coli* and Endotoxin: Examination of the Elements of the Compensated Response and their Links to the Corresponding Uncompensated Lethal Variants," *Crit. Care. Med.* 29(7):S78-89.

Tempest et al. (1991). "Reshaping a Human Monoclonal Antibody to Inhibit Human Respiratory Syncytial Virus Infection In Vivo," *Bio/Technology* 9:266-271.

Teng et al. (1983). "Construction and Testing of Mouse-Human Hetermyelomas for Human Monoclonal Antibody Production," *Proc. Natl. Acad. Sci. USA* 80:7308-7312.

Tomizuka et al. (2000). Double Trans-Chromosomic Mice; Maintenance of Two Individual Human Chromosome Fragments Containing Ig heavy and k lock and Expression of Fully Human Antibodies, *Proc. Natl. Acad. Sci. USA* 97(2):722-727.

Toomey et al. (Oct. 15, 1991). "Localization of the Human Tissue Factor Recognition Determinant of Human Factor VIIa," *The Journal of Biological Chemistry* 266(20):19198-19202.

Tsao et al. (Apr. 1984). "Monocytes can be Induced by Lipopolysaccharide-Triggered T Lymphocytes to Express Functional Factor VII/VIIa Protease Activity," *J. Exp. Med.* 159:1042-1057.

Tsuda et al. (Jul. 1, 1993). "Development of Antitissue Factor Antibodies in Patients after Liver Surgery," *Blood* 82(1):96-102.

Varisco P.A. et al. (Oct. 2000). "Effect of Thrombin Inhibition on Synovial Inflammation in Antigen Induced Arthritis," *Annals of Rheumatic Diseases* 59(10):781-787.

Vaughan et al. (1996). "Human Antibodies with Sub-Nanomolar Affinities Isolated from a Large Non-Immunized Phage Display Library," *Nature Biotechnology* 14:309-314.

Verhoeyen et al. (1988). "Reshaping Human Antibodies: Grafting an Antilysozyme Activity," *Science* 239:1534-1536.

Wakefield, A.J. et al. (Feb. 1994). "Immunohistochemical Study of Vascular Injury in Acute Multiple Sclerosis," *Journal of Clinical Pathology* 47(2):129-133.

Walsh, J.D. et al. (1991). "Discordant Expression of Tissue Factor Antigen and Procoagulant Activity on Human Monocytes Activated with LPS and Low Dose Cycloheximide," *Thrombosis and Haemostasis*, F.K. Achattauer Verlagsgesellschaft mbH (Stuttgart) 66(5):552-558.

Ward, E.S. (Apr. 20, 1992). "Secretion of T Cell Receptor Fragments from Recombinant *Escherichia coli* Cells," *Journal of Molecular Biology* 224(4):885-890.

Ward, E.S. (Aug. 1991). "Expression and Secretion of T-Cell Receptor V Alpha and V Beta Domains Using *Escherichia coli* as a Host," *Scand. J. Immunol.* 34:215-220.

Warr et al. (Apr. 1, 1990). "Disseminated Intravascular Coagulation in Rabbits Induced by Administration of Endotoxin or Tissue Factor: Effect of Anti-Tissue Factor Antibodies and Measurement of Plasma Extrinsic Pathway Inhibitor Activity," *Blood* 75(7):1481-1489.

Watson et al. (1987). *Molecular Biology of the Gene*, 4th edition, The Benjamin/Cummings Publishing Company, Inc., 840.

Webber, K.O. et al. (Mar. 1995). "Preparation and Characterization of a Disulfide-Stabilized Fv Fragment of the Anti-Tac Antibody: Comparison with its Single-Chain Analog," *Molecular Immunology* 32(4):249-258.

Weinberg, J.B. et al. (Aug. 1991). "Extravascular Fibrin Formation and Dissolution in Synovial Tissue of Patients with Osteoarthritis and Rheumatoid Arthritis," *Arthritis and Rheumatism* 34(8):996-1005.

Welty-Wolf, K.B. et al. (Nov. 15, 2001). "Coagulation Blockade Prevents Sepsis-Induced Respiratory and Renal Failure in Baboons," *American Journal of Respiratory and Critical Care Medicine* 164(10 Pt 1):1988-1996.

Welty-Wolf, K.E. et al. (Oct. 2001). "Tissue Factor in Experimental Acute Lung Injury," *Seminars in Hematology* 38(4):35-38.

Welty-Wolf, K.E. et al. (Jan. 2006, e-pub. Aug. 12, 2005). "Blockade of Tissue Factor-Factor X Binding Attenuates Sepsis-Induced Respiratory and Renal Failure," *Am. J. Physiol. Cell. Mol. Physiol.* 290(1, pt. 1):L21-L31.

Wen Jinghai et al. (2001). "Antibody-Dependent Cellular Cytotoxicity and Antibody Dependent Cellular Phagocytosis of Breast Cancer Cells Mediated by Anti-Tissue Factor Monoclonal Antibodies," *FASEB Journal* 15(5):A1198. Annual Meeting of the Federation of American Societies for Experimental Biology on Experimental Biol; Orlando, Florida, Mar. 31-Apr. 4, 2001 Abstract.

Wiiger et al. (2000). "Effects of Binding of Ligand (FVIIa) to Induced Factor in Human Endothelial Cells," *Thrombosis Research* 98:311-321.

Written Opinion mailed on Oct. 7, 2004, for PCT Application No. PCT/US02/34727, filed on Oct. 29, 2002, five pages.

Wulfing, C. et al. (Oct. 7, 1994). "Correctly Folded T-Cell Receptor Fragments in the Periplasm of *Escherichia coli*. Influence of Folding Catalysts," *Journal of Molecular Biology* 242(5):655-669.

Yamashita, H. et al. (e-pub. Oct. 25, 2006). "Tissue Factor Expression Is a Clinical Indicator of Lymphatic Metastasis and Poor Prognosis in Gastric Cancer with Intestinal Phenotype," *J. Surg. Oncol.* pp. 1-8.

Zeher, M. et al. (May 1994). "Fibrinolysis-Resistant Fibrin Deposits in Minor Labial Salivary Glands of Patients with Sjogren's Syndrome," *Clinical Immunology and Immunopathology* 71(2):149-155.

Non-Final Office Action mailed Jul. 26, 2010, for U.S. Appl. No. 12/036,188, filed Feb. 22, 2008, 12 pages.

Non-Final Office Action mailed Sep. 9, 2010, for U.S. Appl. No. 12/404,256, filed Mar. 13, 2009, eight pages.

Taylor, F.B. Jr. et al. (Mar. 1991). "Lethal *E. coli* Septic Shock is Prevented by Blocking Tissue Factor with Monoclonal Antibody," *Circ. Shock* 33(3):127-134.

CDR REGIONS UNDERLINED (single underline for nucleic acid sequence and double underline for amino acid sequence).

H36.D3.B7 Anti-Tissue Factor Light Chain Variable Domain

GACATTCAGATGACCCAGTCTCCCAGTCTCCTGCCTCCCAGTCTCCTGCATCTCTGGGAGAAAGTGTCACCATCACATGC
 D  I  Q  M  T  Q  S  P  A  S  Q  S  A  S  L  G  E  S  V  T  I  T  C

CTGGCAAGTCAGACCATTGATACATGGTTAGCATGGTATCAGCAGAAACCAGGAAATCTCCTCAGTC
 L  A  S  <u>Q  T  I  D  T  W  L  A</u>  W  Y  Q  Q  K  P  G  K  S  P  Q  L

CTGATTATGCTGCCACCAACTTGGCAGATGGGGTCCCATCAAGGTTCAGTGGCAGTGGATCTGGCACA
 L  I  Y  <u>A  A  T  N  L  A  D</u>  G  V  P  S  R  F  S  G  S  G  S  G  T

AAATTTCTTTCAAGATCAGCAGCCTACAGGCTGAAGATTTTGTAAATTATTACTGTCAACAAGTTTAC
 K  F  S  F  K  I  S  S  L  Q  A  E  D  F  V  N  Y  Y  C  <u>Q  Q  V  Y</u>

AGTTCTCCATTCACGTTCGGTGCTGGGACCAAGCTGGAGCTGAAA
 <u>S  S  P  F  T</u>  F  G  A  G  T  K  L  E  L  K

FIG. 1A

H36.D3.B7 Anti-Tissue Factor Heavy Chain Variable Domain

```
GAGATCCAGCTGCAGCAGTCTGGGGGAGGCTTGGTGAAGCCTGGAGGGTCCCTTCAGTGCAGGTATCCTGCAAG
 E  I  Q  L  Q  Q  S  G  P  E  L  V  K  P  G  A  S  V  Q  V  S  C  K

ACTTCTGGTTACTCATTCATTCACTGACTACAACGTGTACTGGGTGAGGCAGAGCCATGGAAAGAGCCTTGAG
 T  S  G  Y  S  F  T  D  Y  N  V  Y  W  V  R  Q  S  H  G  K  S  L  E

TGGATTGGATATATTGATCCTTACAATGGTATTACTATCTACGACCAGAACTTCAAGGGCAAGGCCACA
 W  I  G  Y  I  D  P  Y  N  G  I  T  I  Y  D  Q  N  F  K  G  K  A  T

TTGACTGTTGACAAGTCTTCCACAGCCTTCATGCATCTCAACAGCCTGACATCTGACGACTCTGCA
 L  T  V  D  K  S  S  T  A  F  M  H  L  N  S  L  T  S  D  D  S  A

GTTTATTTCTGTGCAAGAGATGTGACTACGGCCCTTGACTTCTGGGGCCAAGGCACCACTCTCACAGTC
 V  Y  F  C  A  R  D  V  T  T  A  L  D  F  W  G  Q  G  T  T  L  T  V

TCCTCA
 S  S
```

FIG. 1B

HC Cloning Vector

HC Expression Vector

HC Cloning Vector

HC Expression Vector

LC Cloning Vector

LC Expression Vector

| FR1 (23 AA) | FR2 (15 AA) | CDR2 | FR3 (32 AA) | | FR4 (10 AA) | Names |
|---|---|---|---|---|---|---|
| 1 10 20 | 35 | 49 57 | 60 70 | 80 88 | 98 107 | |
| DIQMTQSPASQSASLGESVTITC | WYQQKPGKSPQLLIY | | GVPSRFSGSGSGTKFSFKISSLQAEDFVNYYC | | FGAGTKLEIK | CH36-LC |
| DIQMTQSPASQSASLGESVTITC | WYQQKPGKSPQLLIY | | GVPSRFSGSGSGTKFSFKISSLQAEDFVNYYC | | FGAGTKLEIK | LC-03 |
| DIQMTQSPASQSASLGESVTITC | WYLQKPGKSPQLLIY | | GVPSRFSGSGSGTKFSFKISSLQAEDFVNYYC | | FGAGTKLEIK | LC-04 |
| DIQMTQSPASLSASVGDRVTITC | WYLQKPGKSPQLLIY | | GVPSRFSGSGSGTKFSFKISSLQAEDFVNYYC | | FGQGTKLEIK | LC-05 |
| DIQMTQSPASQSASLGESVTITC | WYLQKPGKSPQLLIY | | GVPSRFSGSGSGTKFSFKISSLQAEDFVNYYC | | FGQGTKLEIK | LC-06 |
| DIQMTQSPASQSASLGESVTITC | WYLQKPGKSPQLLIY | | GVPSRFSGSGSGTDFSFTISSLQPEDFATYYC | | FGQGTKLEIK | LC-07 |
| DIQMTQSPASQSASLGESVTITC | WYLQKPGKSPQLLIY | | GVPSRFSGSGSGTDFSFTISSLQPEDFATYYC | | FGQGTKLEIK | LC-08 |
| DIQMTQSPASLSASVGDRVTITC | WYLQKPGKSPQLLIY | | GVPSRFSGSGSGTDFSFTISSLQPEDFATYYC | | FGQGTKLEIK | LC-09 |
| DIQMTQSPASLSASVGDRVTITC | WYLQKPGKSPQLLIY | | GVPSRFSGSGSGTDFSFTISSLQPEDFANYYC | | FGQGTKLEIK | LC-10 |
| DIQMTQSPASLSASVGDRVTITC | WYLQKPGKSPQLLIY | | GVPSRFSGSGSGTKFSFTISSLQPEDFANYYC | | FGQGTKLEIK | LC-11 |
| DIQMTQSPASLSASVGDRVTITC | WYLQKPGQSPQLLIY | | GVPSRFSGSGSGTKFSFTISSLQPEDFANYYC | | FGQGTKLEIK | LC-12 |

Fig. 6A

Light Chain CDR Sequnces of CH36

| CDR1 (11 AA) | | CDR2 (7 AA) | | CDR3 (9 AA) | |
|---|---|---|---|---|---|
| 24 34 | | 50 56 | | 89 97 | |
| L A S Q T I D T W L A | | A A T N L A D | | Q Q V Y S S P F T | |

| FR1 (30 AA) | FR2 (14 AA) | FR3 (32 AA) | FR4 (11 AA) | Names |
|---|---|---|---|---|
| 1          10          20          30 | 36          49 | 67          75          85          95 | 107          117 | |
| EIQLQQSGPELVKPGASVQVSCKTSGYSFT | WVRQSHGKSLEWIG | KATLTVDKSSTTAFMHLNSLTSDDSAVYFCAR | WGQGTTLTVSS | cH36-HC |
| QIQLQQSGPELVKPGASVQVSCKTSGYSFT | WVRQSHGKSLEWIG | KATLTVDKSSTTAFMHLNSLTSDDSAVYFCAR | WGQGTTVTVSS | HC-01 |
| QIQLQQSGPELVKPGASVQVSCKTSGYSFT | WVRQSPGKGLEWIG | KATLTVDKSSTTAFMHLNSLTSDDSAVYFCAR | WGQGTTVTVSS | HC-02 |
| QIQLQQSGPELVKPGASVQVSCKTSGYSFT | WVRQSPGKGLEWIG | KATLTVDKSSTTAFMHLNSLRSEDTAVYFCAR | WGQGTTVTVSS | HC-03 |
| QIQLQQSGPELVKPGASVQVSCKTSGYSFT | WVRQSPGKGLEWIG | KATLTVDKSSTTAFMELSSLRSEDTAVYFCAR | WGQGTTVTVSS | HC-04 |
| QIQLQQSGPELVKPGASVQVSCKTSGYSFT | WVRQSPGKGLEWIG | KATLTVDKSTSTAYMELSSLRSEDTAVYFCAR | WGQGTTVTVSS | HC-05 |
| QMQLQQSGGELVKPGASVQVSCKTSGYSFT | WVRQSPGKGLEWIG | KATLTVDKSTSTAYMELSSLRSEDTAVYFCAR | WGQGTTVTVSS | HC-06 |
| QIQLVQSGGELVKPGGSVQVSCKTSGYSFT | WVRQSPGKGLEWIG | KATLTVDKSTSTAYMELSSLRSEDTAVYFCAR | WGQGTTVTVSS | HC-07 |
| QIQLVQSGGEVKPGEVKKPGASVQVSCKTSGYSFT | WVRQSPGKGLEWIG | KATLTVDKSTSTAYMELSSLRSEDTAVYFCAR | WGQGTTVTVSS | HC-08 |
| QIQLVQSGPEVKPGASVRVSCKASGYSFT | WVRQSPGKGLEWIG | KATLTVDKSTSTAYMELSSLRSEDTAVYFCAR | WGQGTTVTVSS | HC-08R1 |
| QIQLVQSGPELKPGASVRVSCKASGYSFT | WVRQSPGKGLEWIG | KATLTVDKSTSTAYMELSSLRSEDTAVYFCAR | WGQGTTVTVSS | HC-11 |
| QIQLVQSGPELVKPGASVRVSCKASGYSFT | WVRQSPGKGLEWIG | KATLTVDKSTSTAYMELSSLRSEDTAVYFCAR | WGQGTTVTVSS | HC-12 |
| QIQLVQSGPELVKPGASVRVSCKASGYSFT | WVRQSPGKGLEWIG | KATLTVDKSTSTAYMELSSLRSEDTAVYFCAR | WGQGTTVTVSS | HC-09 |
| QIQLVQSGPEVVKPGASVRVSCKASGYSFT | WVRQSPGKGLEWIG | KATLTVDKSTSTAYMELSSLRSEDTAVYFCAR | WGQGTTVTVSS | HC-10 |

Fig. 7A

Heavy Chain CDR Sequences:

| CDR1 (5 aa) | | CDR2 (17 AA) | | CDR3 (8AA) | | Names |
|---|---|---|---|---|---|---|
| 31 | 35 | 50 | 66 | 99 | 106 | |
| D Y N V Y | | Y I D P Y N G I T I Y D Q N F K G | | D V T T A L D F | | CH36 |
| D Y N V Y | | Y I D P Y N G I T I Y D Q N L K G | | D V T T A L D F | | HC-08 |

Sequence of human kappa Light Chain Constant Domain:

RTVAAPSVFIFPPSDEQLKSGTASVVCLLNNFYPREAKVQWKVDNALQSGNSQESVTEQDSKDSTYSLSSTLTLSKADYEKH
KVYACEVTHQGLSSPVTKSFNRGEC

Fig. 8A

Sequence of human IgG1 Heavy Chain Constant Domain:

EFASTKGPSVFPLAPSSKSTSGGTAALGCLVKDYFPEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLSLSPGK

Fig. 8B

Sequence of human kappa Light Chain Constant Domain:

RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC

Fig. 9A

Sequence of human IgG4 Heavy Chain Constant Domain:

EFASTKGPSVFPLAPCSRSTSESTAALGCLVKDYFPEPVTVSWNSGALTSGVHTFPAVLQSSGLYSLSSVVTVPSSSLGTKTY
TCNVDHKPSNTKVDKRVESKYGPPCPSCPAPEFLGGPSVFLFPPKPKDTLMISRTPEVTCVVVDVSQEDPEVQFNWYVDGV
EVHNAKTKPREEQFNSTYRVVSVLTVLHQDWLNGKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKSRWQEGNVFSCSVMHEALHNHYTQKSLSLSLGK

Fig. 9B

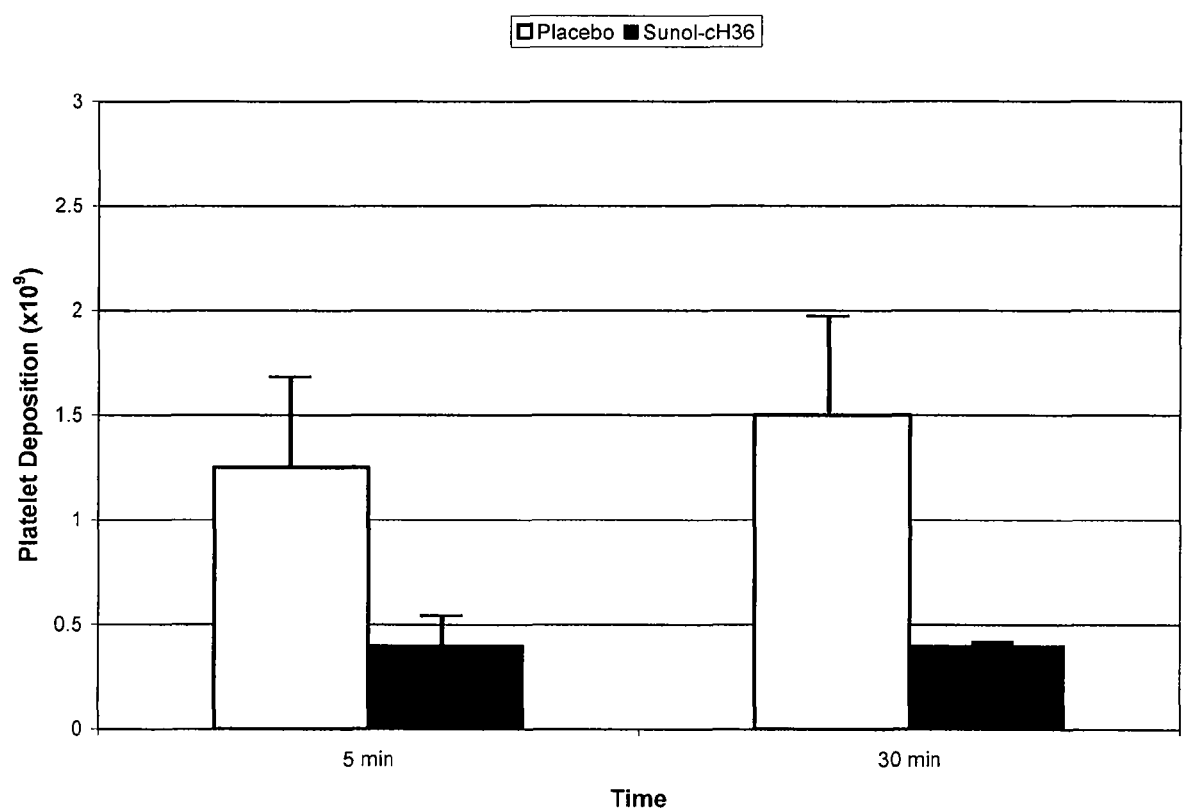
Fig. 10. Platelet Deposition in Endarterectomized Chimpanzees

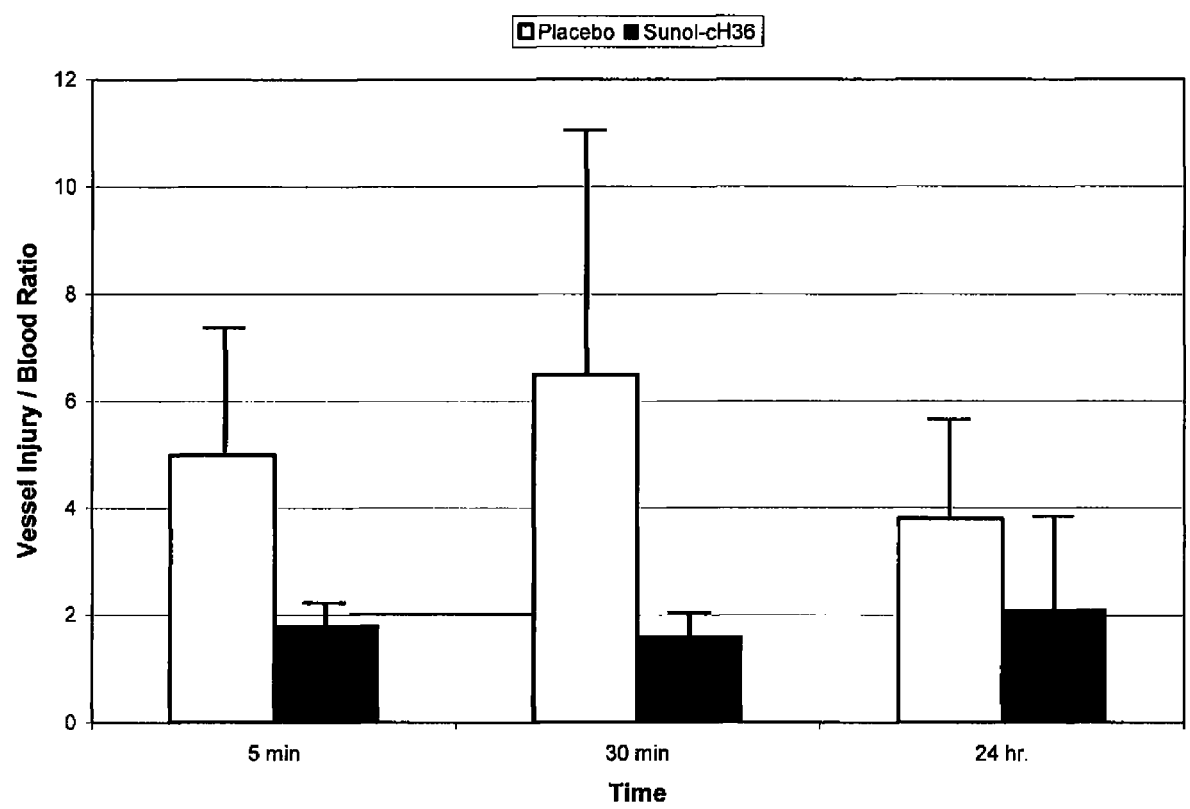
Fig. 11. Vessel Injury / Blood Ratios in Endarterectomized Chimpanzees

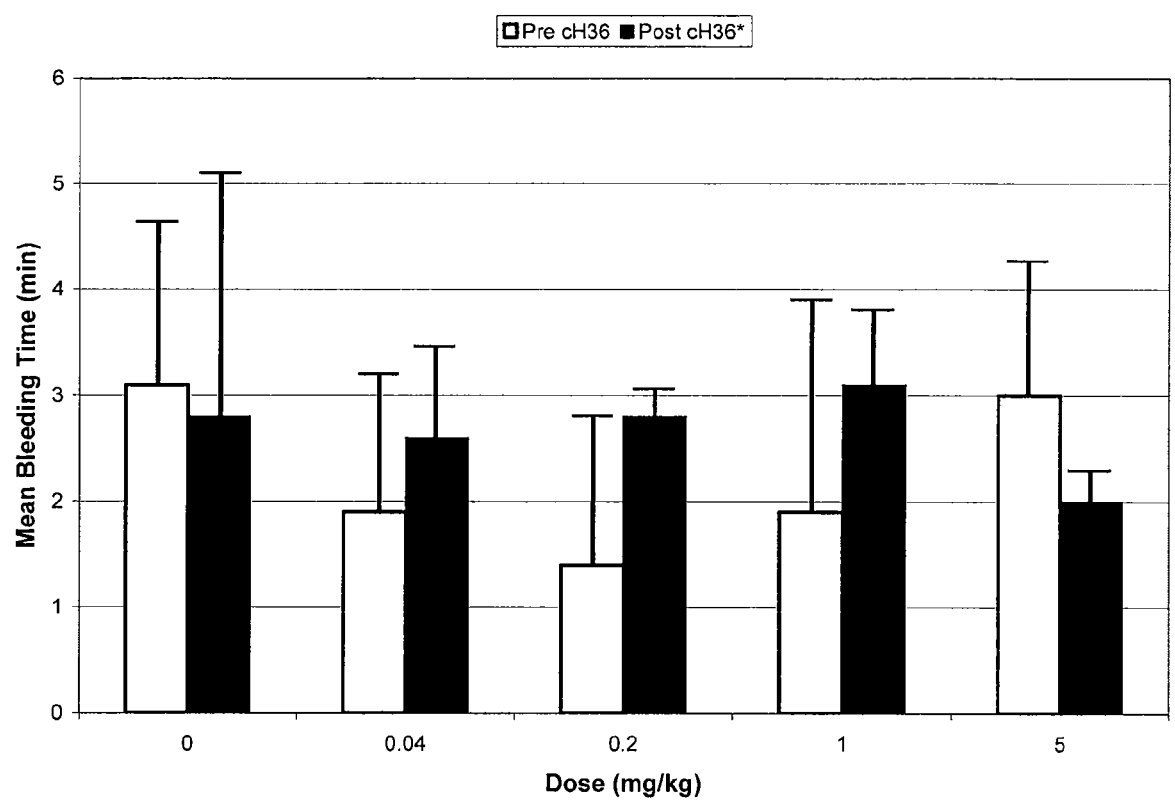
Fig. 12. Mean Bleeding Times

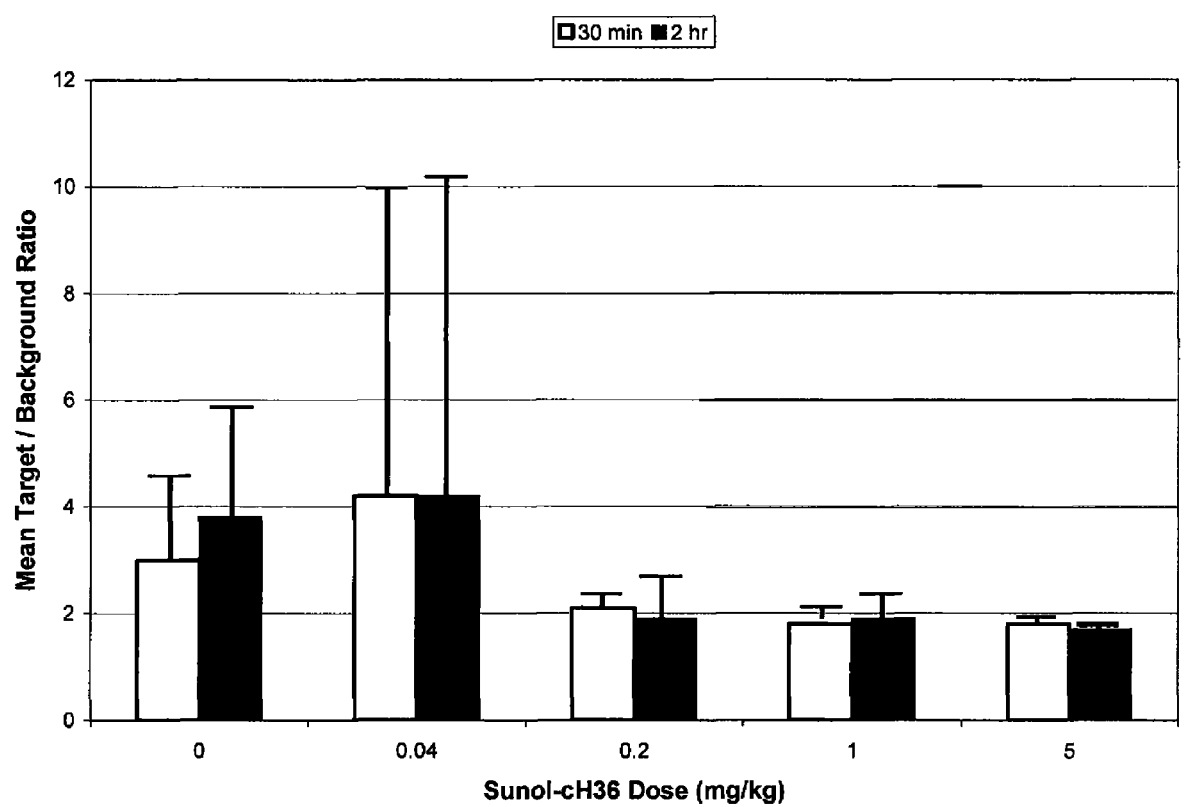
Fig. 13. Mean Target / Background Ratio for $^{111}$In-Platelet Deposition

USE OF ANTI-TISSUE FACTOR ANTIBODIES FOR TREATING THROMBOSES

CROSS-REFERENCE TO RELATED APPLICATIONS

The present application is a divisional patent application of U.S. application Ser. No. 10/310,113, filed Dec. 4, 2002, which is a continuation-in-part of U.S. application Ser. No. 09/990,586 entitled Antibodies For Inhibiting Blood Coagulation and Methods of Use Thereof by Jiao, J. et al. as filed on Nov. 21, 2001, which application claims priority to U.S. Provisional Application U.S. Ser. No. 60/343,306 as filed on Oct. 29, 2001. The disclosures of said U.S. application Ser. Nos. 10/310,113, 09/990,586; and 60/343,306; are each incorporated herein by reference.

BACKGROUND OF THE INVENTION

1. Field of the Invention

The present invention relates to novel human tissue factor antibodies and methods of using the antibodies to inhibit tissue factor-related functions such as blood coagulation, angiogenesis, tumor growth and metastasis, and inflammation. In particular, the invention relates to novel antibodies that can specifically bind native human tissue factor with high affinity and prevent factor X or factor IX binding and activation. The antibodies of the invention are useful for a variety of applications, particularly for reducing thrombosis in vivo.

2. Background

Blood clotting assists homeostasis by minimizing blood loss. Generally, blood clotting requires vessel damage, platelet aggregation, activation of coagulation factors, and inhibition of fibrinolysis. The coagulation factors act through a cascade that relates the vessel damage to formation of a blood clot (see generally L. Stryer, *Biochemistry*, 3rd Ed, W.H. Freeman Co., New York; and A. G. Gilman et al., *The Pharmacological Basis of Therapeutics*, 8th Edition, McGraw Hill Inc., New York, pp. 1311-1331).

There is general agreement that factor X (FX) activation to factor Xa (FXa) (or factor IX activation to factor IXa) is a critical step in the blood coagulation process. Generally, FX (or FIX) is converted to FXa (or FIXa) by binding a catalytically active complex that includes "tissue factor" (TF). TF is a controllably-expressed cell membrane protein that binds factor VII/VIIa (FVII/FVIIa) to produce the catalytically active complex (TF:FVIIa). A blood clot follows FXa-mediated activation of prothrombin to thrombin, which then converts fibrinogen to fibrin and activates platelets. Blood clotting can be minimized by inactivation of TF to non-native forms which cannot optimally produce the TF:FVIIa complex. Excessive activation of the coagulation cascade through formation of FXa (or FIXa) by TF:FVIIa complex is believed to contribute to various thromboses including restenosis.

Thrombosis may be associated with invasive medical procedures including but not limited to cardiac surgery (e.g. angioplasty), abdominothoracic surgery, arterial surgery, peripheral vascular bypass grafts or coronary artery bypass grafts, deployment of an implementation (e.g., a stent or catheter), arterio-venous shunts or fistulas, reconstructive or plastic surgery or endarterectomy. Further, thrombosis may accompany various thromboembolic disorders and coagulopathies such as stroke, pulmonary embolism (e.g., atrial fibrillation with embolization), coronary artery disease or acute coronary syndromes (e.g., unstable angina or myocardial infarction), atherosclerosis or other thrombo-occlusive disorders, deep vein thrombosis and disseminated intravascular coagulation, etc. Manipulation of body fluids can also result in an undesirable thrombus, particularly in blood transfusions or fluid sampling, as well as procedures involving extracorporeal circulation (e.g., cardiopulmonary bypass surgery) and renal dialysis.

More generally, thromboses particularly amenable to prevention or treatment include those associated with cardiovascular disease, for instance, coronary artery disease, acute coronary syndrome, and atherosclerosis. Other particular thromboses include those associated with angioplasty or restenosis.

Anti-coagulants are frequently used to alleviate or avoid blood clots associated with thrombosis. Blood clotting often can be minimized or eliminated by administering a suitable anti-coagulant or mixture thereof, including one or more of a coumarin derivative (e.g., warfarin, Coumadin or dicumarol) or a charged polymer (e.g., heparin, low molecular weight heparin, pentosan, hirudin or hirulog) or anti-platelet agents (e.g., ReoPro, Integrilin, Aggrestat, Plavix, Ticlid or aspirin). See e.g., Gilman et al., supra, R. J. Beigering et al., *Ann. Hematol.*, 72:177 (1996); J. D. Willerson, *Circulation*, 94:866 (1996).

However, use of anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Certain antibodies with anti-platelet activity have also been used to alleviate various thromboses. For example, ReoPro® is a therapeutic antibody fragment that is routinely administered to alleviate various thromboembolic disorders such as those arising from angioplasty, myocardial infarction, unstable angina and coronary artery stenoses. Additionally, ReoPro® can be used as a prophylactic to reduce the risk of myocardial infarction and angina (J. T. Willerson, *Circulation*, 94:866 (1996); M. L. Simmons et al., *Circulation*, 89:596 (1994)).

Certain anti-coagulant antibodies are also known. Particularly, certain TF-binding antibodies have been reported to inhibit blood coagulation, presumably by interfering with assembly of a catalytically active TF:FVIIa complex (see e.g., Jeske et al., *SEM in THROM. and HEMO*, 22:213 (1996); Ragni et al., *Circulation*, 93:1913 (1996); European Patent No. 0 420 937 B1; W. Ruf et al., *Throm. Haemost.*, 66:529 (1991); M. M. Fiorie et al., *Blood*, 8:3127 (1992)).

However, current TF-binding antibodies exhibit significant disadvantages which can minimize their suitably as anti-coagulants. For example, current TF-binding antibodies do not exhibit sufficient binding affinity for optimal anti-coagulant activity. Accordingly, for many thrombotic conditions, to compensate for such ineffective binding affinities, unacceptably high antibody levels must be administered to minimize blood coagulation.

It would thus be desirable to have an anti-coagulant antibody that binds native human TF with high affinity and selectivity to thereby inhibit undesired blood coagulation and the formation of blood clots. It would be further desirable to have such an anti-coagulant antibody that prevents the binding of factor X (or factor IX) to TF:FVIIa complex.

SUMMARY OF THE INVENTION

The present invention features methods for preventing or treating thrombosis in a mammal. In general, the invention methods feature use of humanized immunoglobins including partially humanized antibodies such as chimeric antibodies.

Also envisioned are use of fragments of such immunoglobins, preferably those that bind tissue factor (TF) specifically. Practice of the invention has a variety of important uses including reducing potentially life-threatening vascular thromboses in primates and especially human subjects.

Particular methods of the invention help prevent or treat one or a combination of vascular thromboses, particularly those impacting arteries and associated vasculature. Additionally preferred methods help to maintain vessel patency often without significantly impairing homeostatic function. Preferred use of the invention provides an especially effective means to block thrombosis at the initial stage of the blood coagulation cascade. Internal bleeding complications often associated with standard anti-thrombotic therapies is reduced or avoided by the invention.

Accordingly, and in one aspect, the invention provides a method for preventing or treating a thrombosis in the mammal. In one embodiment, the method includes administering to the mammal a therapeutically effective amount of at least one humanized antibody, chimeric antibody; or fragment of such antibodies that binds specifically to human TF. Preferred binding forms a specific complex in which factor X or factor IX binding thereto and the FX or FIX activation by TF:VIIa are inhibited. Preferred administration of the humanized antibodies, chimeric antibodies and fragments are sufficient to prevent or treat one or more thromboses in the mammal.

In another aspect, the invention provides a method for performing plastic, reconstructive, or transplant surgery in the mammal. In one embodiment, the method includes introducing a graft into the mammal and contacting the graft with a therapeutically effective amount of at least one humanized antibody, chimeric antibody, or fragment of the humanized antibody or chimeric antibody that binds specifically to human TF to form a specific binding complex. Typical contact with the graft is generally sufficient to maintain or increase patency of the graft as determined by conventional methods such as inspection.

Particular humanized antibodies for use with the invention can be monoclonal. Most specifically bind a conformational epitope predominant to native human TF, usually with strong binding affinity. Indeed, preferred humanized antibodies of the invention bind to native human TF at least about 5 times greater, more typically at least about ten times greater than the binding affinity exhibited by certain current anti-TF antibodies (see e.g., Jeske et al., *SEM in THROM and HEMO,* 22:213 (1996); Ragni et al., *Circulation,* 93:1913 (1996); European Patent No. 0 420 937 B1; W. Rufetal., *Throm. Haemost.,* 66:529 (1991); M. M. Fiorie et al., *Blood,* 8:3127 (1992)). Additionally, preferred humanized antibodies of the invention are specific for native human TF, and do not substantially bind non-native or denatured TF.

Additionally preferred humanized antibodies, chimeric antibodies, and fragments thereof include at least one hypervariable region from a murine monoclonal antibody, preferably the H36.D2.B7 monoclonal (secreted by hybridoma ATCC HB-12255 and often referred to as H36). More preferred humanized immunoglobins and fragments for use with the invention include multiple hypervariable regions of the H36.D2.B7 antibody including all of same. Specifically preferred antibodies for use with the invention have a binding specificity for the TF about equal or greater than the antibody obtained from the ATCC deposited cell line H36.D2.B7. Nucleic acid and amino acid sequences (SEQ ID:NOS 1-4) of the hypervariable regions of the murine H36.D2.B7 antibody are set forth in FIGS. 1A and 1B.

Practice of the invention is compatible with use of a wide variety of immunoglobins, specifically humanized antibodies, humanized chimeric antibodies and fragments of such antibodies that bind human TF specifically. Preferably, substantially of the immunoglobin outside of the hypervariable region is humanized although less humanization (or more) may be desirable for some applications. For instance, FIGS. 6A-D and 13A-D show sequences of partially and fully humanized light (LC) and heavy chain (HC) variable regions of antibodies well suite for use with the present invention. FIGS. 8A-B and 9A-B show drawings of preferred humanized antibody constant regions.

In preferred aspects, the invention methods prevent or treat thrombosis in the mammal and may also desirably inhibit blood coagulation and blood clot formation, as well as reduce levels of unwanted TF in the mammal.

The invention has a wide variety of uses and finds particular use in the prevention or treatment of various thromboses, particularly to prevent or inhibit restenosis, or other thromboses. Such indications can follow an invasive medical procedure such as arterial or cardiac surgery (e.g., angioplasty). However, the invention is additionally employed to reduce or even effectively eliminate thrombotic occlusion arising from activation of blood coagulation in such non-surgical cardiovascular conditions including but not limited to coronary artery disease, acute coronary syndromes (e.g., unstable angina and myocardial infarction) and atherosclerosis. The invention also can be used to reduce or even effectively eliminate blood coagulation arising from use of a medical implementation (e.g., a catheter, stent or other medical device). Preferred invention methods are generally compatible with many anti-coagulant, anti-platelet and thrombolytic therapies, thereby allowing administration in a cocktail format, for instance, to boost or prolong inhibition of blood coagulation and thrombus formation.

The invention methods provided herein can also be employed to assist anti-thrombosis efforts by helping to decrease coagulation potential in the extracorporeal circulation of a mammal such as a primate and particularly a human subject. In such methods, one or more antibodies disclosed herein can be administered to the mammal in an amount sufficient to inhibit blood coagulation prior to or during extracorporeal circulation such as may occur with cardiopulmonary bypass surgery, organ transplant surgery or other prolonged surgeries.

In another aspect, the invention provides a kit for performing the methods described herein. A particular kit includes at least one humanized antibody, chimeric antibody, or fragment thereof that binds specifically to human tissue factor (TF) to form a complex.

Other aspects of the invention are discussed infra.

BRIEF DESCRIPTION OF THE DRAWINGS

FIGS. 1A and 1B shows the nucleic acid (SEQ ID NOS:1 and 3) and amino acid (SEQ ID NOS:2 and 4) sequences of light chain and heavy chain variable regions of H36.D2.B7 with hypervariable regions (CDRs or Complementarity Determining Regions) underlined (single underline for nucleic acid sequences and double underline for amino acid sequences).

FIGS. 6A-D are drawings showing sequences of partially and fully humanized light chain (LC) variable regions. FIG. 6A sequences correspond to SEQ ID NOS: 11, 68-77, 12, 78-87, 15, 88-97, 16, and 98-107, respectively, in order of appearance. Light chain CDR sequences of cH36 are shown in FIGS. 6B-D (SEQ ID NO: 170, SEQ ID NO: 6 and SEQ ID NO: 7, respectively). Sequence named "LC-09" is representative of a fully humanized LC framework region. Immediately following the last residue of the framework 4 (FR4) variable domain is the first residue of the constant domain for hOAT or hFAT.

FIGS. 7A-D are sequences of partially and fully humanized heavy chain (LC) variable regions. FIG. 7A sequences correspond to SEQ ID NOS: 19, 108-120, 20, 121-133, 23, 134-146, 24, and 147-159, respectively, in order of appearance. Heavy chain CDR sequences for cH36 and HC-08 are shown in FIGS. 7B-D (SEQ ID NO: 160, 163, 161, 164, 162, and 165, respectively, in order of appearance. Sequence named "HC-08" is fully humanized HC framework region. Except for HC-08, all other HC mutants and cH36 contain F at position 64 in CDR2. HC-08 has the mutation F64 to L (change from F to L at position 64). Immediately following the last residue of the framework 4 (FR4) variable domain is the first residue of the constant domain for OAT or FAT. LC constant are the same for hOAT and hFAT.

FIGS. 8A-B (SEQ ID NOS: 166 and 167, respectively, in order of appearance) are drawings showing humanized IgG1 anti-tissue factor antibody (hOAT (IgG1) constant regions.

FIGS. 9A-B (SEQ ID NOS: 168 and 169, respectively, in order of appearance) are drawings showing humanized IgG four anti-tissue factor antibody (hFAT) (IgG4) constant regions. Immediately following the last residue of the framework 4 (FR4) variable domain is the first residue of the constant domain for hOAT or hFAT. LC constant domain is the same for hOAT and hFAT.

FIG. 10 is a graph showing platelet deposition in endarterectomized chimpanzees

FIG. 11 is a graph showing vessel injury/blood ratios in endarterectomized chimpanzees FIG. 12 is a graph showing mean bleeding times in an angioplasty study performed in cynomolgus monkeys. Post cH36 represents the mean (with standard deviation) of all bleeding time determinations taken at 1.5 or 4 hours after administration of cH36.

FIG. 13 is a graph showing mean target/background ratio for $^{111}$In-Platelet Deposition.

DETAILED DESCRIPTION OF THE INVENTION

Figures 2A, 2B:
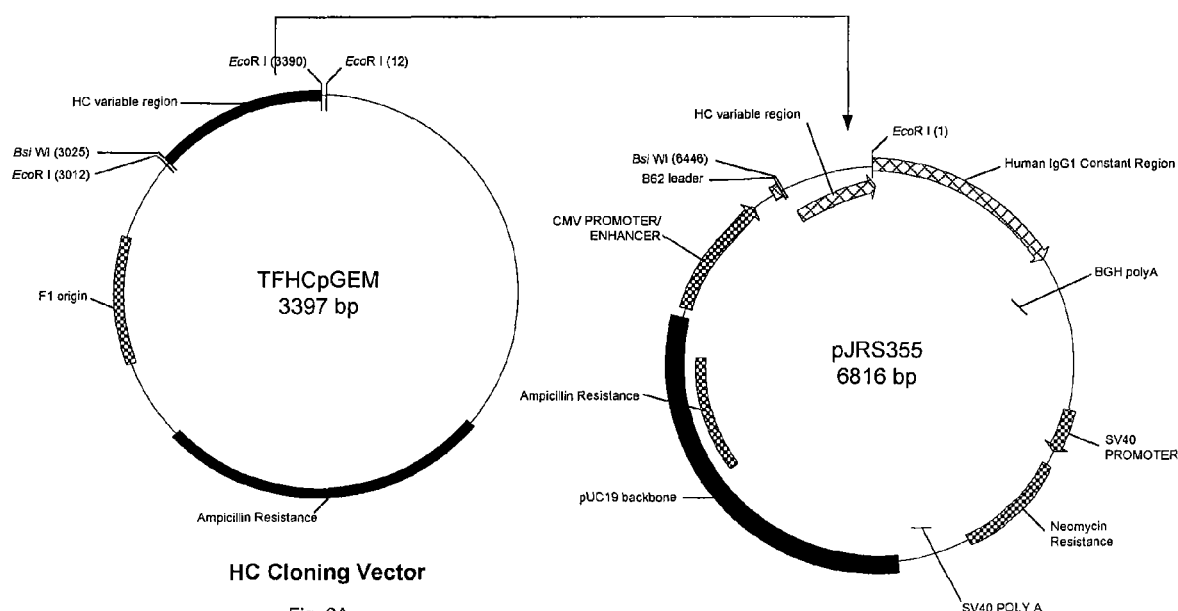
FIGS. 2A-B are drawings showing human IgG1-cH36 HC variable region cloning and expression vectors. HC cloning vector (2A) and HC expression vector (2B).

As discussed above, the invention provides a method for preventing or treating thrombosis in a mammal that includes administering to the mammal a therapeutically effective amount of at least one humanized immunoglobin, typically a humanized antibody; chimeric antibody, or fragment of the humanized antibody or chimeric antibody that binds specifically to human TF (free or in complex with FVIIa or FVII) to form a complex. Preferably, factor X or factor IX binding to the TF-antibody complex and the FX or FIX activation by TF:VIIa are inhibited.

Thus in one embodiment, the invention provides a method for preventing or treating a thrombosis in a mammal and particularly a primate such as a human subject. A preferred method involves administering to the mammal a therapeutically effective amount of at least one humanized antibody, chimeric antibody, or fragment thereof that binds specifically to human TF (free or in complex with FVIIa or FVII) to form a complex in which factor X or factor IX binding to the complex and the FX or FIX activation by TF:VIIa are inhibited. Preferred administration routes are sufficient to prevent or treat the thrombosis in the mammal.

Preferably, the humanized antibody, humanized chimeric antibody or the fragment of the antibody or chimera for use with the invention exhibits at least one of: 1) a dissociation constant ($K_d$) for the TF of less than about 0.5 nM; and 2) an affinity constant ($K_a$) for the TF of less than about $2 \times 10^9$ M$^{-1}$. An example of a preferred CDR for inclusion in the humanized immunoglobins is one derived from the murine monoclonal antibody designated H36.D2.B7 (secreted by hybridoma ATCC HB-12255 and often referred to as H36). See FIGS. 1A and 1B, for instance as well U.S. Pat. No. 5,986,065 and the PCT Application No. PCT/US98/04644 (WO 98/40408).

More particular antibody or chimeric fragments for use with the invention will have a molecular weight of at least about 40,000 daltons for Fab and about 80,000 daltons for Fab(2)', preferably between from about 45,000 daltons to about 52,000 daltons for Fab, and between from about 90,000 daltons to about 104,000 daltons for Fab(2)', more preferably about 50,000 for Fab and 100,000 for Fab(2)' as determined by routine protein sizing assays such as gel electrophoresis.

By the phrase "humanized" is meant an immunoglobin (typically an antibody) that includes a human framework region and one or more CDRs from a non-human source, usually rodent such as a rat or mouse immunoglobin. The non-human antibody providing the CDRs is called a "donor" and the human immunoglobin called the "acceptor". Constant regions need not be present, as in, for example, certain TF binding fragments of such immunoglobins. Preferred constant regions, if present, are substantially identical to human immunoglobin constant regions i.e., at least about 90% identical with regard to the amino acid sequence, preferably at least about 95% identical or greater. Accordingly, nearly all parts of the humanized immunoglobin, with the possible exception of the CDRs, are substantially identical to corresponding parts of naturally-occurring human immunoglobin sequences.

By the phrase "humanized antibody" is meant an antibody that includes a humanized light chain and a humanized heavy chain immunoglobin. Also included are partially humanized (chimeric) antibodies and fragments of chimeric and non-chimeric antibodies that bind TF specifically. Methods for making and using such antibodies have been disclosed, for example, in the U.S. application Ser. No. 09/990,586 entitled *Antibodies For Inhibiting Blood Coagulation and Methods of Use Thereof* by Jiao, J. et al.; U.S. Provisional Application No. 60/343,306 and U.S. Ser. No. 10/230,880 entitled *Method of Humanizing Immune System Molecules* as filed on Aug. 29, 2002.

As discussed throughout the U.S. Pat. No. 5,986,065 and the PCT Application No. PCT/US98/04644 (WO 98/40408), antibodies that include the preferred CDRs of the murine H36.D2.B7 antibody typically exhibit substantial affinity for native human TF. In particular, such antibodies exhibit an association constant ($K_a$, M$^{-1}$) for native human TF of at least about $1 \times 10^8$ M$^{-1}$ as determined by surface plasmon analysis (particularly, BIACore analysis in accordance with the procedures of the U.S. Pat. No. 5,986,065; and WO 98/40408 which has been disclosed), more preferably at least about $5 \times 10^8$ M$^{-1}$ as determined by surface plasmon analysis, still more preferably a $K_a$ ($K_a$, $M^{-1}$) for native human TF of at least about $1 \times 10^{10}$ $M^{-1}$ as determined by surface plasmon resonance analysis.

As also discussed throughout the U.S. Pat. No. 5,986,065 and the PCT Application No. PCT/US98/04644 (WO 98/40408), antibodies that include such preferred CDRs particularly bind with TF so that FX (or FIX) does not effectively bind to the TF:FVIIa complex whereby FX (or FIX) is not effectively converted to its activated form (FXa or FIXa). Particularly preferred humanized antibodies will strongly inhibit FX activation by a TF:FVIIa complex, e.g. an inhibition of at least about 50%, more preferably at least about 80%, and even more preferably at least about 90% or 95%, even at low lipidated TF concentrations such as less than about 1.0 nM TF, or even less than about 0.20 nM or 0.10 nM TF, as determined by a standard in vitro binding assay (described fully in the WO 98/40408 and the U.S. Pat. No. 5,986,065).

By the phrase "chimeric antibody" or related phrase including plural forms is meant antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as γ ($\gamma_1, \gamma_2, \gamma_3$, or $\gamma_4$). A typical therapeutic chimeric antibody is thus a hybrid protein consisting of the V or antigen-binding domain from a mouse antibody and the C or effector domain from a human antibody, although other mammalian species may be used. A specifically preferred chimeric antibody is the cH36 mouse-human chimera disclosed herein.

The humanized antibodies of the present invention can be polyclonal or monoclonal, as needed, and may have an IgG1 or IgG4 isotype.

More particular murine immunoglobin hypervariable regions that are preferred antigen binding regions for many invention applications are shown in FIGS. 1A and 1B and SEQ ID NOS. 2 and 4). See also the WO 98/40408 application, for example.

Also preferred for use with the present invention methods are humanized antibodies, humanized chimeric antibodies and fragments of same that have at least one hypervariable region of a light chain variable region that has high sequence identity (at least 90% or 95% amino acid sequence identity) to or be the same as one, two or three of the corresponding hypervariable regions of the light chain variable region of H36.D2.B7 as shown in the FIGS. 1A and 1B as well as the PCT/US98/04644 (WO 98/40408). See in particular those hypervariable regions shown with underlining in FIG. 1A and are the following: 1) LASQTID (SEQ ID NO:5); 2) AATNLAD (SEQ ID NO:6); and 3) QQVYSSPFT (SEQ ID NO:7).

Especially preferred antibodies for use with the present invention will have one, two or three hypervariable regions of a heavy chain variable region that have high sequence identity (at least 90% or 95% amino acid sequence identity) to or be the same as one, two or three of the corresponding hypervariable regions of the heavy chain variable region of H36.D2.B7 (those hypervariable regions shown with underlining in FIG. 1B and are the following: 1) TDYNVY (SEQ ID NO:8); 2) YIDPYNGITIYDQNFKG (SEQ ID NO:9); and 3) DVTTALDF (SEQ ID NO:10). See also the PCT/US98/04644 (WO 98/40408) application.

Thus in an especially preferred invention embodiment, humanized antibodies, humanized chimeric antibodies, and fragments of same will be substantially the same as and preferably identical to the hypervariable regions of the murine H36.D2.B7 antibody.

Certain humanized chimeric antibodies are also suitable for use with the present invention, for example, antibody molecules that combine a non-human animal variable region and a human constant region, thereby rendering the antibodies less immunogenic in a human subject than the corresponding non-chimeric antibody. A variety of types of such chimeric antibodies can be prepared, including e.g. by producing human variable region chimeras, in which parts of the variable regions, especially conserved regions of the antigen-binding domain, are of human origin and only the hypervariable regions are of non-human origin. See the U.S. Pat. No. 5,986,065 and the PCT/US98/04644 (WO 98/40408) application. See also discussions of humanized chimeric antibodies and methods of producing same in S. L. Morrison, *Science*, 229:1202-1207 (1985); Oi et al., *BioTechniques*, 4:214 (1986); Teng et al., *Proc. Natl. Acad. Sci. U.S.A.*, 80:7308-7312 (1983); Kozbor et al., *Immunology Today*, 4:7279 (9183); Olsson et al., *Meth. Enzymol.*, 9:3-16 (1982). Additionally, transgenic mice can be employed. For example, transgenic mice carrying human antibody repertoires have been created which can be immunized with native human TF. Splenocytes from such immunized transgenic mice can then be used to create hybridomas that secrete human monoclonal antibodies that specifically react with native human TF as described above. See N. Lonberg et al., Nature, 368:856-859 (1994); L. L. Green et al., Nature Genet., 7:13-21 (1994); S. L. Morrison, *Proc. Natl. Acad. Sci. U.S.A.*, 81:6851-6855 (1994).

See the U.S. Pat. No. 5,986,065 and the PCT/US98/04644 (WO 98/40408) application for more information relating to making and using the murine H36.D2.B7 immunoglobin as well as related antibodies.

"Humanized antibody of the invention" or other similar term refers to humanized whole immunoglobulin as well as immunologically active fragments which bind native human TF. The humanized immunoglobulins and immunologically active fragments thereof include an epitope-binding site (i.e., a site or epitope capable of being specifically bound by an antibody recognizing native human TF). Exemplary antibody fragments include, for example, Fab, F(v), Fab', F(ab')$_2$ fragments, "half molecules" derived by reducing the disulfide bonds of immunoglobulins, single chain immunoglobulins, or other suitable antigen binding fragments (see e.g., Bird et al., *Science*, 242: 423-426 (1988); Huston et al., *PNAS*, (USA), 85:5879 (1988); Webber et al., *Mol. Immunol.*, 32:249 (1995)). The antibody or immunologically active fragment thereof may be of animal (e.g., a rodent such as a mouse or a rat), or chimeric form (see Morrison et al., *PNAS*, 81:6851 (1984); Jones et al., *Nature*, 321: 522 (1986)). Single chain antibodies can be preferred for some invention applications as well as TF binding fragments thereof.

By the phrase "specific binding" is meant that the humanized antibodies form a detectable binding complex with the TF and no other antigen as determined by standard immunological techniques such as RIA, Western blot or ELISA.

Typically preferred humanized antibodies for use with the invention have a binding specificity for tissue factor, preferably human TF, that is about equal or greater than the antibody obtained from H36.D2.B7 deposited under ATCC Accession No. HB-12255. Methods for determining binding specificity and affinity are known in the field and include specific assays described in the U.S. Pat. No. 5,986,065 and the PCT/US98/04644 (WO 98/40408) application, for instance.

As mentioned, it is an object of the present invention to provide effective methods for preventing, treating, delaying onset of or relieving symptoms associated with one or a combination of thromboses that can inflict a mammal.

In one embodiment, following about 5 minutes after administration of the humanized antibody, chimeric antibody or fragment, the mammal exhibits a blood clotting time of between from about 50 to about 350 seconds as determined by a standard prothrombin (PT) time assay. The standard PT assay is discussed below. See also Example 3 and the U.S. Pat. No. 5,986,065 and the PCT/US98/04644 (WO 98/40408) for related disclosure.

In another embodiment of the method, the amount of the administered humanized antibody, chimeric antibody, or fragment of the humanized antibody or chimera is sufficient to inhibit platelet deposition time by at least about 50% as determined by a standard platelet deposition assay, preferably at least about 70% or about 95%.

By the phrase "standard platelet deposition assay" or related phrase is meant performing at least one and preferably all of the following steps.

a) exposing tissue factor in a vessel of a subject e.g., by performing surgery such as an endarterectomy on a major vessel, preferably an artery, b) detectably-labeling platelets deposited at the site of injury e.g., by labeling the platelets with radioactive indium according to conventional methods; and c) detecting and preferably quantifying the amount of deposited (labeled) platelets such as by camera imaging.

The standard platelet deposition assay is preferably performed by administering at least one of the humanized antibodies (including chimerics) described herein including fragments to the subject prior to step c), for instance, after step a) or b). Performance of a particular antibody or fragment can be compared against a suitable control such as buffer or physiological saline. A preferred assay is described below in Example 4.

Other embodiments of the present invention methods are contemplated. For example, according to one embodiment, the administered humanized antibody, humanized chimeric antibody, or fragment reduces vessel injury to blood ratio by at least about 50% as determined by a standard vessel injury to blood ratio assay as described below in Example 4, preferably at least about 70% or about 95%.

Reference herein to "standard vessel injury to blood ratio assay" or related phrase means performing at least one and preferably all of the following steps.

a) exposing tissue factor in a vessel of a subject e.g., by performing surgery such as an endarterectomy on a major vessel, preferably an artery, b) detectably-labeling platelets deposited at the site of injury e.g., by use of radioactive indium, c) detecting and preferably quantifying the amount of detectably-labeled platelets at the site of vessel injury, d) detecting and preferably quantifying the amount of detectably-labeled platelets in the blood of the subject; and e) expressing the amounts of c) and d) as the ratio of platelet deposition at vessel injury site to circulating platelets in the blood.

The standard vessel injury to blood ratio assay is preferably performed by administering at least one of the humanized antibodies (including chimerics) described herein including fragments to the subject prior to step e), for instance, after step a) or b). Performance of a particular antibody or fragment can be compared against a suitable control as already described. A preferred assay is described below in Example 4.

In another embodiment, the amount of the administered humanized antibody, humanized chimeric antibody, or fragment administered to the mammal increases vessel patency by at least about 50%, preferably at least about 80%, more preferably at least about 100% as determined by a standard vessel patency assay. Patency was determined at 30 days following surgery by harvesting the vessels and placing them in fixative.

Reference herein to a "standard vessel patency assay" or related phrase means detecting and preferably quantifying an increase in vessel patency usually by inspection. Those of skill in the field that changes in vessel patency can be readily ascertained by visualization which may or may not be assisted by magnification of subject tissue such as with the aid of a microscopic lens or related device. Typically, the increase is compared to a suitable control which in many instances can be administration of buffer, physiological saline, etc. to the mammal in lieu of the antibody or fragment.

As will be appreciated, immunoglobin light and heavy chain share certain structural similarities e.g., each includes a framework of four regions (FR1-4) whose sequences are relatively conserved. Each of FR1-4 (FR1, FR2, FR3, FR4) are covalently connected by three CDRs i.e., CDR1, CDR2, CDR3. There is general recognition that the four FRs largely adopt a beta-sheet configuration and the interconnected CDRs form loops connecting, and in some instances, forming part of the beta-sheet structure. Most CDRs are held close to adjoining FRs, and with a corresponding CDR from the opposite light or heavy chain, help form the antigen binding site. A wide range of CDRs and FRs have been disclosed. See e.g., Kabat et al. in *Sequences of proteins of Immunological Interest* US Dept. of Health and Human Services, US Government Printing Office (1987).

See also EP-A-0239400 and U.S. Pat. No. 5,985,279 (describing methods of making altered antibodies in which CDRs are derived from different species than the FR).

For example, an illustrative humanized antibody for use with the present invention methods includes: 1) light and heavy chain frameworks (FRs) that are each at least about 90% identical in amino acid sequence, preferably at least 95% identical to corresponding human FRs, 2) at least one CDR derived from the murine H36.D2.B7 antibody, preferably all the CDRs being derived from same, 3) and an immunoglobin constant region that is at least about 90% identical, preferably at least 95% identical to a corresponding human immunoglobin constant region. It will be appreciated that the donor antibody has been "humanized" by the process of "humanization" because the resultant humanized antibody is expected to bind to the same antigen as the donor antibody that provides the CDRs.

It will be further appreciated that the humanized antibodies provided herein may have one or more additional conservative amino acid substitutions which can be contiguous or non-contiguous as needed. For example, such substitutions will typically have substantially little or no effect on antigen binding or other immunoglobin functions. By the phrase "conservative substitution" including plural forms is meant combinations of: gly↔ala; val↔ile↔leu; asp↔glu; asn↔gln; ser↔thr, lys↔arg; and phe↔tyr.

Additional humanized antibodies feature a variable region that is at least 70% identical in amino acid sequence (e.g., about 73% to 75% identical), to the corresponding variable region of one or more native human immunoglobin sequences. Further humanized antibodies in accord with the invention have at least 90% identity over the entire antibody to one or more human antibodies.

The U.S. Provisional Application 60/343,306; and U.S. patent application Ser. Nos. 09/990,586 and 10/230,880, for example, disclose additionally suitable humanized molecules suitable for use with the present invention.

Thus as described in the U.S. patent application Ser. No. 10/230,880, for instance, more specific humanized antibodies for use with the invention are those in each of frameworks (FRs) 1, 2, 3 and 4 has at least about 90% amino acid sequence identity, preferably at least about 95% or greater identity to the light chain FR sequences shown in FIG. 6A (SEQ ID NOS 11-12, 15-16, 68-107), preferably, the sequence shown as "LC-09" in FIG. 6A. Further preferred are those humanized antibodies that include a light chain constant region having at least about 90% amino acid sequence identity, preferably at least about 95% sequence identity or greater to the sequence shown in FIG. 8A or 9A (SEQ ID NOS 166 & 168).

Further specific humanized antibodies are those in which each of frameworks (FRs) 1, 2, 3 and 4 has at least about 90% amino acid sequence identity, preferably about 95% identity or greater to the heavy chain sequences shown in FIG. 7A (SEQ ID NOS 19-20, 23-24, 108-159), preferably, the sequence shown as "HC-08" in FIG. 7A. Additional humanized antibodies have a heavy chain constant region with at least about 90% amino acid sequence identity, preferably at least about 95% identity or greater, to sequence shown in FIG. 8B or 9B (SEQ ID NOS 167 & 169).

In certain embodiments, the humanized antibody will have an IgG1 (hOAT) or IgG4 (HFAT) isotype. See Example 7.

Also provided by the present invention are functional fragments of the humanized immunoglobins disclosed herein including, but not limited to, fragments of humanized antibodies and chimeric antibodies. Preferred fragments specifically bind TF with an affinity constant (Kd) of less than about 1 nM, preferably less than about 0.5 nM, more preferably between from about 0.01 nM to about 0.4 nM. Specifically preferred are antigen binding Fab, Fab', and F(ab)$_2$ fragments.

As disclosed in the U.S. patent application Ser. No. 10/230,880, for instance, additional humanized antibodies can be used with the present invention methods such as those featuring at least one murine complementarity determining region (CDR) from H36.D2.B7, e.g., CDR1, CDR2, CDR3 of that antibody. In a preferred embodiment, the antibodies bind specifically to human tissue factor (TF) to form a complex. Typically, the factor X or factor IX binding to TF or TF:VIIa and activation by TF:FVIIa thereto is inhibited. As mentioned above, preferred CDRs (light and heavy chain) are from a rodent source, typically the mouse, and preferably the murine H36.D2.B7 antibody.

In one embodiment, the antibodies further include at least one human framework (FR) region. Preferably, all the FR regions (light and heavy chain) are human.

In a more particular embodiment of the present invention, the first CDR (CDR1) of the heavy chain hypervariable region is at least 90% identical to the CDR1 amino acid sequence shown in FIG. 7B (SEQ ID NOS 160 & 163), preferably at least about 95% identical or greater to that sequence. Typically, the second CDR (CDR2) of the heavy chain hypervariable region is at least 90% identical to the CDR2 amino acid sequence shown in FIG. 7C (SEQ ID NOS 161 & 164), preferably at least about 95% identical or greater. Preferably also, the third CDR (CDR3) of the heavy chain hypervariable region is at least 90% identical to the CDR3 sequence shown in FIG. 7D (SEQ ID NOS 162 & 165), more preferably about 95% identical or greater to that sequence. See the U.S. patent application Ser. No. 10/230,880 for additional information relating to FIGS. 7A-D.

Identity between two nucleic acid sequences can be determined by inspection and/or use of conventional computer software such as BLAST and FASTA. Identity between related amino acid sequences can be determined by related programs such as TFASTA.

In another invention embodiment, the first CDR (CDR1) of the light chain hypervariable region is at least 90% identical to the CDR1 amino acid sequence shown in FIG. 6B (residues 24-34 of SEQ ID NO: 2), preferably at least about 95% identical or greater. Typically, the second CDR (CDR2) of the light chain hypervariable region is at least 90% identical to the CDR2 amino acid sequence shown in FIG. 6C (SEQ ID NO: 6), preferably about 95% identical or greater. Preferably, the third CDR (CDR3) of the light chain hypervariable region is at least 90% identical to the CDR3 amino acid sequence shown in FIG. 6D (SEQ ID NO: 7), more preferably about 95% identical or greater to that sequence. See the U.S. patent application Ser. No. 10/230,880 for additional information relating to FIGS. 6A-C.

Additional humanized antibodies for use with the invention include a first framework (FR1) of the heavy chain hypervariable region which FR1 is at least 90% identical to the amino acid sequence shown in FIG. 7A (SEQ ID NO: 115) as "FR1 HC-08", preferably about 95% identical or greater to that sequence. In one embodiment, the FR1 comprises at least one of the following amino acid changes: E1 to Q; Q5 to V; P9 to G; L11 to V; V12 to K; Q19 to R; and T24 to A. Preferably, the FR1 includes two, three, four, five, or six of those changes with all of those amino acid changes being preferred for many applications.

Further humanized antibodies suitable for use with the invention methods include a second framework (FR2) of the heavy chain hypervariable region which FR2 is at least 90% identical to the sequence shown in FIG. 7A (SEQ ID NO: 128) as "FR2 HC-08", preferably about 95% identical or greater to that sequence. In one embodiment, the FR2 at least one of the following amino acid changes: 41H to P; and 44S to G. A preferred FR2 includes both of those amino acid changes.

The invention also features humanized antibodies in which a third framework (FR3) of the heavy chain hypervariable region is at least 90% identical to the sequence shown in FIG. 7A (SEQ ID NO: 141) as "FR3 HC-08", preferably about 95% identical or greater to that sequence. In one embodiment, the FR3 includes at least one of the following amino acid changes: 76S to T; 77T to S; 80F to Y; 82H to E; 84N to S; 87T to R; 89D to E; and 91S to T. A preferred FR3 includes two, three, four, five or six of those amino acid changes with all seven of those amino acid changes being generally preferred.

Also featured for use with the present methods are humanized antibodies in which the fourth framework (FR4) of the heavy chain hypervariable region is at least 90% identical to the amino acid sequence shown in FIG. 7A (SEQ ID No: 154) as "FR4 HC-08", preferably at least about 95% identical or greater to that sequence. Preferably, the FR4 includes the following amino acid change: 113L to V.

Additional humanized antibodies for use in accord with the invention feature a first framework (FR1) of the light chain hypervariable region which is at least about 90% identical to the amino acid sequence shown in FIG. 6A (SEQ ID NO: 74) as "FR1 LC-09", preferably at least about 95% identical or greater to that sequence. In one embodiment, the FR1 comprises at least one of the following amino acid changes: 11Q to L; 15L to V; 17E to D; and 18 to R. A preferred FR1 includes two or three of such amino acid changes with all four amino acid changes being generally preferred.

The present invention also features use of humanized antibodies in which a second framework (FR2) of the light chain hypervariable region is at least about 90% identical to the amino acid sequence shown in FIG. 6A (SEQ ID NO: 84) as "FR2 LC-09", preferably at least about 95% identical or greater to that sequence. A preferred FR2 has the following amino acid change: 37Q to L.

Also encompassed by the invention is the use of humanized antibodies in which a third framework (FR3) of the light chain hypervariable region is at least about 90% identical to the amino acid sequence shown in FIG. 6A (SEQ ID NO: 94) as "FR3 LC-09", preferably at least about 95% identical or greater to that sequence. In one embodiment, the FR3 has at least one of the following amino acid changes: 70K to D, 74K to T, 80A to P, 84A to V, and 85N to T. Preferably, the FR3 has two, three, or four of such amino acid changes with all five of the changes being generally preferred.

Additional humanized antibodies for use with the present invention include a fourth framework (FR4) of the light chain hypervariable region which FR4 is at least about 90% identical to the sequence shown in FIG. 6A (SEQ ID NO: 104) as "FR4 LC-09", preferably at least about 95% identical or greater to that sequence. In one embodiment, the FR4 includes at least one and preferably all of the following amino acid changes: 100A to Q; and 106L to I.

The invention also features a human TF binding fragment of the foregoing humanized antibodies as provided in the U.S. Patent Application Nos. 60/343,306; 09/990,586; and 10/230,880. Examples of such fragments include Fab, Fab', and F(ab)$_2$.

In a particular embodiment, the invention features use of a humanized antibody that includes at least one murine complementarity determining region (CDR) from the H36.D2.B7 antibody. Preferably, that antibody binds specifically to human tissue factor (TF) to form a complex in which factor X or factor IX binding to TF or TF/VIIa and activation by TF/VIIa thereto is inhibited. Also preferably, the humanized antibody includes, on the heavy chain, at least one of and more preferably all of the following components:

a) a first CDR (CDR1) which is at least 95% identical to CDR1 amino acid sequence shown in FIG. 7B (SEQ ID NOS 106 & 163), b) a second CDR (CDR2) which is at least 95% identical to the CDR2 amino acid sequence shown in FIG. 7C (SEQ ID NOS 161 & 164), c) a third CDR (CDR3) which is at least 95% identical to the CDR3 amino acid sequence shown in FIG. 7D (SEQ ID NOS 162 & 165), d) a first framework (FR1) which is at least 95% identical to the amino acid sequence shown in FIG. 7A (SEQ ID NO: 115) as "FR1 HC-08", e) a second framework (FR2) which is at least 95% identical to the amino acid sequence shown in FIG. 7A (SEQ ID NO: 128) as "FR2 HC-08", f) a third framework (FR3) which is at least 95% identical to the amino acid sequence shown in FIG. 7A (SEQ ID NO: 141) as "FR3 HC-08", and g) a fourth framework (FR4) which is at least 95% identical to the amino acid sequence shown in FIG. 7A (SEQ ID No: 154) as "FR4 HC-08".

In a particular embodiment, the humanized antibody also includes, on the light chain, at least one of and preferably all of the following components:

h) a first CDR (CDR1) which is at least 95% identical to CDR1 amino acid sequence shown in FIG. 6B (residues 24-34 of SEQ ID NO: 2), i) a second CDR (CDR2) which is at least 95% identical to the CDR2 amino acid sequence shown in FIG. 6C (SEQ ID NO: 6), j) a third CDR (CDR3) which is at least 95% identical to the CDR3 amino acid sequence shown in FIG. 6D (SEQ ID NO: 7), k) a first framework (FR1) which is at least 95% identical to the amino acid sequence shown in FIG. 6A (SEQ ID NO: 74) as "FR1 LC-09", l) a second framework (FR2) which is at least 95% identical to the amino acid sequence shown in FIG. 6A (SEQ ID NO: 84) as "FR2 LC-09", m) a third framework (FR3) which is at least 95% identical to the amino acid sequence shown in FIG. 6A (SEQ ID NO: 94) as "FR3 LC-09", and n) a fourth framework (FR4) which is at least 95% identical to the amino acid sequence shown in FIG. 6A (SEQ ID No: 104) as "FR4 LC-09". Preferably, the humanized antibody further includes the light chain constant sequence of FIG. 8A (SEQ ID No: 166) or FIG. 9A (SEQ ID No: 168). Also preferably, the antibody includes the heavy chain constant region of FIG. 8B (SEQ ID No: 167) or FIG. 9B (SEQ ID No: 169).

The invention also features use of a humanized antibody that includes, on the heavy chain, at least one of and preferably all of the following components:

a) a first CDR (CDR1) identical to the CDR1 amino acid sequence shown in FIG. 7B (SEQ ID NOS 160 & 163), b) a second CDR (CDR2) identical to the CDR2 amino acid sequence shown in FIG. 7C (SEQ ID NOS 161 & 164), c) a third CDR (CDR3) identical to the CDR3 amino acid sequence shown in FIG. 7D (SEQ ID NOS 162 & 165), d) a first framework (FR1) identical to the amino acid sequence shown in FIG. 7A (SEQ ID NO: 115) as "FR1 HC-08", e) a second framework (FR2) identical to the amino acid sequence shown in FIG. 7A (SEQ ID NO: 128) as "FR2 HC-08", f) a third framework (FR3) identical to the amino acid sequence shown in FIG. 7A (SEQ ID NO: 141) as "FR3 HC-08"; and g) a fourth framework (FR4) identical to the amino acid sequence shown in FIG. 7A (SEQ ID No: 154) as "FR4 HC-08".

In one embodiment, the humanized antibody used in the present methods further includes, on the light chain, at least one of and preferably all of the following components:

h) a first CDR (CDR1) identical to CDR1 amino acid sequence shown in FIG. 6B (residues 24-34 of SEQ ID NO: 2), i) a second CDR (CDR2) identical to the CDR2 amino acid sequence shown in FIG. 6C (SEQ ID NO: 6), j) a third CDR (CDR3) identical to the CDR3 amino acid sequence shown in FIG. 6D (SEQ ID NO: 7), k) a first framework (FR1) identical to the amino acid sequence shown in FIG. 6A (SEQ ID NO: 74) as "FR1 LC-09", l) a second framework (FR2) identical to the amino acid sequence shown in FIG. 6A (SEQ ID NO: 84) as "FR2 LC-09", m) a third framework (FR3) identical to the amino acid sequence shown in FIG. 6A (SEQ ID NO: 94) as "FR3 LC-09", and n) a fourth framework (FR4) identical to the amino acid sequence shown in FIG. 6A (SEQ ID No: 104) as "FR4 LC-09". Preferably, the humanized antibody further includes the light chain constant sequence of FIG. 8A (SEQ ID No: 166) or FIG. 9A (SEQ ID No: 168). Also preferably, the antibody includes the heavy chain constant region of FIG. 8B (SEQ ID No: 167) or FIG. 9B (SEQ ID No: 169).

In another example, the invention provides methods of inhibiting one or a combination of thromboses in a mammal such as a primate and particularly a human subject in need of such treatment that includes administering to the mammal, a therapeutically effective amount of a humanized immunoglobin, more particularly a humanized antibody, humanized chimeric antibody or suitable fragment thereof. Typically, the humanized antibody binds specifically to human tissue factor (TF) to form the binding complex. Preferably, the humanized antibody or fragment includes, on the heavy chain, at least one of and preferably all of the following components:

a) a first CDR (CDR1) which is at least 95% identical to CDR1 amino acid sequence shown in FIG. 7B (SEQ ID NOS 160 & 163), b) a second CDR (CDR2) which is at least 95% identical to the CDR2 amino acid sequence shown in FIG. 7C (SEQ ID NOS 161 & 164), c) a third CDR (CDR3) which is at least 95% identical to the CDR3 amino acid sequence shown in FIG. 7D (SEQ ID NO: 162 & 165), d) a first framework (FR1) which is at least 95% identical to the amino acid sequence shown in FIG. 7A (SEQ ID NO: 115) as "FR1 HC-08", e) a second framework (FR2) which is at least 95% identical to the amino acid sequence shown in FIG. 7A (SEQ ID NO: 128) as "FR2 HC-08", f) a third framework (FR3) which is at least 95% identical to the amino acid sequence shown in FIG. 7A (SEQ ID NO: 141) as "FR3 HC-08", g) a fourth framework (FR4) which is at least 95% identical to the amino acid sequence shown in FIG. 7A (SEQ ID No: 154) as "FR4 HC-08".

In a more specific invention embodiment, the humanized antibody includes, on the light chain, at least one of, and preferably all of the following components:

h) a first CDR (CDR1) which is at least 95% identical to CDR1 amino acid sequence shown in FIG. 6B (residues 24-34 of SEQ ID NO: 2), i) a second CDR (CDR2) which is at least 95% identical to the CDR2 amino acid sequence shown in FIG. 6C (SEQ ID NO: 6), j) a third CDR (CDR3) which is at least 95% identical to the CDR3 amino acid sequence shown in FIG. 6D (SEQ ID NO: 7), k) a first framework (FR1) which is at least 95% identical to the amino acid sequence shown in FIG. 6A (SEQ ID NO:74) as "FR1 LC-09", l) a second framework (FR2) which is at least 95% identical to the amino acid sequence shown in FIG. 6A (SEQ ID NO: 84) as "FR2 LC-09", m) a third framework (FR3) which is at least 95% identical to the amino acid sequence shown in FIG. 6A (SEQ ID NO: 94) as "FR3 LC-09", n) a fourth framework (FR4) which is at least 95% identical to the amino acid sequence shown in FIG. 6A (SEQ ID No: 104) as "FR4 LC-09", o) a light chain constant region which is at least 95% identical to the amino acid sequence shown in FIG. 8A (SEQ ID No: 166) or FIG. 9A (SEQ ID No: 168); and p) a heavy chain constant region which is at least 95% identical to the amino acid sequence shown in FIG. 8B (SEQ ID No: 167) or FIG. 9B (SEQ ID No: 169).

In a more specific embodiment, the humanized antibody or fragment thereof includes, on the heavy chain, at least one of and preferably all of the following components:

a) a first CDR (CDR1) identical to CDR1 amino acid sequence shown in FIG. 7B (SEQ ID NOS 160 & 163), b) a second CDR (CDR2) identical to the CDR2 amino acid sequence shown in FIG. 7C (SEQ ID NOS 161 & 164), c) a third CDR (CDR3) identical to the CDR3 amino acid sequence shown in FIG. 7D (SEQ ID NOS 162 & 165), d) a first framework (FR1) identical to the amino acid sequence shown in FIG. 7A (SEQ ID NO: 115) as "FR1 HC-08", e) a second framework (FR2) identical to the amino acid sequence shown in FIG. 7A (SEQ ID NO: 128) as "FR2 HC-08", f) a third framework (FR3) identical to the amino acid sequence shown in FIG. 7A (SEQ ID NO: 141) as "FR3 HC-08", g) a fourth framework (FR4) identical to the amino acid sequence shown in FIG. 7A (SEQ ID No: 154) as "FR4 HC-08";

and on the light chain:

h) a first CDR (CDR1) identical to CDR1 amino acid sequence shown in FIG. 6B (residues 24-34 of SEQ ID NO: 2), i) a second CDR (CDR2) identical to the CDR2 amino acid sequence shown in FIG. 6C (SEQ ID NO: 6), j) a third CDR (CDR3) identical to the CDR3 amino acid sequence shown in FIG. 6D (SEQ ID NO: 7), k) a first framework (FR1) identical to the amino acid sequence shown in FIG. 6A (SEQ ID NO: 74) as "FR1 LC-09", l) a second framework (FR2) identical to the amino acid sequence shown in FIG. 6A (SEQ ID NO: 84) as "FR2 LC-09", m) a third framework (FR3) identical to the amino acid sequence shown in FIG. 6A (SEQ ID NO: 94) as "FR3 LC-09", n) a fourth framework (FR4) identical to the amino acid sequence shown in FIG. 6A (SEQ ID No: 104) as "FR4 LC-09", o) a light chain constant region which is identical to the amino acid sequence shown in FIG. 8A (SEQ ID No: 166) or FIG. 9A (SEQ ID No: 168), and p) a heavy chain constant region which is identical to the amino acid sequence shown in FIG. 8B (SEQ ID No: 167) or FIG. 9B (SEQ ID No: 169).

Thus in one embodiment of the present methods for preventing or treating thromboses, a suitable humanized antibody, humanized chimeric antibody or fragment thereof includes at least one fully human framework (FR) region. Additionally, such an antibody can have at least 90%, preferably at least 95%, more preferably at least 98% sequence identity to a human antibody. Further humanized antibodies suitable for use with the invention have at least 70% amino acid sequence identity to a human antibody variable region. Additionally preferred humanized antibodies are preferably monoclonal and may be in a single-chain format as desired.

The humanized antibodies of the present invention may exist in a variety of suitable forms in addition to whole antibodies; including, for example, Fv, Fab, and F(ab')$_2$ as well as bifunctional hybrid antibodies (e.g., Lanzavecchia et al., *Eur. J. Immunol.* 17: 105 (1987)) and in single chains (e.g., Huston et al., *Proc. Natl. Acad. Sci. U.S.A.*, 85: 5879-5883 (1988) and Bird et al., *Science* 242: 423-426 (1988), which are incorporated herein by reference). (See, Hood et al., Immunology, Benjamin, N.Y., 2.sup.nd ed. (1984), Harlow and Lane, *Antibodies. A Laboratory Manual*, Cold Spring Harbor Laboratory (1988) and Hunkapiller and Hood, *Nature,* 323: 15-16 (1986), which are incorporated herein by reference.).

The humanized antibodies disclosed herein can be produced by one or a combination of strategies including those already referenced above. See e.g., S. L. Morrison, supra; Oi et al., supra; Teng et al., supra; Kozbor et al., supra; Olsson et al., supra; and other references cited previously.

See also the U.S. Pat. No. 5,693,762 by Queen et al. and references disclosed therein.

Particularly useful methods have been disclosed the U.S. Patent Application Nos. 60/343,306; 09/990,586; and 10/230, 880, for instance. Briefly, four general steps can be employed to humanize an antibody. First, the amino acid sequences of the mouse antibody light and heavy chains were obtained from the cH36 mouse-human chimeric antibody. Second, the cH36 antibody was humanized by determining which human antibody framework region gave the "best fit" i.e., most closely resembled the mouse framework region amino acid sequence. Third, relevant light and heavy chain FR sequences were humanized, and fourth, transfection and expression of isolated nucleic acid(s) that encode the humanized light or heavy chain (or humanized light and heavy chain e.g., see the mega vectors described below).

The following three nucleic acid vectors pSUN36 (humanized anti-TF antibody Ig G1-HC expression vector), pSUN37 (humanized anti-TF antibody Ig G4-HC expression vector), and pSUN38 (humanized anti-TF antibody LC expression vector) may be useful in some approaches to make the humanized immunoglobins disclosed herein. Such vectors have been deposited pursuant to the Budapest Treaty with the American Type Culture Collection (ATCC) at 10801 University Boulevard, Manassas Va. 20110-2209. The vectors were assigned the following Accession Numbers: PTA-3727 (pSUN36); PTA-3728 (pSUN37); and PTA-3729 (pSUN38).

As provided in the U.S. Patent Application Nos. 60/343, 306; 09/990,586; and 10/230,880, humanized antibodies and fragments thereof according to the invention can be tested for function by one or a combination of standard methods. A preferred method is what is sometimes referred to herein as a "standard prothrombin time" assay or related phrase. The standard prothrombin time (PT) assay typically involves at least one and preferably all of the following steps:

a) combining a solution containing lipidated TF and calcium with human plasma; and b) measuring and recording the clotting times using a coagulation analyzer.

See also the U.S. Pat. No. 5,986,065 and the PCT/US98/04644 (WO 98/40408) application for additional disclosure relating to the standard PT assay including preferred reagent sources.

The humanized antibodies and fragments thereof provided herein can be readily tested in standard PT assay. An aliquot of the purified antibody or fragment, preferably about 200 nM to about 2000 nM, is added to the human plasma (Ci-Trol Coagulation Control), and a solution containing lipidated recombinant TF and calcium (such as Innovin from Dade Behring) is added to the human plasma to start the PT reaction.

Highly preferred humanized antibodies and fragments thereof including whole IgG, Fab, Fab', F(ab)$_2$, and single chain antibodies (comprising the antigen binding variable regions of the humanized antibodies) will increase blood clotting time by at least about 5 seconds when tested in the standard assay at a final concentration of at least about 1 nM to about 20 nM, preferably about 5 nM to about 15 nM, more preferably about 10 nM in the assay. A typical control is a standard PT assay performed without adding any antibody of fragment. Additionally preferred antibodies and fragments of the invention achieve at least about 90% inhibition of TF-dependent coagulation, preferably at least about 95% inhibition or greater when compared to the control.

Humanized antibodies, humanized chimerics and fragments suitable for use with the invention are preferably substantially pure. References to an antibody being "substantially pure" mean an antibody or protein which has been separated from components which naturally accompany it. For example, by using standard immunoaffinity or Protein A affinity purification techniques, an antibody of the invention can be purified from a hybridoma culture by using recombinant human TF coupled resin or Protein A resin. Similarly, recombinant human TF or native human TF can be obtained in substantially pure form by using an antibody of the invention with standard immunoaffinity purification techniques. Particularly, an antibody or protein is substantially pure when at least 50% of the total protein (weight % of total protein in a given sample) is an antibody or protein of the invention. Preferably the antibody or protein is at least 60 weight % of the total protein, more preferably at least 75 weight %, even more preferably at least 90 weight %, and most preferably at least 98 weight % of the total material. Purity can be readily assayed by known methods such as SDS (PAGE) gel electrophoresis, column chromatography (e.g., affinity chromatography) or HPLC analysis.

As discussed above, humanized immunoglobins for use with the invention can be administered to a mammal, preferably a primate such as a human, to prevent or reduce thrombotic occlusive disorders such as those attributable to TF-mediated activation of coagulation. Typical administration routes include use of a composition including one or more pharmaceutically acceptable non-toxic carriers such as sterile water or saline, glycols such as polyethylene glycol, oils of vegetable origin, and the like. In particular, biocompatible, biodegradable lactide polymer, lactide glycolide copolymer or polyoxyethylene, polyoxypropylene copolymers may be useful excipients to control the release of the antibody-containing compositions described herein. Other potentially useful administration systems include ethylene vinyl acetate copolymer particles, osmotic pumps, and implantable infusion systems and liposomes. Generally, an anti-coagulant composition of the invention will be in the form of a solution or suspension (or a lyophilized form that can be reconstituted to a solution or suspension), and will preferably include approximately 0.01% to 10% (w/w) of the antibody of the present invention, preferably approximately 0.01% to 5% (w/w) of the antibody. The antibody can be administered as a sole active ingredient in the composition, or as a cocktail including one or more other anti-coagulant (e.g., heparin, hirudin or hirulog, coumadin, warfarin), anti-platelet (e.g., aspirin, Plavix, Ticlid, ReoPro, Integrilin or Aggrestat), or thrombolytic agents (e.g., tissue plasminogen activator, strepokinase and urokinase).

Methods of the invention can be used before, during or after administration of one or more suitable anti-coagulant, anti-platelet or thrombolytic agents to boost or prolong desired anti-thrombosis effect.

Therapeutic anti-thrombotic compositions according to the invention (including cocktails) are suitable for use in parenteral or intravenous administration, particularly in the form of liquid solutions. Such compositions may be conveniently administered in unit dose and may be prepared in accordance with methods known in the pharmaceutical art. See *Remington's Pharmaceutical Sciences*, (Mack Publishing Co., Easton Pa., (1980)). By the term "unit dose" is meant a therapeutic composition of the present invention employed in a physically discrete unit suitable as unitary dosages for a primate such as a human, each unit containing a pre-determined quantity of active material calculated to produce the desired therapeutic effect in association with the required diluent or carrier. The unit dose will depend on a variety of factors including the type and severity of thrombosis to be treated, capacity of the subject's blood coagulation system to utilize the administered composition, etc. Precise amounts of the antibody to be administered typically will be guided by judgment of the practitioner, however, the unit dose will generally depend on the route of administration and be in the range of 10 ng/kg body weight to 50 mg/kg body weight per day, more typically in the range of 100 ng/kg body weight to about 10 mg/kg body weight per day. Suitable regimens for initial administration in booster shots are also variable but are typified by an initial administration followed by repeated doses at one or more hour intervals by a subsequent injection or other administration. Alternatively, continuous or intermittent intravenous infusions may be made sufficient to maintain concentrations of at least from about 10 nanomolar to 10 micromolar of the antibody in the blood.

In practice, the invention methods can be used as separately administered compositions given in conjunction with other anti-clotting agents including aspirin, coumadin, heparin, hirudin, or hirulog. Also envisioned is co-administration with anti-platelet (e.g., ReoPro, Integrilin, Aggrestat, Plavix, and/or Ticlid) and/or thrombolytic agents (e.g., tissue plasminogen activator, strepokinase and urokinase).

In some instances, it may be desirable to modify the antibody of the present invention to impart a desirable biological, chemical or physical property thereto. More particularly, it may be useful to conjugate (i.e. covalently link) the antibody to a pharmaceutical agent, e.g a fibrinolytic drug such as t-PA, streptokinase, or urokinase to provide fibrinolytic activity or to a targeting agent such as a fibrin-binding domain. Such linkage can be accomplished by several methods including use of a linking molecule such as a heterobifunctional protein cross-linking agent, e.g. SPDP, carbodimide, or the like, or by recombinant methods.

As discussed, the invention is useful for preventing or treating thrombosis. Particularly, the invention can be employed to prevent or treat restenosis associated with, e.g., an invasive medical procedure such as percutanous transluminal coronary intervention, cardiopulmonary bypass surgery, endarterectomy, peripheral vascular bypass grafts, reconstructive or plastic surgery, joint replacement; a heart ailment such as myocardial infarction, cardiomyopathy, valvular heart disease, stable angina, unstable angina, or artrial fibrillation associated with embolization; a coagulopathy including disseminated intravascular coagulation, deep vein thrombosis, deployment of an implementation such as a stent or catheter; shock (e.g., septic shock syndrome), vascular trauma, liver disease, hemorrhagic stroke, heat stroke, malignancies (e.g., pancreatic, ovarian, or small lung cell carcinoma), lupus, eclampsia, perivascular occlusive disease, and renal disease.

Although a range of therapeutic anti-coagulant compositions of the invention have been described above, other compositions that include the humanized antibodies, humanized chimeric antibodies and fragments of same are contemplated. For example, such antibodies and fragments may be used as the sole therapeutic agent or in combination with one or more other humanized antibodies or fragments to achieve a desired outcome. Such antibodies and fragments may also be used in combination with other antibodies, particularly human monoclonal antibodies reactive with other markers on cells responsible for the disease.

In embodiments in which the therapeutic anti-coagulant compositions described herein include one or more humanized antibodies or fragments, that composition may include a solution of the antibody or a cocktail thereof dissolved in an acceptable carrier, preferably an aqueous carrier. A variety of aqueous carriers have already been referenced such as water, buffered water, 0.4% saline, 0.3% glycine and the like. These solutions are preferably sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc., in accordance with the particular mode of administration selected. See generally, Remington's Pharmaceutical Sciences, supra.

If desired, the therapeutic anti-coagulant compositions described herein can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

For some prophylactic applications, it will be helpful to use the present invention methods with a patient not already in a detectable disease state to enhance the patient's resistance to the disease. Such an amount is defined to be a "prophylactically effective dose". In this use, the precise amounts again depend upon the patient's state of health and general level of immunity, but generally range from 0.03 to 25 mg/kg, especially 0.25 to 2.5 mg/kg. Such administration amounts are generally suitable for use in the methods described herein however they may be adjusted depending on recognized parameters such as the humanized immunoglobin selected, the indication to be treated, health of the individual, etc.

As discussed, the invention also features kits that include subject antibodies or fragments thereof. In one embodiment, the humanized antibodies or fragments thereof can be supplied for use against or in the detection of TF antigen. Thus, for instance, one or more humanized antibodies, fragments thereof, or single chain antibodies may be provided, usually in a lyophilized form in a container. Such antibodies, fragments, or single chain antibodies, which may be conjugated to a previously mentioned label or toxin, or unconjugated, are included in the kits with buffers, such as Tris, phosphate, carbonate, etc., stabilizers, biocides, inert proteins, e.g., serum albumin, or the like. Generally, these materials will be present in less than about 5% by weight based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assay, this will usually be present in a separate vial. The second antibody is typically conjugated to a label and formulated in an analogous manner with the antibody formulations described above. The kit will generally also include a set of instructions for use.

As discussed, the invention also provides a variety of methods of inhibiting blood coagulation in a mammal, preferably a primate such as a human patient.

For example, in one embodiment, the methods include administering to the mammal a therapeutically effective amount of at least one of, preferably one, two or three of the humanized antibodies, chimeric or fragment thereof as provided herein. In most embodiments, the methods further include forming a specific complex between the antibody and the TF to inhibit the blood coagulation.

Also provided are methods of inhibiting blood coagulation in a mammal that include administering to the mammal, a therapeutically effective amount of the humanized antibodies disclosed herein or a fragment thereof. Typical antibodies and fragments bind specifically to human tissue factor (TF) to form a complex, and further wherein factor X or factor IX binding to TF or TF:FVIIa and activation by TF:FVIIa thereto is inhibited. In most embodiments, the methods further include forming a specific complex between the antibody and the TF to inhibit the blood coagulation.

As discussed, the invention also provides methods for performing plastic, reconstructive, or transplant surgery in a mammal that includes, in one embodiment, introducing a graft into the mammal and contacting the graft with a therapeutically effective amount of at least one any of the humanized antibodies, chimeric antibodies, or fragments disclosed herein. An animal model designed to examine thrombosis during surgery is the skin flap surgery model described in detail in Example 5.

By the phrase "standard skin flap assay" or related phrase is meant conducting at least one and preferably all of the following steps:

a) making a skin flap in a subject mammal and reducing blood supply therein, b) ligating the skin flap to the mammal, c) administering to the ligated skin flap a detectable label capable of reporting blood perfusion e.g, a fluorescent dye such as fluorescein; and d) detecting and optionally quantifying sites of poor blood perfusion (ie. dark regions).

The standard skin flap assay is preferably performed by administering at least one of the humanized antibodies (including chimerics) or fragments thereof to the mammal prior to step c), for instance, after step a) or b). A preferred skin flap assay is described below in Example 5.

In one embodiment of the method, amount of the humanized antibody, humanized chimeric antibody or fragment administered to the mammal is sufficient to prevent or reduce thrombosis by at least about 50% as determined by a standard skin flap model, preferably at least about 70% or 80% according to that model as described in Example 5. Typical methods further include preventing or reducing devascularization of the graft as determined by a standard skin flap model e.g., by preventing or reducing at least one of edema, erythema, and necrosis in the graft.

The following conditions, among others disclosed herein, can be prevented or treated by using the present invention.

1. Angioplasty and Thrombosis: Percutaneous coronary interventional (PCI) techniques are now widely used to treat patients with acute and chronic coronary artery disease. During PCI, blood vessel is injured and TF and other procoagulant components are exposed to blood coagulation factors and platelets, triggering coagulation and platelet activation, and leading to thrombosis. Therefore, abrupt vessel closure in the short term and restenosis in the long term are the limitations to the event free survival following balloon angioplasty. cH36 was shown in Example 6 to inhibit angioplasty-induced thrombosis.

2. Acute Coronary Syndrome and Thrombosis: Atherosclerothesis is a systemic disease responsible for acute coronary syndromes (ACS) such as unstable angina, acute myocardial infarction, and sudden cardiac death. ACS is the major cause of morbidity and mortality in developed countries. Most ACS patients share a common pathophysiological phenomenon: coronary thrombosis. Coronary thrombosis is caused by plaque disruption or plaque erosion. The consequence of plaque disruption and erosion is the exposure of TF within the plaques to the flowing blood, leading to the activation of coagulation cascade and platelets. An electrolytic model in cynomolgus monkeys was employed to mimic the events of plague disruption in Example 7.

3. In-Stent Thrombosis: Coronary stents are a major advancement in percutaneous coronary intervention. However, in-stent thrombosis (restenosis) is a problem, occurring in 20% to 30% of cases. In a perfusion system, a thrombus forms on stent surfaces. The stent thrombus contains fibrin, platelets, and leucocytes. Very interestingly, the thrombus also contains TF, which is carried over to stent surface by leucocytes from the blood during perfusion (see Peter L. A. G. et al., *PNAS* 96:2311-2315 (1999); Tullio P et al., *J. Am. Coll. Cardiol.* 40:360-366 (2002)). cH36 can significantly reduce the thrombus formation on stent surfaces. Once the thrombus is formed, it can trigger further thrombin generation due to the presence of TF in the thrombus. Thus, cH36 can strongly inhibit thrombin generation induced by thrombus.

The invention also provides a kit for performing or assisting in the performance of the present invention methods. A typical kit includes at least one of the humanized immunoglobins referred to herein including particular humanized antibodies, chimeric antibodies, or fragments thereof that binds specifically to human TF to a complex. Typically, such humanized immunoglobins will be provided in at least one pharmaceutically acceptable vehicle such as those mentioned herein including those useful in dissolving, stabilizing or otherwise providing such immunoglobins in a form useful to practice the invention.

All documents mentioned herein are fully incorporated by reference in their entirety.

The following non-limiting examples are illustrative of the invention.

As discussed, the U.S. Pat. No. 5,986,065 and the PCT/US98/04644 (WO 98/40408) disclose how to make and use the murine H36.D2 antibody as well as related molecules. In those documents, the antibodies H36 and H36.D2 are referred to. Those antibodies are the same antibody as H36.D2.B7, but H36 is derived from the mother clone, and H36.D2 is obtained from the primary clone, whereas H36.D2.B7 is obtained from the secondary clone. As pointed out in the U.S. Pat. No. 5,986,065 and the PCT/US98/04644 (WO 98/40408), no differences have been observed between those three clones with respect to ability to inhibit TF or other physical properties. In general usage, H36 is often used to indicate anti-TF antibody produced by any of these clones or related cell lines producing the antibody. In addition the derivatives of H36, including the chimeric antibody cH36 and the humanized versions hOAT (containing human IgG1Fc domain) and hFAT (containing human IgG4 Fc domain), bind to tissue factor similarly.

Certain of the following Examples have been disclosed in the U.S. patent application Ser. No. 10/230,880 entitled *Method of Humanizing Immune System Molecules* as filed on Aug. 29, 2002.

Example 1

Humanization of Anti-Tissue Factor Antibody

The previous examples describe how to make and use a particular murine antibody called H36.D2 (sometimes also called H36 as discussed above). The present example shows how to make and use a humanized version of that antibody. A humanized H36 antibody has a variety of uses including helping to minimize potential for human anti-mouse antibody (HAMA) immunological responses. These and other undesired responses pose problems for use of the H36 antibody in human therapeutic applications.

A. Preparation of Chimeric Anti-Tissue Factor Antibody (cH36)

The H36 antibody described previously is an IgG2a murine antibody. H36 was first converted to a mouse-human chimeric antibody for clinical development. To do this, the heavy and light chain genes for H36 were cloned (see U.S. Pat. No. 5,986,065). The heavy chain variable region was fused to a human IgG4 constant (Fc) domain and the light chain variable region was fused to a human kappa light chain constant domain. The resulting IgG4K chimeric antibody was designated cH36. For multiple uses of H36 or cH36 in patients with chronic diseases, a fully humanized cH36 is preferred so that it will decease or eliminate any human anti-mouse antibody immunological response. The humanization of cH36 is described below.

B. Humanization of cH36 Antibody

Humanization of the chimeric anti-tissue factor antibody cH36 was achieved by using a "best-fit" method. This method takes full advantage of the fact that a great number of human IgGs with known amino acid sequences are available in the public database. The individual frameworks of the mouse heavy and light variable regions in cH36 are compared with their corresponding human frameworks in the Kabat database (see http://immuno.bme.nwu.edu). The following criteria were used to select the desired human IgG frameworks for humanization: (1) The number of mismatched amino acids was kept as low as possible. (2) Amino acids inside the "vernier" zone (amino acids in this zone may adjust CDR structure and fine-tune the fit to antigen, see Foote, J. and Winter, G., *J. Mol. Bio.* 224(2): 487-499 [1992]) were left unchanged. (3) Conservative amino acid substitutions were favored when evaluating similar candidates. The matching program used for this comparison can be found in Kabat's home page. See also Johnson G, Wu T. "Kabat database and its application: Future directions." *Nucleic Acids Res.* 29:205-206 (2001). The program finds and aligns regions of homologies between the mouse sequences and human sequences in the Kabat's database. By using this unique best-fit method, it is anticipated that the humanized LC or HC variable region of the target IgG may have all the four FRs derived from as few as one human IgG molecule or to as many as four different human IgG molecules.

(i). Selection of Human Kappa Light Chain Variable Region Frameworks

The amino acid sequence in each of the frameworks of cH36 LC was compared with the amino acid sequence in the corresponding FR in human kappa light chain variable region in Kabat Database. The best-fit FR was selected based on the three criteria described above.

The amino acid sequence of human kappa light chain variable region with a Kabat Database ID No. 005191 was selected for humanization of cH36 LC FR1. The amino acid sequence of human kappa light chain variable region with a Kabat Database ID No. 019308 was selected for humanization of cH36 LC FR2. The following mutations were made in cH36 LC FR1 to match the amino acid sequence of a human kappa light chain variable region with a Kabat Database ID No. 005191: Q11→L, L15→V, E17→D, S18→R. One mutation Q37→L was made in cH36 LC FR2 to match the amino acid sequence of a human kappa light chain variable region with a Kabat Database ID No. 019308 (see Table 1A for sequence information).

The amino acid sequence of a human kappa light chain variable region with a Kabat Database ID No. 038233 was selected for humanization of cH36 LC FR3. The amino acid sequence of a human kappa light chain variable region with a Kabat Database ID No. 004733 was selected for humanization of cH36 LC FR4. The following mutations were made in cH36 LC FR3 to match the amino acid sequence of a human kappa light chain variable region with a Kabat Database ID No. 038233: K70→D, K74→T, A80→P, V84→A, N85→T. Two mutations A100→Q and L106→I were made cH36 LC FR4 to match the amino acid sequence of a human kappa light chain variable region with a Kabat Database ID No. 004733 (see Table 1B for sequence information).

(ii). Selection of Human IgG Heavy Chain Variable Region Frameworks

The amino acid sequence in each of the frameworks of cH36 HC was compared with the amino acid sequence in the corresponding FR in human IgG heavy chain variable region in Kabat Database. The best-fit FR was selected based on the three criteria described above.

The amino acid sequence of a human IgG heavy chain variable region with a Kabat Database ID No. 000042 was selected for humanization of cH36 HC FR1. The amino acid sequence of a human IgG heavy chain variable region with a Kabat Database ID No. 023960 was selected for humanization of cH36 HC FR2. The following mutations were made in cH36 HC FR1 to match the amino acid sequence of a human IgG heavy chain variable region with a Kabat Database ID No. 000042: E1→Q, Q5→V, P9→G, L11→V, V12→K, Q19→R, T24→A. Two mutations H41→P and S44→G were made in cH36 HC FR2 to match the amino acid sequence of a human IgG heavy chain variable region with a Kabat Database ID No. 023960 (see Table 2A for sequence information).

The amino acid sequence of a human IgG heavy chain variable region with a Kabat Database ID No. 037010 was selected for humanization of cH36 HC FR3. The amino acid sequence of a human IgG heavy chain variable region with a Kabat Database ID No. 000049 was selected for humanization of cH36 HC FR4. The following mutations were made in cH36 HC FR3 to match the amino acid sequence of a human IgG heavy chain variable region with a Kabat Database ID No. 037010: S76→T, T77→S, F80→Y, H82→E, N84→S, T87→R, D89→E, S91→T. One mutation L113→V was made in cH36 HC FR2 to match the amino acid sequence of a human IgG heavy chain variable region with a Kabat Database ID No. 000049 (see Table 2B for sequence information).

Table 1A and 1B: Comparison of cH36 and Human Light Chain (LC) FR Sequences

TABLE 1A

| FR1 (23 AA) | FR2 (15 AA) | Names |
|---|---|---|
| 1      10      20 | 35      48 | |
| (SEQ ID NOS 11 & 12) | | |
| DIQMTQSPASQSASLGESVTITC | WYQQKPGKSPQLLIY | cH36-LC |
| (SEQ ID NOS 13 & 14) | | |
| DIQMTQSPAS__L__SAS__VG__D__R__VTITC | WY__L__QKPGKSPQLLIY | Human-LC |

TABLE 1B

| FR3 (32 AA) | FR4 (10 AA) | Names |
|---|---|---|
| 57     60          70          80      86 | 98        107 | |
| (SEQ ID NOS 15 & 16) | | |
| GVPSRFSGSGSGTKFSFKISSLQAEDFVNYYC | FGAGTKLELK | cH36-LC |
| | | |
| (SEQ ID NOS 17 & 18) | | |
| GVPSRFSGSGSGT<u>D</u>FSF<u>T</u>ISSLQ<u>P</u>EDF<u>A</u>TYYC | FG<u>Q</u>GTKLE<u>I</u>K | Human-LC |

Table 2A and 2B: Comparison of cH36 and Human Heavy Chain (HC) FR Sequences

TABLE 2A

| FR1 (30 AA) | | |
|---|---|---|
| 1                                     10           20 | | |
| (SEQ ID NOS 19 & 20) | | |
| EIQLQQSGPELVKPGASVQVSCKTSGYSFT | WVRQSHGKSLEWIG | cH36-HC |
| | | |
| (SEQ ID NOS 21 & 22) | | |
| <u>Q</u>IQL<u>V</u>QSG<u>GE</u>VKKPGASV<u>R</u>VSCK<u>A</u>SGYSFT | WVRQS<u>P</u>GK<u>G</u>LEWIG | Human-HC |

TABLE 2B

| FR3 (32 AA) | FR4 (11 AA) | Names |
|---|---|---|
| 67       75        85         95 | 107      117 | |
| (SEQ ID NOS 23 & 24) | | cH36- |
| KATLTVDKSSTTAFMHLNSLTSDDSAVYFCAR | WGQGTTLTVSS | HC |
| | | |
| (SEQ ID NOS 25 & 26) | | Human- |
| KATLTVDKS<u>TSTAY</u>M<u>EL</u>S<u>SLRSED</u>TAVYFCAR | WGQGTT<u>V</u>TVSS | HC |

Once the decisions on the desired human frameworks were made, the following three techniques were used to achieve the desired amino acid substitutions in both the light and heavy chains: (1) Regular PCR was used for cloning, to introduce cloning or diagnostic endonuclease sites, and to change amino acid residues located at the ends of the variable regions. (2) PCR-based mutagenesis was used to change multiple amino acid residues at a time, especially when these residues were in the middle of the variable regions. (3) Site directed mutagenesis was used to introduce one or two amino acid substitutions at a time. Site directed mutagenesis was done following the protocol described in Stratagene's "QuickChange Site-Directed Mutagenesis Kit" (Catalog #200518).

After each step, the partially humanized clones were sequenced and some of these variable regions were later cloned into expression vectors. The plasmid tKMC180 was used to express LC mutants, and pJRS 355 or pLAM 356 vector was used to express HC mutants as IgG1 or IgG4, respectively. Some of these clones were then combined and expressed transiently in COS cells to determine the expression levels by ELISA.

The final fully humanized forms of the anti-TF heavy and light variable regions were cloned into what is sometimes referred to herein as a "mega vector" and transfected into CHO and NSO cells for IgG expression. Stable cell lines were then used to produce amounts of humanized anti-TF sufficient for analysis. The resulting humanized versions are 100% human in origin (when the CDR sequences are not considered). The humanized IgG4 kappa version is designated hFAT humanized IgG Four Anti-Tissue Factor antibody) and the IgG1 kappa version is designated hOAT (humanized IgG One Anti-Tissue Factor antibody). These fully humanized versions of cH36 are intended for treating chronic indications, such as thrombosis, cancer and inflammatory diseases.

C. Humanization of Anti-TF Antibody Heavy Chain

1. PCR amplification and cloning into pGem T-easy of anti-TF mAb cH36 heavy chain (HC) variable region were performed using plasmid pJAIgG4TF.A8 (an expression vector for chimeric H36) as template and primers TFHC1s2 and TFHC1as2. Primer TFHC1s2 introduced a BsiW1 site upstream of the initiation codon and also an amino acid change E1 to Q in framework (FR)1. Primer TFHC1as introduced an amino acid change L113 to V in FR4. This step resulted in the construct HC01.

2. PCR-based mutagenesis using the previous construct (HC01) and the following four primers generated construct HC02. Upstream PCR used primers TFHC1s2 and TFHC7 as. Downstream PCR used primers TFHC7s and TFHC1as2. Overlap PCR using upstream and downstream PCR products as templates and with primers TFHC1s2 and TFHC1as2 yielded HC02. The use of primers TFHC7s and TFHC7 as introduced two amino acid changes in FR2: H41 to P and S44 to G.

3. PCR-based mutagenesis using HC02 as template and the following four primers generated construct HC03. Upstream PCR used primers TFHC1s2 and TFHC5 as2. Downstream PCR used primers TFHC5s and TFHC1as2. PCR using upstream and downstream PCR products as templates and with primers TFHC1s2 and TFHC1as2 yielded HC03. The use of primers TFHC5s and TFHC5 as2 introduced three amino acid changes in FR3: T87 to R, D89 to E, and S91 to T. A Bgl II site was also introduced at position. 87.

4. PCR amplification was performed using primers TFHC2s and TFHC3 as and HC03 in pGem as template. TFHC2s sits upstream of the cloning site in pGem. TFHC3 as sits in framework 3 and introduces two amino acid changes in FR3: H82 to E and N84 to S. The resulting PCR band was cloned into pGem and then the proper size insert was digested with BsiW1 and Bgl II. Cloning of this fragment into HC03 yields HC04.

5. PCR-based mutagenesis using HC04 as template and the following primers resulted in HC05. Upstream PCR used primers TFHC1s2 and TFHC6 as. Downstream PCR used primers TFHC6s and TFHC1as2. Mutagenic PCR using upstream and downstream PCR products as templates and with primers TFHC1s2 and TFHC1as2 yielded HC05. This step introduced the following amino acid changes in FR3: S76 to T, T77 to S, and F80 to Y.
6. PCR-based mutagenesis using HC05 as template and the following four primers generated HC06. Upstream PCR used primers TFHC2s and TFHC2 as2. Downstream PCR used primers TFHC3s2 and TFHC1as2. Amplification using TFHC2 as2 introduced an amino acid change in FR1: P9 to G. Primer TFHC3s2 changes Q19 to R and T24 to A. PCR using upstream and downstream PCR products as template and with primers TFHC1s2 and TFHC1as2 yielded HC06.
7. A point mutation from I to M in position 2 of FR1 was spontaneously introduced during construction of HC06. PCR amplification using HC06 as template and TFHC1s3 and TFHC1as2 as primers, corrected this erroneous substitution and also introduced an amino acid. change in FR1: Q5 to V. The resulting construct was HC07.
8. Construct HC08 was made by PCR-based mutagenesis using HC07 as template and the following primers. TFHC2s and TFHC2 as3 were used for the upstream product. The downstream product was previously amplified using TFHC1s3 and TFHC1as2 (see step 7). The use of primer TFHC2 as3 introduced two amino acid changes in FR1: L11 to V and V12 to K. A spontaneous point mutation resulted in a F to L change at position 64 in CDR2. Further screening and sequencing yielded construct HC08R1, which has the correct sequence of F at position 64 in CDR2.
9. Two constructs, HC11 and HC12, were generated by site-directed mutagenesis from HC07. Two complementary primers TFHC8sP and TFHC8asP were used along with HC07 as template to produce HC11 which contains three amino acid changes in FR1: G9 P, L11 to V, and V12 to K. Then, HC11 was methylated and column purified for the next round of site directed mutagenesis. PCR using HC11 as a template and the complementary primers TFHC9sL and TFHC0asL generated HC12 which has a mutation from V11 to L in FR1.
10. Construct HC09 was derived from HC12 by performing PCR using HC12 as a template and the complementary primers TFHC10sK and TFHC10asK. HC09 contains an amino acid change: K12 to V in FR1.
11. Construct HC10 was made from HC09. PCR using HC09 as a template and the complementary primers LV-1 and LV-2 resulted in the generation of HC10, which contains a mutation from L11 to V in FR1.

After each mutation step, the partially humanized or fully humanized clones were sequenced and some of these variable regions were later cloned into expression vectors. pJRS 355 or pLAM 356 vector was used to express HC mutants fused to Fc of human IgG1 or IgG4.

FIG. 7A summarizes steps 1-11 and shows incremental amino acid changes introduced into FR1-4. Except HC08, all other heavy chain mutants and cH36 contain F at position 64 in CDR2. HC08 has a mutation from F to L at position 64. FIGS. 7B-D show the heavy chain CDR sequences.
Primers Used for Heavy Chain Humanization TFHC1s2 (SEQ ID NO: 27)
5' TTTCGTACGTCTTGTCCCAGATCCAGCTGCAGCAGTC 3'

TFHC1as2 (SEQ ID NO: 28)
5' AGCGAATTCTGAGGAGACTGTGACAGTGGTGCCTTGGCCCCAG 3'

TFHC7s (SEQ ID NO: 29)
5' GTGAGGCAGAGCCCTGGAAAGGGCCTTGAGTGGATTGG 3'

TFHC7as (SEQ ID NO: 30)
5' CCAATCCACTCAAGGCCCTTTCCAGGGCTCTGCCTCAC 3'

TFHC5s (SEQ ID NO: 31)
5' GCATCTCAACAGCCTGAGATCTGAAGACACTGCAGTTTATTTCTGT G 3'

TFHC5as2 (SEQ ID NO: 32)
5' CTGCAGTGTCTTCAGATCTCAGGCTGTTGAGATGCATGAAGGC 3'

TFHC3as (SEQ ID NO: 33)
5' GTCTTCAGATCTCAGGCTGCTGAGCTCCATGAAGGCTGTGGTG 3'

TFHC2s (SEQ ID NO: 34)
5' TACGACTCACTATAGGGCGAATTGG 3'

TFHC6s (SEQ ID NO: 35)
5' CTGTTGACAAGTCTACCAGCACAGCCTACATGGAGCTCAGCAG 3'

TFHC6as (SEQ ID NO: 36)
5' CTGCTGAGCTCCATGTAGGCTGTGCTGGTAGACTTGTCAACAG 3'

TFHC2as2 (SEQ ID NO: 37)
5' GCACTGAAGCCCCAGGCTTCACCAGCTCACCTCCAGACTGCTGCAG C 3'

TFHC3s2 (SEQ ID NO: 38)
5' CTGGGGCTTCAGTGCGGGTATCCTGCAAGGCTTCTGGTTACTCATT CAC 3'

TFHC1s3 (SEQ ID NO: 39)
5' TCGTACGTCTTGTCCCAGATCCAGCTGGTGCAGTCTGGAGGTGAG C 3'

TFHC2as3 (SEQ ID NO: 40)
5' GCACTGAAGCCCCAGGCTTCTTCACCTCACCTCCAGACTGCACC 3'

TFHC9sL (SEQ ID NO: 41)
5' GCAGTCTGGACCTGAGCTGAAGAAGCCTGGGG 3'

TFHC9asL (SEQ ID NO: 42)
5' CCCCAGGCTTCTTCAGCTCAGGTCCAGACTGC 3'

TFHC8sP (SEQ ID NO: 43)
5' GCTGGTGCAGTCTGGACCTGAGGTGAAGAAGCC 3'

TFHC8asP (SEQ ID NO: 44)
5' GGCTTCTTCACCTCAGGTCCAGACTGCACCAGC 3'

TFHC10sK (SEQ ID NO: 45)
5' GCAGTCTGGACCTGAGCTGGTGAAGCCTGGGGCTTC 3'

TFHC10asK (SEQ ID NO: 46)
5' GAAGCCCCAGGCTTCACCAGCTCAGGTCCAGACTGC 3'

LV-1 (SEQ ID NO: 47)
5' CAGTCTGGACCTGAGGTGGTGAAGCCTGGG 3'

LV-2 (SEQ ID NO: 48)
5' CCCAGGCTTCACCACCTCAGGTCCAGACTG 3'

D. Humanization of Anti-TF Antibody Light Chain
1. PCR amplification was performed using plasmid pJAIgG4TF.A8 (an expression vector for chimeric H36) as template and primers TFLC1s2.1 and TFLC1as2. This step introduced a cloning site, AgeI, upstream of the coding region. It also introduced the L106I mutation in FR4. This step yielded the construct LC03.

2. Site-directed mutagenesis was performed using complementary primers TFLC5s and TFLC5 as and LC03 as template. This step introduced the mutation Q37L in FR2 and added a PstI site for diagnostic purposes. This new construct is named LC04.
3. PCR amplification was performed using LC04 as template and primers TFHC2s and TFLC2as1. This step generated Fragment A that will be used in step 6. This step introduced Q11L and L15V mutations in FR1.
4. PCR amplification was performed using LC04 as template and primers TFLC1s2.1 and TFLC1 asR. This introduced the KpnI site at the end of LC variable region. Cloning of this PCR fragment into pGEM yields pGEM04K that will be used in step 6.
5. PCR amplification was performed using LC40 as template and primers TFLC2s and TFLC4 as. This step generated Fragment C that will be used in step 6. Three mutations E17D, S18R in FR1 and A100Q in FR4 were introduced in this step.
6. PCR-based mutagenesis using Fragment A and Fragment C as templates and primers TFHC2s and TFLC4 as yielded Fragment D. Cloning of Fragment D into pGEM04K yielded the construct LC05.
7. PCR amplification was performed using pGEM04K as template and primers TFLC1s2.1 and TFLC4 as. This step generated Fragment H, which is then cloned into pGEM04K. This introduced the A100Q mutation in FR4 and the construct is named LC06.
8. PCR amplification was performed using LC06 as template and primers TFLC1s2.1 and TFLC3 as. This step generated Fragment I that will be used in step 10. This introduced the K70D and the K74T mutations in FR3.
9. PCR amplification was performed using LC06 as template and primers TFLC3s2 and TFLC4 as. This step generated Fragment F that will be used in step 10. This introduced the A80P mutation in FR3.
10. PCR using Fragment I and Fragment F as templates and primers TFLC1s2.1 and TFLC4 as yielded Fragment J. Cloning of Fragment J into pGEM yielded the construct LC07.
11. Site-directed mutagenesis was conduced using complementary primers TFLC08sds and TFLC08sdsa and LC07 as template. This step introduced the mutations V84A and N85T in FR3. This construct is named LC08.
12. The AgeI to EcoO109I fragment from LC05 containing the mutations Q11L, L15V, E17D, S18R and Q37L is cloned into LC08. This yielded the construct LC09.
13. Site-directed mutagenesis was conduced using LC09 as template and the complementary primers LC105 and LC103. This step introduced the T85N mutation in FR3 and yielded the construct LC10.
14. Site-directed mutagenesis was conducted using LC10 as template and the complementary primers LC115 and LC113. This step introduced the D70K mutation in FR3. This yielded the construct LC11.
15. Site-directed mutagenesis was conducted using LC11 as template and the complementary primers LC125a and LC123a. This step introduced the K42Q mutation in FR2. This yielded the construct LC12.

After each mutation step, the partially humanized or fully humanized LC clones were sequenced and some of these variable regions were later cloned into expression vector tKMC180.

FIG. 6A summarizes steps 1-15 and shows incremental amino acid changes introduced into FR1-4 of the light chain. FIGS. 6B-D show the light chain CDR sequences.

Oligonucleotide Primers Used for Light Chain Humanization

TFLC1as2: (SEQ ID NO: 49)
5' TTCGAAAAGTGTACTTACGTTTGATCTCCAGCTTGGTCCCAG 3'

TFLC1s2.1: (SEQ ID NO: 50)
5' ACCGGTGATATCCAGATGACCCAGTCTCC 3'

TFLC5s: (SEQ ID NO: 51)
5' GGTTAGCATGGTATCTGCAGAAACCAGGG 3'

TFLC5as: (SEQ ID NO: 52)
5' CCCTGGTTTCTGCAGATACCATGCTAACC 3'

TFHC2s: (SEQ ID NO: 53)
5' TACGACTCACTATAGGGCGAATTGG 3'

TFLC2as1: (SEQ ID NO: 54)
5' CCACAGATGCAGACAGGGAGGCAGGAGACTG 3'

TFLC1asR: (SEQ ID NO: 55)
5' TTCGAAAAGTGTACTTACGTTTGATCTCCAGCTTGGTACCAGCACCG AACG 3'

TFLC2s: (SEQ ID NO: 56)
5' CCTGTCTGCATCTGTGGGAGATAGGGTCACCATCACATGC 3'

TFLC4as: (SEQ ID NO: 57)
5' GATCTCCAGCTTGGTACCCTGACCGAACGTGAATGG 3'

TFLC3as: (SEQ ID NO: 58)
5' GTAGGCTGCTGATCGTGAAAGAAAAGTCTGTGCCAGATCC 3'

TFLC3s2: (SEQ ID NO: 59)
5' CACGATCAGCAGCCTACAGCCTGAAGATTTTGTAAATTATTACTGT C 3'

TFLC08sds: (SEQ ID NO: 60)
5' GCAGCCTACAGCCTGAAGATTTTGCAACTTATTACTGTCAACAA G 3'

TFLC08sdsa: (SEQ ID NO: 61)
5' CTTGTTGACAGTAATAAGTTGCAAAATCTTCAGGCTGTAGGCTG C 3'

LC105: (SEQ ID NO: 62)
5' CAGCAGCCTACAGCCTGAAGATTTTGCAAATTATTACTGTCAAC 3'

LC103: (SEQ ID NO: 63)
5' GTTGACAGTAATAATTTGCAAAATCTTCAGGCTGTAGGCTGCTG 3'

LC115: (SEQ ID NO: 64)
5' CAGTGGATCTGGCACAAAGTTTTCTTTCACGATCAGCAGC 3'

LC113: (SEQ ID NO: 65)
5' GCTGCTGATCGTGAAAGAAAACTTTGTGCCAGATCCACTG 3'

LC125a: (SEQ ID NO: 66)
5' CTGCAGAAACCAGGGCAATCTCCTCAGCTCCTG 3'

LC123a: (SEQ ID NO: 67)
5' CAGGAGCTGAGGAGATTGCCCTGGTTTCTGCAG 3'

FIG. 8 shows hOAT (humanized cH36-IgG1) constant region sequences of the light (FIG. 8A) and heavy chain (FIG. 8B). FIG. 9 shows hFAT (humanized cH36-IgG4) constant region sequences of the light (FIG. 9A) and heavy chain (FIG. 9B). In each figure, the last amino acid residue of the framework 4 (FR4) variable region is connected to the first amino acid residue of the constant region for hOAT and hFAT.

Example 2

Expression and Purification of Humanized Anti-TF Antibodies

Figures 3A, 3B:
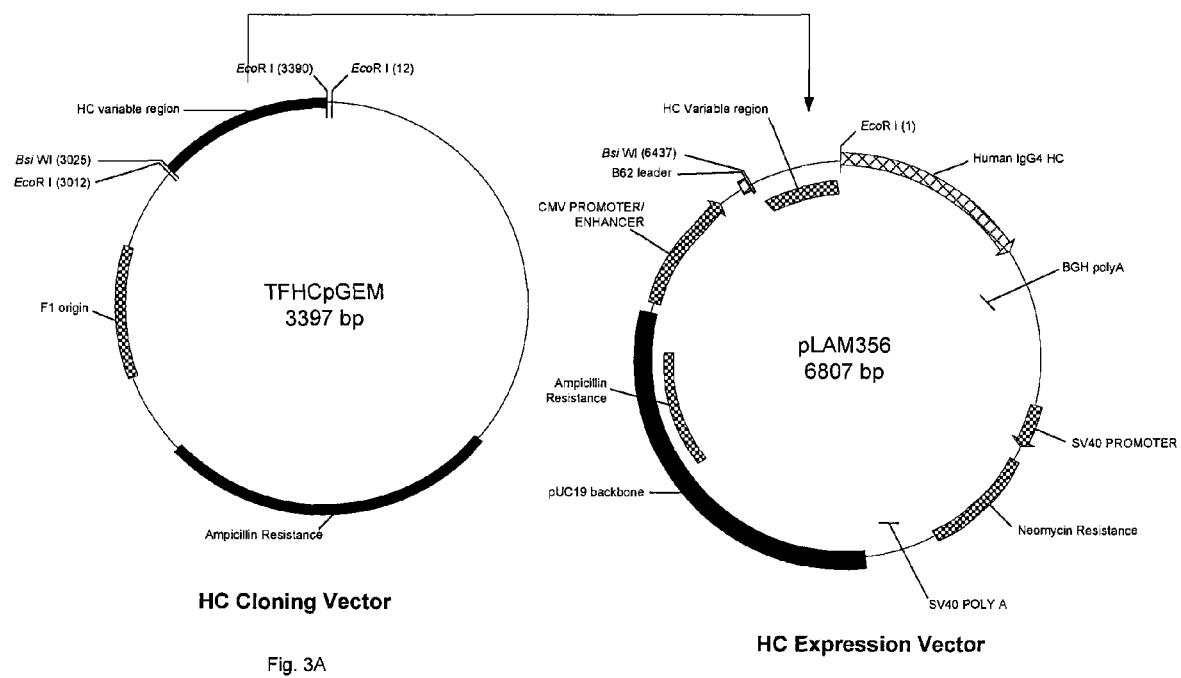
FIGS. 3A-B are drawings showing human IgG4-cH36 HC variable region cloning and expression vectors. HC cloning vector (3C) and HC expression vector (3D).
Figures 4A, 4B:
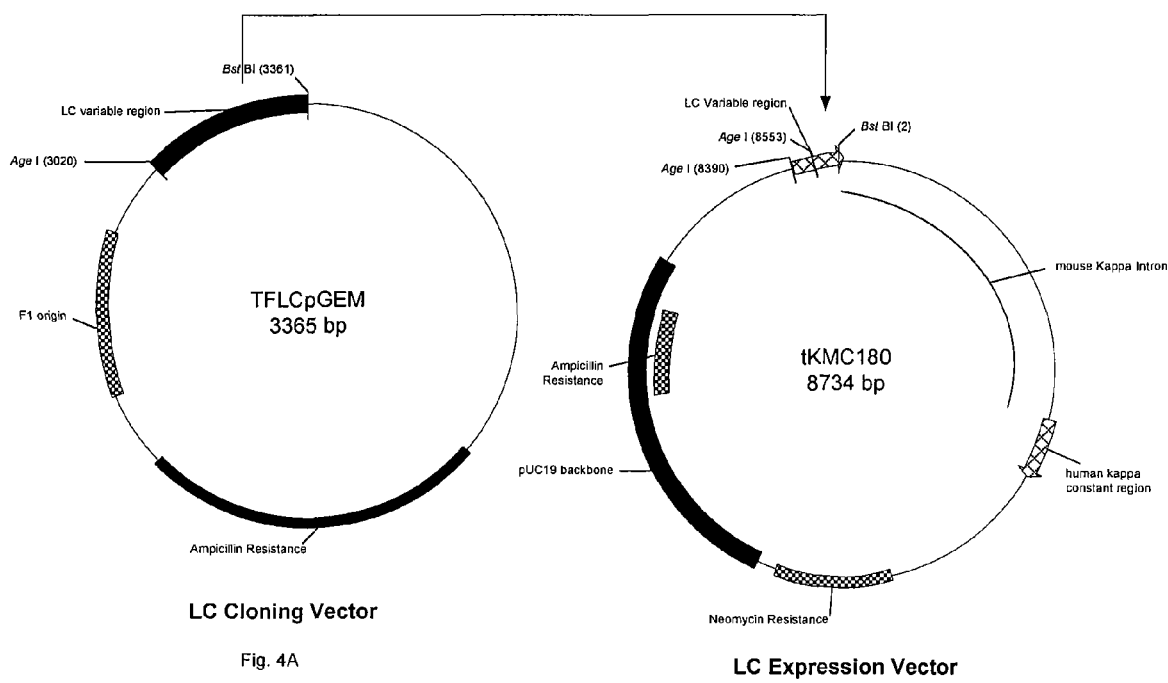
FIGS. 4A-B are drawings showing cH36 LC variable region cloning and expression vectors. LC cloning vector (4A) and LC expression vector (4B).

The partially humanized or fully humanized LC and HC clones were cloned into expression vectors. The plasmid tKMC180 (see FIGS. 4A-B) was used to express LC mutants fused to human kappa chain, and pJRS 355 (see FIGS. 2A-B) or pLAM 356 (see FIGS. 3A-B) vector was used to express HC mutants fused to Fc of human IgG1 or IgG4. Some combinations of the HC and LC clones were then co-transfected into COS cells. The transiently expressed IgGs in COS cells were assayed for the whole IgG production and binding to TF by ELISA.

Figure 5:
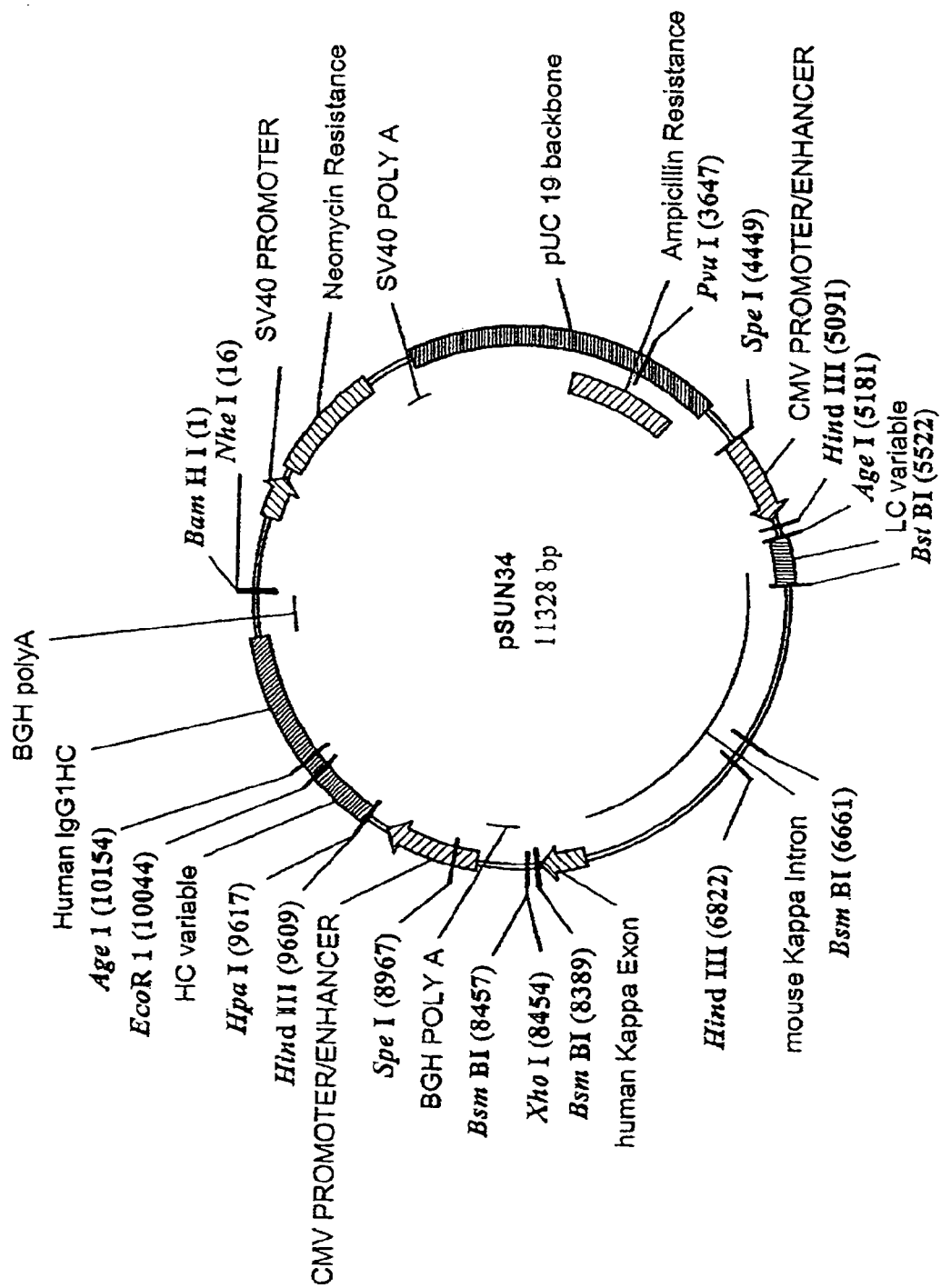
FIG. 5 is a drawing showing a plasmid map of humanized anti-TF IgG1 antibody expression vector (pSUN 34).

The final fully-humanized forms of the anti-TF heavy and light variable regions (combination of HC08 and LC09) were cloned into Sunol's Mega expression vector (pSUN34, see FIG. 5) and transfected into CHO and NS0 cells for IgG expression. Stably transfected cell lines producing the IgG4κ or IgG1κ humanized anti-TF antibody were cloned. The selected stable cell lines were then used to produce amounts of humanized anti-TF sufficient for analysis. The resulting humanized versions are approximately 95% human in origin (the CDR sequences are not considered). The humanized IgG4 kappa version is designated HFAT (humanized IgG Four Anti-Tissue Factor antibody) and the IgG1 kappa version is designated hOAT (humanized IgG One Anti-Tissue Factor antibody). These fully humanized versions of cH36 are intended for treating chronic indications, such as cancer and inflammatory diseases.

One of the NS0 cell lines (OAT-NSO-P10A7) that expresses hOAT (combination of HC08 and LC09) was thawed and extended in 10 mL of IMDM medium supplemented with 10% FBS in a 15 mL tube and centrifuged. The cell pellet was resuspended in 10 mL of fresh media and passed to a T25 flask and incubated at 37° C. in 5% $CO_2$. In order to prepare a sufficient number of cells to inoculate a hollow fiber bioreactor, the cells were expanded to obtain a total of $6 \times 10^8$ cells. A bioreactor was set up as per manufacturer's instruction manual. The harvested cells were pelleted and resuspended in 60 mL of IMDM containing 35% FBS and injected into the extracapillary space of the bioreactor. Concentrations of glucose and lactate were monitored daily and the harvest material was centrifuged and pooled. The harvested material was tested for anti-TF antibody concentrations by ELISA assay. The pooled sample containing anti-TF antibody (hOAT) were then purified and analyzed as described below.

A. rProtein A Sepharose Fast Flow Chromatography

Recombinant humanized anti-TF monoclonal antibody consists of two light and two heavy chains. Heavy chain is a fusion of mouse variable region (unaltered or humanized as described above) and human IgG1 or IgG4 Fc domain, while light chain contains mouse variable region (unaltered or humanized as described above) and human κ domain. It is well established that human IgG Fc region has high affinity for Protein A or recombinant Protein A (rProtein A).

Harvest pools containing humanized anti-TF antibody (hOAT) were adjusted to pH 8.0±0.1 by adding 0.08 ml of 1 M Tris-HCl, pH 8.0 per ml of sample. Then the sample is filtered through low protein-binding 0.22 micron filters (e.g., Nalgene sterile disposable tissue culture filter units with polyethersulfone membrane from Nalge Nunc International, Cat. No. 167-0020). Following sample application, rProtein A column (from Pharmacia) is washed with 5 bed volumes of 20 mM Tris-HCl, pH 8.0 to remove unbound materials such as media proteins. Since the harvest medium contains high content of bovine serum, a stepwise pH gradient wash was used to remove bovine IgG from the column. The stepwise pH gradient was achieved by increasing the relative percentage of Buffer B (100 mM acetic acid) in Buffer A (100 mM sodium acetate). A typical pH stepwise wash employed 20%, 40%, and 60% Buffer B. Elute the column with 100% Buffer B and collect fractions based on $A_{280}$. The pooled fractions were adjusted to pH 8.5 with addition of 1 M Tris base.

B. Q Sepharose Fast Flow Chromatography

Anion ion exchange chromatography is very effective in separating proteins according to their charges. The eluted and pH-adjusted sample from rProtein A column was diluted with two volumes of water, and the pH is checked and adjusted to 8.5. The sample was then loaded to a 5 ml (1.6×2.5 cm) Q Sepharose Fast Flow equilibrated with 20 mM Tris-HCl, pH 8.5 and the column washed with (1) 5 bed volumes of 20 mM Tris-HCl, pH 8.5; and (2) 4 bed volumes of 20 mM Tris-HCl, pH 8.5 containing 100 mM NaCl. The IgG protein was then eluted with bed volumes of 20 mM Tris-HCl, pH 8.5 containing 500 mM NaCl. The protein peaks were pooled and buffer-exchanged into PBS using ultrafiltration device.

Using the same transfection, cell culture, and purification methods, hFAT was also produced and purified.

Example 3

Properties of Humanized Anti-TF Antibodies

A. Inhibition of TF Function by Humanized Anti-TF Antibody

One of the key properties of anti-TF antibodies is its ability to inhibit tissue factor-initiated blood coagulation. The purified hOAT and hFAT were measured for their ability to inhibit TF activity in a standard PT assay. PT assay is widely used to measure tissue factor-dependent blood clotting times. The principal of this assay is that tissue factor (TF) forms complex with factor VIIa in plasma. This complex then activates factor X to FXa; FXa then converts prothrombin to thrombin in the presence of factor Va and phospholipids. Thrombin eventually leads to formation of a blood clot. In standard PT assays, lipidated TF is added to plasma to initiate blood coagulation and the clotting is recorded by an Organon Teknika Coag-A-Mate Coagulation Analyzer or equivalent.

The anti-TF antibody, H36, inhibits human TF activity by a unique mechanism. It binds to TF (free or in complex with factor VIIa) in such a way that factor X and 1× binding to TF:VIIa complex is prohibited, thus FX and FIX activation by TF:VIIa is blocked (see U.S. Pat. No. 5,986,065). In PT tests, the prolongation of clotting times by anti-TF antibody added into human plasma is a clear indication that this TF-dependent coagulation is inhibited. The clotting time is related to the amount of TF activity. A TF standard curve is generated by measuring PT clotting times of serially diluted TF. From the data of TF standard curve, the inhibition of TF activity by anti-TF antibody is determined.

Reagents for standard PT assay: Innovin (Cat No 68100-392) as a recombinant human TF source and Ci-Trol Coagulation Control, Level I (Cat No 68100-336) as a human plasma source are obtained from VWR. PT Assay Method: PT test is performed at 37° C. using a Coagulation Analyzer. PT reaction is initiated by adding 0.2 ml of lipidated recombinant human tissue factor (e.g., Innovin) into 0.1 ml of human plasma (Ci-Trol Control Level I) containing 0.01 ml buffer (50 mM Tris-HCl, pH 7.5, 0.1% BSA) or anti-TF antibody.

1. Add purified water to a vial of Innovin according to manufacturer's instruction. Warm the reagent to 37° C. The reagent is stable for a few days if stored at 4-8° C.
2. Add 1 ml purified water to each vial of Ci-Trol. Mix to solubilize. If more one vials are used, combine them into one container (e.g., a 10 ml test tube). 1 ml Ci-Trol can run 5 assays (each assay uses 2×0.1 ml=0.2 ml). Ci-Trol can be stored on ice and last for a few hours.
3. From anti-TF antibody stock, make a series of anti-TF antibody solutions (200 nM to 1600 nM) with 50 mM Tris-HCl, pH 7.5, 0.1% BSA
4. Add 10 µl of 50 mM Tris-HCl, pH 7.5, 0.1% BSA or 10 µl of diluted anti-TF antibody to each well of the twin-well cuvette that contains 0.1 ml of Ci-Trol. Use a pipette with 0.1 ml tip to mix each well. Make sure no air bubbles are in the well. Following mixing anti-TF (or buffer) with plasma (Ci-Trol), measure clotting times within 10 min by adding 0.2 ml of Innovin to the plasma.
5. For TF standard curve, first dilute Innovin (100% TF) to 20%, 10%, 5% and 2.5% with 50 mM Tris-HCl, pH 7.5, 0.1% BSA. Then PT assays were performed as in Step 4 but using diluted Innovin samples.

Table 3 is the summary of the effect of cH36, hOAT, and hFAT on PT clotting times. Compared to the data in Table 4, cH36, hFAT, and hOAT showed very potent inhibition of TF function. At a protein concentration of above 12.9 nM, all antibodies achieved about 95% inhibition. The results in Table 3 also indicate that humanization of anti-TF, cH36, by the method described above did not have any significant effect on cH36 inhibitory activity since both hFAT and hOAT showed very similar ability to inhibit TF-dependent blood coagulation as seen for cH36.

TABLE 3

Effect on Prothrombin Times by Chimeric (cH36) and Humanized) Anti-TF Antibodies (hFAT and hOAT)[#]

| Anti-TF Antibody Concentrations | PT Time (in seconds) | | |
|---|---|---|---|
| (nM) in PT Assays | cH36 | hOAT | hFAT |
| 0 | 12.2 | 12.2 | 12.2 |
| 6.45 | 14.9 | nd | nd |
| 9.7 | 17.8 | 16.5 | nd |
| 12.9 | 19.8 | 18.9 | 20.5 |
| 25.8 | 40 | 33.7 | 41.7 |
| 51.6 | 101.3 | 82.1 | 94.8 |

[#]All assays used the same 100% TF activity (concentration) sample as in Table 4.

TABLE 4

Clotting Times and Relative Tissue Factor Activities (Concentrations)

| Relative TF Activities (Concentrations) | PT Clotting Times (Seconds) |
|---|---|
| 100% (neat) | 11.90 |
| 20% | 13.225 |
| 10% | 14.675 |
| 5% | 16.700 |
| 2.5% | 20.000 |

B. Determination of Affinity Constants

The affinity of humanized anti-TF antibody for TF was determined by surface plasmon resonance (BIAcore from Pharmacia Biosensor) with recombinant human tissue factor covalently immobilized on a CM5 sensor chip. The affinity constants were the average data calculated from four anti-TF monoclonal antibody concentrations (0.125 nM, 0.25 nM, 0.5 nM, and 1 nM) by the BIAcore computer software. The results in Table 5 indicate that humanization of anti-TF, cH36, by the method described above did not have any significant effect on cH36 affinity for TF since both cH36 and hFAT have similar affinity for human TF.

TABLE 5

Apparent Affinity and Dissociation Constants of Anti-TF Antibodies

| Anti-TF Antibody | Apparent $K_a$ ($M^{-1}$) | Apparent $K_d$ (M) |
|---|---|---|
| H36 | $1.56 \times 10^{10}$ | $6.4 \times 10^{-11}$ |
| cH36 | $7.94 \times 10^{9}$ | $1.26 \times 10^{-10}$ |
| hFAT | $2.99 \times 10^{9}$ | $3.35 \times 10^{-10}$ |

Example 4

Effects of Chimeric Anti-Tissue Factor Monoclonal Antibody on the Formation of Vascular Thrombosis in Chimpanzees The following example shows results of using a particular chimeric antibody of the invention (cH36) to prevent or treat vascular thrombosis and vascular lesion formation. As described above, cH36 is a chimeric antibody comprising mouse antibody light and heavy chains variable domains fused to human antibody light and heavy chain constant domains. In the examples that follows, the cH36 antibody will sometimes be referred to as "Sunol-cH36" or related phrase.

Briefly, TF was exposed by performing an endarterectomy on the femoral artery in chimpanzees. [111]Indium-oxine labeled platelets were deposited at the endarterectomy site in the controls and deposition was significantly reduced with cH36 treatment. As shown below, the vessels from antibody-treated animals were 80% patent whereas the controls were 20% patent 30 days following the endarterectomy. Cutaneous bleeding time and other hematology parameters were not significantly different between the antibody-treated and the controls with the exception of PT times (which are expected to increase due to the presence of the antibody in plasma which is used to perform PT assay with Innovin).

Results of the example show that the cH36 antibody and other antibodies of the invention, particularly humanized TF binding antibodies, should be efficacious in treating patients with cardiovascular diseases due to thrombotic occlusion (such as stable or unstable angina, myocardial infarction (MI), peripheral vascular bypass grafts (PVBG), deep vein thrombosis (DVT) or restenosis following percutaneous transluminal coronary intervention, etc.) and that cH36 is safe with respect to bleeding.

The cH36 antibody was shown to inhibit chimpanzee TF-dependent FX activation, indicating that chimpanzees could be used for in vivo studies.

In the in vivo study, five chimpanzees underwent sequential surgical endarterectomies on the right and left superficial femoral arteries (30 days apart). Autologous platelets were obtained prior to surgery and labeled using [111]Indium-oxine. Each chimpanzee was administered $^{111}$In-labeled platelets intravenously, followed by administration of a placebo or a 1 mg/kg dose of cH36 immediately prior to restoration of flow in the endarterectomized femoral artery. Post-surgical gamma camera imaging of $^{111}$In-platelet deposition at the endarterectomy sites was performed, and the manipulated segments were harvested after 30 days. Each chimpanzee was subjected to the procedure (using placebo or cH36) on the right or left side, and after 30 days the procedure was repeated on the opposite side with the other treatment, so that each animal served as its own control for comparison of platelet deposition and neointimal lesion formation at the sites of endarterectomy with and without the cH36 treatment.

Deposition of autologous $^{111}$In-platelets was measured in five-minute intervals for the first 30 minutes by gamma camera imaging to assess acute vascular thrombosis at the endarterectomy sites. Platelet deposition was significantly decreased with Sunol-cH36 when evaluated at 5 and 30 minutes post-operatively compared to placebo. Since platelets play a pivotal role in thrombus formation, the results indicate that Sunol-cH36 inhibit acute thrombus formation.

Autologous platelets were labeled with 1 mCi $^{111}$Indium ($^{111}$In) oxine as described (Lumsden A B, Kelly A B, Schneider P A, Krupski W C, Dodson T, Hanson S R, Harker L A. "Lasting safe interruption of endarterectomy thrombosis by transiently infused antithrombin peptide D-Phe-Pro-ArgCH2Cl in baboons." *Blood* 1993; 81:1762-1770; Kelly A S, Marzec U M, Krupski W, Bass A, Cadroy Y, Hanson S R, Harker L A. "Hirudin interruption of heparin-resistant arterial thrombus formation in baboons." *Blood* 1991; 77:1006-1012) and re-injected. Gamma camera images were acquired continuously for 30 min in 5 min intervals with a GE 400T scintillation camera (General Electric, Milwaukee, Wis.) or equivalent. The data were stored and analyzed on a Medical Data System A Computer (Medasys Inc., Ann Arbor, Mich.) or equivalent. A medium-energy collimator was placed close to the animal. Measurements of $^{111}$In-activity were corrected for background activity. Activity of a 5-mL whole blood standard was also determined. The activity of the blood standard was also corrected for the small fraction of circulating non-platelet radioactivity to give platelet-associated $^{111}$In-activity per mL of whole blood. The total platelet deposition, including both labeled and unlabeled platelets, was calculated by dividing the deposited CPM by circulating platelet CPM (blood standard) and multiplying by the circulating platelet count (platelets per mL of whole blood) as measured in the blood standard sample.

Vessel injury site to blood ratios were also determined and found to be decreased between control and Sunol-cH36 treated chimpanzees at 5 and 30 minutes post-operatively. At 24 hours, the platelet deposition effects of Sunol-cH36 treatment on vessel injury to blood ratio were less statistically significant. Table 6 and FIGS. 10 and 11 summarize the results of platelet deposition and vessel injury/blood ratio determinations.

Vessel Injury Site/Blood Ratio: Because circulating $^{111}$In platelet activity is cleared continuously through normal physiological mechanisms, platelet accumulation after the acute postoperative period was expressed as the ratio of the $^{111}$In platelet activity at the endarterectomy site to the $^{111}$In platelet activity in the blood. This measurement was independent of the size of the animal, the amount of isotope injected, or the extent to which the isotope may have decayed. Radioactivity values in these calculations refer to platelet activity only, with blood and standard values corrected for the small fraction of nonplatelet activity (see Schneider P A, Hanson S R, Price T M, Harker L A. "Confluent durable endothelialization of endarterectomized baboon aorta by early attachment of cultured endothelial cells," *J. Vasc. Surg.* 11:365-372 [1990]). This vessel injury site/blood ratio was a reproducible measure of thrombus, allowing comparisons at 24 hours post surgery.

TABLE 6

Platelet Deposition and Vessel Injury/Blood Ratio in Chimpanzees

|  | Controls | Sunol-cH36 | p |
|---|---|---|---|
| Platelet Deposition (×10$^9$) | | | |
| At 5 minutes | 1.29 ± 0.42 | 0.36 ± 0.19 | 0.001 |
| At 30 minutes | 1.53 ± 0.93 | 0.37 ± 0.03 | 0.02 |
| Vessel Injury/Blood Ratio | | | |
| At 5 minutes | 5.22 ± 1.98 | 1.62 ± 0.92 | 0.002 |
| At 30 minutes | 6.81 ± 4.29 | 1.29 ± 0.82 | 0.02 |
| At 24 hours | 3.72 ± 1.61 | 2.26 ± 1.47 | 0.17 |
| 30 Day Vessel Patency (%) | 20 | 80 | — |

Values = mean ± standard deviation
p < 0.05 was considered statistically significant The endarterectomized vessel segments were harvested 30 days following surgery to assess longer-term effects of Sunol-cH36. The patency of these vessels was examined and 20% (1/5) of the vessels from the controls were patent, whereas 80% (4/5) of those treated with Sunol-cH36 were patent (Table 6). It was thus concluded that a single dose of Sunol-cH36 at 1 mg/kg contributed significantly to maintaining patency.

The data presented in Table 7 show that the mean bleeding time was 2 minutes in control chimpanzees and 2.5 minutes in the treated chimpanzees, and this difference is not significant. The surgical blood loss was not significantly different for the five control procedures compared to the procedures in which the chimpanzees received the test article. All other hematological markers similarly did not show a difference in values considered significant for controls versus the Sunol-cH36 treated animals (see Table 7).

TABLE 7

Hematology & Other Assessments in Endarterectomized Chimpanzees

|  | Control | Sunol-cH36 | p |
|---|---|---|---|
| Bleeding Time (min) | 2.0 ± 0.2 | 2.5 ± 0.6 | ns |
| Surgical Blood Loss (mL) | 5.9 ± 2.2 | 4.7 ± 3.0 | ns |
| Prothrombin Time (sec) | | | |
| Baseline (pre-surgery) | — | 11.2 ± 0.7 | — |
| 5 min(post RF) | — | 180 ± 40 | 0.0001 |
| 15 min(post RF) | — | 157 ± 52 | 0.0001 |
| 30 min(post RF) | — | 161 ± 60 | 0.0001 |
| 60 min(post RF) | — | 177 ± 27 | 0.0001 |
| 90 min(post RF) | — | 202 ± 7.7 | 0.0001 |
| 24 hours(post RF) | — | 18.1 ± 5.1 | 0.036 |
| Platelet Count (×10$^3$/μL) | | | |
| Baseline | 222 ± 73 | 233 ± 52 | ns |
| Post Surgery | 236 ± 72 | 249 ± 54 | ns |
| 24 hr Post Surgery | 273 ± 61 | 247 ± 90 | ns |
| WBC (×10$^3$/μL) | | | |
| Baseline | 7.8 ± 1.5 | 9.8 ± 1.8 | ns |
| Post Surgery | 16.9 ± 3.2 | 13.9 ± 42 | ns |
| 24 hr Post Surgery | 18.1 ± 4.5 | 19.7 ± 6.5 | ns |
| Antibody Levels by Prothrombin Time Assay (μg/mL) | | | |
| 5 min | 0 | 26.5 ± 5.3 | — |
| 90 min | — | 27.0 ± 2.1 | — |
| 24 hour | — | 8.9 ± 3.7 | — |
| Antibody Levels by Factor x Activation Assay (μg/mL) | | | |
| 5 min | — | 18.8 ± 2.8 | — |
| 90 min | — | 16.5 ± 1.4 | — |
| 24 hour | — | 6.3 ± 0.5 | — |

TABLE 7-continued

Hematology & Other Assessments in Endarterectomized Chimpanzees

|  | Control | Sunol-cH36 | p |
|---|---|---|---|
| Monocyte expression of CD64 (number) | | | |
| Baseline | 7160 ± 1930 | 8600 ± 1800 | ns |
| 90 min | 6900 ± 1700 | 8250 ± 1200 | ns |
| 24 hr | 10600 ± 4900 | 10400 ± 3300 | ns |
| Monocyte expression of tissue factor (ratio of clotting time of unstimulated/stimulated) | | | |
| Baseline | 4.8 ± 0.8 | 4.0 ± 1.2 | 0.3 |
| 90 min | 4.7 ± 0.6 | 1.4 ± 0.1 | 0.005 |
| 24 hr | — | 3.0 ± 0.8 | — |

Values are mean ± standard deviation; n = 5
ns = not significant; p < 0.05 considered statistically significant
— means value not determined
post RF means post restoration of flow following conclusion of endarterectomy See also Smyth et al, (1995) *British Journal of Surgery* 82:588-595 (disclosing other methods of measuring platelet deposition).

Example 5

Effect of Anti-Tissue Factor Antibody (Sunol-cH36) When Administered During the Performance of Skin Flap Surgery on Cynomolgus Monkeys In this example, a large skin flap was surgically elevated and its blood supply limited to a single perforating vessel. In control animals and those treated with lower doses of cH36, the skin flap does not receive adequate perfusion and is slow to heal. At high cH36 doses, the flap showed better perfusion and faster healing. This suggests that cH36 will also improve the outcome of plastic and reconstructive surgery.

A surgical study was also conducted to evaluate treatments with Sunol-cH36 in preventing potential thrombosis of the vascular supply to an abdominal skin flap on cynomolgus monkeys and to determine whether or not excessive bleeding occurs during the procedure according to the dose administered. In this surgical study, five cynomolgus monkeys (1 male and 4 females) underwent a surgical skin flap procedure to induce surgical trauma. The study consisted of 5 groups of 1 animal each. The procedure consisted of raising a rectangular skin paddle, measuring approximately 10 cm by 9 cm, which was elevated from the abdominal wall, limiting blood supply and then reattaching the skin flap. Following ligation of the inferior epigastric artery, the blood supply to the skin flap is limited to vessels on the left side. Group 1 served as a control and received PBS. The remaining groups were administered different doses of Sunol-cH36. Table 8 below, shows the experimental design.

Skin flap viability was evaluated over a 4-week observation period to determine if treatments with the test article have an effect on preventing thrombosis of the vascular supply to the abdominal skin flap on cynomolgus monkeys. Fluorescein was injected and the skin flap examined under ultraviolet light. When the tissue was adequately perfused, the area would fluoresce while areas with poor perfusion appeared dark. For all but one animal (Group 5 animal 5101; 5 mg/kg), the left side (predictably) showed good perfusion following surgery, and the right side typically did not indicate acceptable perfusion, also an expected observation. For some reason, this was reversed in the animal 5101, in that the right side showed acceptable perfusion, rather than the left. This was apparently due to an anatomical variation in this one animal. With time, both sides demonstrated adequate perfusion in all animals; however there seemed to be a trend toward earlier and more complete perfusion as the dose of the test article was increased.

TABLE 8

Study Design for the Skin Flap Study in Cynomolgus Monkeys

| | | Treatment | | | |
|---|---|---|---|---|---|
| Group Number | Animal Number | Test Article | Dose Level (mg/kg) | Dose Concentration (mg/mL) | Dose Volume (mL/kg) |
| 1 | 1001 | PBS | 0 | 0 | 0.5 |
| 2 | 2101 | Sunol-cH36 | 0.04 | 0.515 | 0.08 |
| 3 | 3101 | | 0.2 | | 0.4 |
| 4 | 4101 | | 1.0 | 10.3 | 0.1 |
| 5 | 5101 | | 5.0 | | 0.5 |

Macroscopic and microscopic pathology evaluations were also performed. Evidence of possible continuing compromise to the skin flap was observed for groups 2 and 3 animals (0.04 and 0.2 mg/kg respectively) at the scheduled time of euthanasia, Day 29. The group 2 animal 2101 had a dark area of discoloration in the skin to the left and right skin flap regions. Animal 3101 had a single 6×40 mm area of ulceration in the skin of the cranial portion of the right skin flap region.

Microscopic analysis consisted of examination of four sections from within the skin flap site for all animals: one each from the left and right cranial regions of the flap site, and one each from the left and right caudal regions of the flap site. Table 9 summarizes notable microscopic findings.

Although this study involved only one animal per dose group, there appeared to be a few notable differences in the severity of changes between the skin flap sites of the control animal (left and right), and the skin flap sites of the test article-treated animals. Macroscopic study indicated the degree of edema, erythema, and even necrosis of the right skin flap tended to decrease in severity as the dose of the test article increased. The degree of fluorescein staining of the skin flap tended to increase with increasing dose of Sunol-cH36.

Microscopically, there appeared to be a small but notable, dose-dependent decrease in granulation tissue formation and subintimal vascular smooth muscle proliferation in the panniculus on the left side of the skin flap site in the test article-treated animals compared to the left side of the skin flap site in the control animal. These results suggest that the test article could prevent microthrombosis following procedures of this nature, thus preventing devascularization of a graft.

TABLE 9

Severity* of Selected Microscopic Findings in the Skin Flap Study in Cynomolgus Monkeys

| | Animal Numbers & Dose Level (mg/kg) | | | | |
|---|---|---|---|---|---|
| Tissue/Lesion | 1001 0 | 2101 0.04 | 3101 0.2 | 4101 1.0 | 5101 5.0 |
| Left Skin Flap Site | | | | | |
| Chronic Inflammation | 2.0 | 2.0 | 1.5 | 0.5 | 1.0 |
| Granulation Tissue | 2.0 | 3.0 | 1.5 | 0.5 | 0.5 |
| Subintimal Vascular Proliferation | 2.0 | 2.5 | 1.0 | — | — |
| Hemosiderin Accumulation | 1.0 | 1.0 | 0.5 | — | — |
| Ulceration | — | — | — | — | — |

TABLE 9-continued

Severity* of Selected Microscopic Findings in the Skin Flap Study in Cynomolgus Monkeys

| | Animal Numbers & Dose Level (mg/kg) | | | | |
|---|---|---|---|---|---|
| Tissue/Lesion | 1001 0 | 2101 0.04 | 3101 0.2 | 4101 1.0 | 5101 5.0 |
| Right Skin Flap Site^ | | | | | |
| Chronic Inflammation | 1.0 | 2.0 | 2.5 | 1.0 | 1.0 |
| Granulation Tissue | 2.0 | 3.0 | 2.5 | 2.5 | 1.0 |
| Subimtimal Vascular Proliferation | — | 3.0 | 2.5 | — | 1.5 |
| Hemosiderin Accumulation | — | 0.5 | 2.0 | — | — |
| Ulceration | — | — | 2.0 | — | — |

*The severity of the change is the average severity for the 2 sites examined (cranial and caudal) where 1 is least severe and 3 is most severe. (Average severity equals the summation of severity scores for each section/number of sections affected)
— means microscopic findings not present
^Right skin flap site had perforating vessel ligated All surgical procedures proceeded without incident. There were no observed increases in bleeding. The sponge count procedure described in the study protocol was not performed due to the negligible amounts of blood loss. Except for a slight increase in the white blood cell count during the surgical procedure, there were no hematological changes. The slight increase in white blood cell count is expected due to the traumatic nature of the surgical procedure. No significant change in hematocrit and hemoglobin levels was detected. Hematology results showed several red blood cell parameters to be outside of the expected ranges in groups 2 and 3. These variations were not considered to be test article-related. Table 10 summarizes the hematology parameters and study results.

In all groups, ACT, APTT and fibrinogen levels remained within normal ranges and did not deviate from baseline during the procedure. No change in PT values was observed in groups 1, 2, 3 and 4. However, in the group 5 animal, PT dramatically increased immediately following administration of 5 mg/kg of Sunol-cH36. Prothrombin Times increased from 10.1 seconds to >212 seconds (approximately 5 minutes after dosing). Prothrombin Times slowly decreased from >212 seconds to 198.1 seconds at 15 minutes post administration and to 135.2 seconds at 45 minutes post administration. This elevation was considered an expected Sunol-cH36-related effect.

TABLE 10

Hematology Parameters and Individual Study Results for the Skin Flap Study in Cynomolgus Monkeys

| | | Animal Number/cH36 Dose (mg/kg) | | | | |
|---|---|---|---|---|---|---|
| Parameter | Time Points | 1001 0 (PBS) | 2101 0.04 | 3101 0.2 | 4101 1.0 | 5101 5.0 |
| Total Leukocyte Count (WBC) ($10^3/\mu L$) | Post Catheter | 7.6 | 4.5 | 5.5 | 5.1 | 5.1 |
| | Pre-Treatment | 7.7 | 4.4 | 5.3 | 5.1 | 4.8 |
| | 15 minutes | 7.8 | 4.58 | 5.8 | 5.8 | 4.6 |
| | 30 minutes | 9.7 | 4.8 | 7.8 | 5.4 | 5.2 |
| | 45 minutes | N/A | 5.4 | 8.9 | 6.9 | 5.2 |
| Erythrocyte Count (RBC) ($10^6/\mu L$) | Post Catheter | 6.00 | 3.99 | 4.32 | 6.00 | 6.33 |
| | Pre-Treatment | 5.87 | 4.02 | 4.13 | 6.05 | 6.03 |
| | 15 minutes | 5.70 | 3.96 | 4.10 | 6.09 | 5.94 |
| | 30 minutes | 5.41 | 3.87 | 4.24 | 5.69 | 5.95 |
| | 45 minutes | N/A | 3.83 | 3.87 | 5.77 | 5.55 |
| Hemoglobin Concentration (HGB) (g/dL) | Post Catheter | 11.4 | 10.2 | 11.2 | 10.8 | 11.6 |
| | Pre-Treatment | 11.2 | 10.2 | 10.9 | 10.6 | 11.3 |
| | 15 minutes | 10.5 | 10.0 | 10.7 | 10.9 | 11.2 |
| | 30 minutes | 10.9 | 9.9 | 11.0 | 9.9 | 11.0 |
| | 45 minutes | N/A | 9.9 | 10.7 | 10.6 | 10.5 |
| Hematocrit Value (HCT)$^a$ (%) | Post Catheter | 37.9 | 32.9 | 34.6 | 35.8 | 39.6 |
| | Pre-Treatment | 37.3 | 33.2 | 33.3 | 36.3 | 37.4 |
| | 15 minutes | 36.5 | 32.7 | 32.9 | 36.4 | 36.9 |
| | 30 minutes | 34.5 | 31.9 | 34.0 | 34.1 | 37.0 |
| | 45 minutes | N/A | 31.5 | 30.8 | 34.5 | 34.6 |
| Mean Corpuscular Volume (MCV)$^a$ (fL) | Post Catheter | 63.2 | 82.5 | 80.1 | 59.7 | 62.6 |
| | Pre-Treatment | 63.5 | 82.6 | 80.6 | 60.0 | 62.0 |
| | 15 minutes | 64.0 | 82.6 | 80.2 | 59.8 | 62.1 |
| | 30 minutes | 63.8 | 82.4 | 80.2 | 59.9 | 62.2 |
| | 45 minutes | N/A | 82.2 | 79.6 | 59.8 | 62.3 |
| Mean Corpuscular Hemoglobin (MCH)$^a$ (pg) | Post Catheter | 19.0 | 25.6 | 25.9 | 18.0 | 18.3 |
| | Pre-Treatment | 19.1 | 25.4 | 26.4 | 17.5 | 18.7 |
| | 15 minutes | 18.4 | 25.3 | 26.1 | 17.9 | 18.9 |
| | 30 minutes | 20.1 | 25.6 | 25.9 | 17.4 | 18.5 |
| | 45 minutes | N/A | 25.8 | 27.6 | 18.4 | 18.9 |
| Mean Corpuscular Hemoglobin Concentration (MCHC)$^a$ (g/dL) | Post Catheter | 30.1 | 31.0 | 32.4 | 30.2 | 29.3 |
| | Pre-Treatment | 30.0 | 30.7 | 32.7 | 29.2 | 30.2 |
| | 15 minutes | 28.8 | 30.6 | 32.5 | 29.9 | 30.4 |
| | 30 minutes | 31.6 | 31.0 | 32.4 | 29.0 | 29.7 |
| | 45 minutes | N/A | 31.4 | 34.7 | 30.7 | 30.3 |
| Platelet Count (PLT) ($10^3/\mu L$) | Post Catheter | 377 | 333 | 324 | 252 | 253 |
| | Pre-Treatment | 315 | 318 | 292 | 279 | 220 |
| | 15 minutes | 365 | 332 | 300 | 274 | 233 |
| | 30 minutes | 327 | 325 | 320 | 262 | 227 |
| | 45 minutes | N/A | 315 | 285 | 266 | 175 |

$^a$Calculated value

TABLE 11

Coagulation Parameters & Individual Study Results (Day 1) for the Skin Flap Study in Cynomolgus Monkeys

| Animal Number/ Dose (mg/kg) | Time Points | Activated Clotting Time (ACT) (sec) | Prothrombin Time (PT)[b] (sec) | Activated Partial Thromboplastin Time (APTT) (sec) | Fibrinogen (FIB) (mg/dL) |
|---|---|---|---|---|---|
| 1001 | Post Catheter | 114 | 10.9 | 20.8 | 95 |
| 0 (PBS) | Pre-Treatment | — | 10.7 | 20.3 | 213 |
|  | 15 min post mAb[a] | 37 | — | — | — |
|  | 30 min post mAb | 53 | 11.3 | 20.5 | 170 |
| 2101 | Post Catheter | 124 | 9.8 | 19.8 | 162 |
| 0.04 | Pre-Treatment | 94 | 9.8 | 19.8 | 174 |
|  | 15 min post mAb | 68 | 10.0 | 19.9 | 159 |
|  | 30 min post mAb | 146 | 9.7 | 19.6 | 162 |
|  | 45 min post mAb | 107 | 10.0 | 19.5 | 153 |
| 3101 | Post Catheter | 131 | 9.3 | 21.7 | 170 |
| 0.2 | Pre-Treatment | 150 | 9.4 | 21.7 | 162 |
|  | 15 min post mAb | 97 | 10.4 | 21.2 | 159 |
|  | 30 min post mAb | 107 | 10.6 | 21.2 | 174 |
|  | 45 min post mAb | 108 | 11.2 | 22.1 | 125 |
| 4101 | Post Catheter | 166 | 9.6 | 24.0 | 219 |
| 1.0 | Pre-Treatment | 114 | 9.3 | 23.3 | 209 |
|  | 15 min post mAb | 105 | 9.3 | 23.5 | 198 |
|  | 30 min post mAb | 103 | 9.7 | 24.5 | 338 |
|  | 45 min post mAb | 115 | 10.3 | 26.5 | 117 |
| 5101 | Post Catheter | 155 | 10.1 | 20.7 | 181 |
| 5.0 | Pre-Treatment[b] | 108 | >212 | 22.5 | 184 |
|  | 15 min post mAb | 113 | 198.1 | 20.9 | 198 |
|  | 30 min[a] post mAb | 128 | — | — | — |
|  | 45 min post mAb | not taken | 135.2 | 21.8 | 150 |

[a]Sample clotted
[b]Sample collected 2 minutes post treatment

Example 6

Safety and Effects of Chimeric Anti-Tissue Factor Antibody (Sunol-cH36) on the Formation of Vascular Thrombosis in Cynomolgus Monkeys In this example, an angioplasty induced injury to the arterial vessel was used to expose TF and induce thrombosis using cynomolgus monkeys. The results indicate that cH36 may be reducing thrombotic occlusion. The results also show the safety of the antibody.

The objectives of this study were to determine the safety (and efficacy) of Sunol-cH36 in a model of thrombosis in cynomolgus monkeys. The objectives included a pharmacokinetic aspect, a toxicological component and a pharmacodynamic model in monkeys undergoing a thrombosis-inducing surgical injury.

A pilot study using 2 male cynomolgus monkeys was conducted prior to the start of the main study to establish feasibility of using angioplasty injury as a model for initiation of thrombosis in this species. One animal was dosed intravenously (IV) with cH36 (5 mg/kg) approximately 30 to 45 minutes prior to angioplasty. The second animal was scheduled for dosing with the vehicle; however, this animal did not receive the vehicle. All other procedures were performed in the same manner for both animals. [111]Indium-labeled platelets were injected IV after administration of test article. Animals were then allowed to recover from anesthesia and were observed for approximately 24 hours. Pilot animals were imaged at 1-2 hours post-surgery and at approximately 24 hours, at which time they were euthanized and their injured vessels were perfused and harvested. The segment of the injured vessel was counted in a gamma counter and evaluated grossly for thrombosis. Sections were then fixed for future possible analysis. Based on this pilot study, the main study was conducted.

In the main study, 24 cynomolgus monkeys (12 male and 12 female) were anesthetized and angioplasty was performed. Surgeries were conducted over a four-week period and staggered so that Day 1 was not the same day for all animals. On Day 1, a blood sample was obtained from each animal prior to the surgical procedure for labeling of autologous platelets with [111]Indium. Animals were dosed with the vehicle or test article via a single intravenous slow (<3 min) bolus injection followed by intravenous administration of the autologous platelets (approximately 20 minutes prior to angioplasty). Endothelial denudation via balloon angioplasty in a common iliac artery was then performed. Acute platelet deposition and thrombosis were monitored within the vessel by gamma scintigraphy. Toxicity was assessed by clinical observations, body weight measurements, and cutaneous bleeding times. In addition, blood was collected for hematology, coagulation and serum chemistry analyses, and urine was collected for urinalysis. Blood was also collected to provide plasma for analysis of Sunol-cH36 by ELISA. A comprehensive necropsy was performed on animals that were euthanized as scheduled on Day 15. Protocol-specified organs were weighed and comprehensive tissue collection was performed. Microscopic evaluation was performed on selected tissues from Group 1 and 5 animals. In addition, the angioplasty sites from all animals were evaluated. Table 15 summarizes the design of this study.

This study to determine the safety and efficacy of Sunol-cH36 in monkeys undergoing a thrombosis-inducing surgical injury induced by angioplasty included pharmacokinetic and pharmacodynamic components, which were presented above. The following summarizes the toxicological aspects of Sunol-cH36 in this model of thrombosis in cynomolgus monkeys.

Dose administration for this study was generally performed according to the study design in Table 15. The order of treatment was maintained with test article or vehicle administration first (approximately 30 to 45 minutes prior to angioplasty) and radiolabeled platelets administered second (approximately 20 minutes prior to angioplasty). The intended time frames of administration did not always fall into the ranges specified due to the variable difficulty in accomplishment of the angioplasty procedure.

One control animal (Group 1 female No. 1101) was removed from the study and euthanized on Day 1 without further evaluation. This animal showed unusual anatomy, making the angioplasty difficult, and did not recover from anesthesia. Three other study animals died or were euthanized on Day 1 (Group 2 male No. 2001, 0.04 mg/kg; Group 3 female No. 3102, 0.2 mg/kg; and Group 4 male No. 4001, 1.0 mg/kg). The deaths were all considered anesthesia/procedure related, and all animals were replaced. Complete histopathology was performed for these animals in an attempt to further identify a cause of death.

There were no clinical observations that were considered cH36-related. The most common observations were bruising of the inguinal areas due to blood collection, and unequal pupil diameter that was most likely due to the mechanical trauma of angioplasty. These observations were present in control and cH36-treated groups. Other observations including soft feces, scant feces, and apparent blood in the feces were noted at low incidences only. Some animals showed signs of difficulty breathing and wheezing which was most likely related to intubation trauma. None of these observations appeared to be test article related. One animal (Group 4 female No. 4102) was treated with aminophylline and cefotaxime due to respiratory difficulties after treatment/angioplasty. Macroscopic and microscopic assessment of urine samples collected prior to treatment and prior to necropsy revealed no apparent test article-related effects.

Individual body weights were recorded prior to surgery, on Day 8, prior to necropsy (Day 15) for all animals, and on Day 14 for some animals. Body weights were unaffected by test article treatment and remained constant or fluctuated from week to week.

There were no cH36-related differences in cutaneous bleeding times between groups. Of the 60 bleeding times that were scheduled in the study protocol, 37 times were obtained. Of these, most bleeding times were between one and three minutes; there were 6 bleeding times that were exceptions where bleeding times ranged from 3.5 (n=2), 4.5 (n=2), 6 (n=1), and 7 minutes (n=1). Although only two of the twenty 4-hour cutaneous bleeding times were taken due to technical difficulties and error, there were no bleeding difficulties noted for any animals during attempted blood collection at the 4-hour time point or at any other time during the study. Individual cutaneous bleeding times for this study are provided in Table 13 below along with a chart of the mean bleeding times (with standard deviation) for each dose level in FIG. 12.

There were no test article-related alterations in hematology parameters. There were decreases in red blood cell parameters (red blood cell count [RBC], hemoglobin [HGB] and hematocrit [HCT]), and increases in white blood cells that were present in animals from all groups after treatment with placebo or Sunol-cH36. These alterations showed no

TABLE 12

Cutaneous Bleeding Times in the Angioplasty Study in Cynomolgus Monkeys

| Group No./Dose | Animal Number | Date | Bleeding Time Duration (min:sec) | | |
|---|---|---|---|---|---|
| | | | Pre-Treatment | @ 1.5 hours | @ 4 hours |
| 1 | 1001 | Dec. 19, 2000 | 01:30 | a | 03:30 |
| 0 (PBS) | 1002 | Jan. 04, 2001 | 07:00 | a | a |
| | 1102 | 01/10-11/01 | 02:00 | 01:00 | a |
| | 1103 | Jan. 12, 2001 | 02:00 | 03:30 | a |
| 2 | 2002 | Jan. 18, 2001 | 02:30 | 01:30 | a |
| 0.04 mg/kg | 2003 | Feb. 08, 2001 | 01:00 | 02:30 | a |
| | 2101 | Jan. 16, 2001 | 03:00 | 01:30 | a |
| | 2102 | Feb. 06, 2001 | 01:00 | 04:30 | a |
| 3 | 3001 | Jan. 16, 2001 | 01:30 | 02:20 | a |
| 0.2 mg/kg | 3002 | Feb. 06, 2001 | 01:00 | 04:30 | a |
| | 3101 | Jan. 16, 2001 | 01:30 | 02:00 | a |
| | 3103 | Feb. 13, 2001 | 02:00 | 02:00 | a |
| 4 | 4002 | Feb. 07, 2001 | 01:00 | 02:30 | a |
| 1.0 mg/kg | 4003 | Feb. 13, 2001 | 02:30 | 06:00 | a |
| | 4101 | Jan. 18, 2001 | 02:20 | 02:30 | a |
| | 4102 | Feb. 08, 2001 | 02:00 | 01:30 | a |
| 5 | 5001 | Dec. 19, 2000 | 03:30 | 01:00 | a |
| 5.0 mg/kg | 5002 | 01/10-11/01 | 03:00 | b | a |
| | 5101 | Jan. 04, 2001 | 02:30 | a | 03:00 |
| | 5102 | Jan. 11, 2001 | 03:00 | b | a | a Data not collected.

b No bleeding.

TABLE 13

Hematology Parameters and Group Mean Study Results in the Angioplasty Study in Cynomolgus Monkeys

| | | Group Number/Dose (mg/kg) | | | | | | | | |
|---|---|---|---|---|---|---|---|---|---|---|
| | | 1<br>0 (PBS) | | 2<br>0.04 | | 3<br>0.2 | | 4<br>2.0 | | 5<br>5.0 | |
| Parameter | Time Points | M | F | M | F | M | F | M | F | M | F |
| Total Leukocyte | Pre-Treat. | 20.95 | 7.75 | 5.75 | 9.30 | 8.80 | 7.20 | 6.65 | 9.80 | 15.35 | 3.95 |
| Count (WBC) | 1.5 hours | 23.30 | 22.75 | 11.50 | 16.55 | 9.50 | 12.90 | 8.35 | 21.85 | 16.45 | 13.80 |
| ($10^3/\mu L$) | 24 hours | 21.65 | 26.80 | 16.40 | 23.55 | 19.25 | 16.30 | 21.35 | 19.90 | 30.95 | 16.90 |
| | Day 3 | 21.65 | 15.45 | 10.05 | 19.95 | 15.10 | 13.30 | 15.60 | 18.30 | 18.15 | 13.60 |
| | Day 7 | 25.55 | 20.75 | 10.95 | 19.10 | 17.60 | 14.35 | 16.15 | 21.30 | 12.10 | 14.10 |
| | Day 15 | 14.55 | 13.45 | 11.00 | 15.45 | 17.30 | 10.00 | 11.90 | 13.30 | 15.55 | 8.45 |
| Erythrocyte | Pre-Treat. | 7.225 | 5.910 | 5.445 | 5.320 | 6.325 | 5.000 | 5.025 | 5.205 | 6.990 | 4.890 |
| Count (RBC) | 1.5 hours | 5.910 | 5.310 | 4.950 | 4.715 | 5.335 | 4.110 | 4.920 | 4.865 | 5.270 | 4.700 |
| ($10^6/\mu L$) | 24 hours | 5.605 | 5.375 | 4.440 | 4.755 | 5.675 | 4.350 | 4.130 | 4.390 | 6.140 | 4.650 |
| | Day 3 | 5.330 | 5.285 | 5.005 | 4.680 | 5.855 | 4.250 | 3.930 | 4.660 | 5.820 | 4.200 |
| | Day 7 | 5.625 | 5.120 | 5.040 | 5.135 | 5.865 | 4.120 | 4.115 | 4.185 | 5.550 | 4.270 |
| | Day 15 | 5.865 | 5.355 | 5.530 | 5.505 | 5.370 | 4.755 | 4.730 | 4.955 | 6.020 | 5.035 |
| Hemoglobin | Pre-Treat. | 14.20 | 11.70 | 11.05 | 10.45 | 12.20 | 11.50 | 11.20 | 11.20 | 14.90 | 10.15 |
| Concentration | 1.5 hours | 12.00 | 10.40 | 10.05 | 9.20 | 10.25 | 9.50 | 10.95 | 10.50 | 11.15 | 9.45 |
| (HGB) (g/dL) | 24 hours | 10.90 | 10.65 | 9.40 | 9.15 | 10.95 | 10.15 | 9.15 | 9.45 | 13.05 | 9.25 |
| | Day 3 | 10.40 | 10.45 | 10.10 | 9.10 | 11.00 | 10.05 | 8.75 | 9.90 | 12.20 | 8.35 |
| | Day 7 | 10.85 | 10.25 | 10.45 | 10.10 | 11.10 | 9.80 | 9.35 | 9.30 | 11.90 | 8.55 |
| | Day 15 | 11.60 | 11.00 | 11.55 | 11.20 | 10.90 | 11.30 | 10.80 | 10.95 | 13.05 | 10.45 |
| Hematocrit | Pre-Treat. | 44.05 | 37.65 | 35.70 | 32.65 | 39.25 | 36.80 | 35.45 | 35.10 | 47.30 | 32.55 |
| Value (HCT)[a] | 1.5 hours | 37.70 | 33.80 | 32.05 | 29.05 | 33.20 | 30.30 | 34.35 | 32.85 | 35.60 | 30.90 |
| (%) | 24 hours | 35.05 | 34.15 | 30.60 | 29.40 | 35.45 | 32.05 | 28.75 | 29.95 | 41.75 | 30.65 |
| | Day 3 | 33.60 | 34.10 | 33.10 | 29.00 | 36.70 | 31.40 | 27.45 | 31.30 | 40.00 | 27.80 |
| | Day 7 | 36.05 | 33.60 | 33.65 | 32.30 | 36.80 | 30.95 | 29.95 | 28.75 | 39.50 | 29.40 |
| | Day 15 | 38.85 | 36.70 | 37.50 | 35.80 | 35.90 | 36.40 | 35.30 | 34.65 | 42.30 | 35.80 |
| Platelet Count | Pre-Treat. | 294.0 | 219.5 | 289.5 | 374.5 | 365.5 | 471.0 | 385.5 | 340.0 | 320.5 | 312.5 |
| (PLT) | 1.5 hours | 425.0 | 226.5 | 185.5 | 321.0 | 279.5 | 378.5 | 393.0 | 311.5 | 262.0 | 271.5 |
| ($10^3/\mu L$) | 24 hours | 276.0 | 306.0 | 233.0 | 388.0 | 378.0 | 430.0 | 308.5 | 316.0 | 323.5 | 314.5 |
| | Day 3 | 209.5 | 320.5 | 259.5 | 399.0 | 383.5 | 430.5 | 370.5 | 369.0 | 345.5 | 312.5 |
| | Day 7 | 525.5 | 513.5 | 484.0 | 550.0 | 668.5 | 605.5 | 487.5 | 617.0 | 477.0 | 414.0 |
| | Day 15 | 434.0 | 375.0 | 434.5 | 598.0 | 546.0 | 776.5 | 576.0 | 453.5 | 472.0 | 393.0 |

[a]Calculated value;
M = male;
F = female cH36-related patterns and were most likely due to repeated blood sampling and the stress of the surgical procedure. Group mean hematology values are summarized in Table 13.

Group mean coagulation values are summarized in Table 14. There were expected cH36-related prolongation of Prothrombin Times present for Group 4 (1.0 mg/kg) and Group 5 (5 mg/kg) animals. There were 2 to 6 fold increases in PT times for Group 4 animals at approximately 1 hour post-treatment (one Group 4 animal showed no notable increase). The values generally returned to baseline by Day 2. The PT times for Group 5 animals were increased 4 to 17 fold at 1-hour post treatment and 3 to 6 fold at Day 2. Two of the Group 5 animals still had a notable increase in PT time at Day 3 (animal 5002-5 fold). The Group 5 PT times otherwise generally returned to baseline by Day 3 or 7. There were no test article-related effects noted for activated partial thromboplastin time (APTT) or fibrinogen (FIB) levels.

There were no alterations in serum chemistry parameters that were considered test article related. There were elevations in alanine aminotransferase (ALT) and aspartate aminotransferase (AST) present for some animals from all groups, generally at Day 2 or 3. These changes may have been due to the surgical and sample collection procedures concentrated during the first few days of study. The values mainly returned to baseline by Day 7 or 15, and there were no corresponding histopathologic findings noted in Group 1 or 5 animals. Macroscopic and microscopic assessment of urine samples collected prior to treatment and prior to necropsy revealed no apparent test article-related effects.

A comprehensive necropsy was performed on all animals, including those that died early (the exception is one control animal, Group 1 female No. 1101, removed from the study due to unusual anatomy which would have made the angioplasty procedure more difficult to perform and also because the animal did not recover from the anesthesia). There were three animals that died or were euthanized on Day 1 (Group 2 male No. 2001, Group 3 female No. 3102 and Group 4 male No. 4001). Since the early death animals came from three different groups, and did not include any deaths in the high dose group, and there were no toxicologically relevant findings in any of the animals that survived until termination, the deaths were considered related to the surgical procedure and unrelated to test article. Comparison of microscopic evaluation of tissues from Group 5 (5 mg/kg) and Group 1 (vehicle control) animals revealed no findings that were considered test article related.

Numerous organs and tissues were collected at necropsy. Of these, seven organs were weighed. Organ weights were determined prior to fixation and paired organs were weighed together. No effects on organ weights were observed.

To summarize, there were no toxicologically relevant findings noted in the clinical observations, body weight measurements, cutaneous bleeding times, clinical pathology results, organ weight measurements and the pathologic evaluation. A single intravenous administration of Sunol-cH36 at doses of 0.04, 0.2, 1.0 and 5.0 mg/kg, in a model of thrombosis, was well tolerated by cynomolgus monkeys. All findings other than normal, including early deaths, were attributed to the surgical procedure for endothelial denudation by angioplasty.

TABLE 14

Group Mean Coagulation Parameters in the Angioplasty Study in Cynomolgus Monkeys

| Parameter | Time Points | 1/0 M | 1/0 F | 2/0.04 M | 2/0.04 F | 3/0.2 M | 3/0.2 F | 4/1.0 M | 4/1.0 F | 5/5.0 M | 5/5.0 F |
|---|---|---|---|---|---|---|---|---|---|---|---|
| PT (sec) | Pre-Treat | 8.85 | 9.75 | 10.10 | 10.00 | 10.25 | 9.85 | 10.40 | 10.25 | 9.70 | 9.85 |
| | 1.5 hours | 11.00 | 10.80 | 12.60 | 10.45 | 13.30 | 12.00 | 48.05 | 16.75 | 102.85 | 73.40 |
| | 24 hours | 8.20 | 8.55 | 8.50 | 7.90 | 8.95 | 8.80 | 13.20 | 9.55 | 37.80 | 35.85 |
| | Day 3 | 7.95 | 8.25 | 7.95 | 7.80 | 8.20 | 8.45 | 9.50 | 8.40 | 59.15 | 13.20 |
| | Day 7 | 7.80 | 8.25 | 8.85 | 8.30 | 8.30 | 8.35 | 8.70 | 9.20 | 10.05 | 8.40 |
| | Day 15 | 11.00 | 9.60 | 9.05 | 9.10 | 9.80 | 9.45 | 9.45 | 9.45 | 9.15 | 9.30 |
| APTT (sec) | Pre-Treat | 20.90 | 23.20 | 21.00 | 23.80 | 24.95 | 21.25 | 26.25 | 24.20 | 21.65 | 22.60 |
| | 1.5 hours | 23.50 | 25.55 | 26.25 | 23.80 | 26.90 | 22.25 | 29.10 | 23.80 | 22.95 | 23.40 |
| | 24 hours | 20.00 | 21.35 | 20.55 | 20.00 | 20.55 | 19.50 | 22.50 | 20.75 | 21.80 | 20.25 |
| | Day 3 | 20.40 | 20.65 | 19.15 | 19.75 | 20.00 | 18.00 | 21.85 | 19.80 | 19.50 | 19.00 |
| | Day 7 | 17.20 | 20.35 | 20.10 | 20.90 | 21.20 | 18.40 | 22.35 | 23.20 | 19.35 | 17.40 |
| | Day 15 | 25.80 | 22.70 | 18.80 | 20.85 | 22.00 | 20.30 | 23.70 | 21.05 | 20.90 | 20.90 |
| FIB (mg/dL) | Pre-Treat | 165.5 | 174.5 | 153.0 | 164.0 | 145.0 | 239.5 | 176.0 | 141.5 | 180.5 | 117.0 |
| | 1.5 hours | 144.0 | 131.0 | 90.5 | 135.5 | 87.0 | 168.5 | 163.5 | 126.0 | 175.0 | 93.5 |
| | 24 hours | 446.5 | 412.5 | 360.0 | 470.0 | 313.0 | 496.5 | 237.5 | 514.0 | 533.0 | 319.5 |
| | Day 3 | 638.5 | 663.0 | 624.5 | 433.0 | 578.0 | 500.5 | 383.0 | 421.5 | 623.5 | 418.5 |
| | Day 7 | 329.0 | 317.0 | 344.0 | 244.0 | 384.0 | 367.5 | 332.5 | 507.0 | 315.0 | 371.0 |
| | Day 15 | 185.5 | 181.5 | 219.5 | 235.0 | 97.0 | 254.0 | 313.5 | 201.5 | 244.5 | 200.0 |

M = male;
F = female

TABLE 15

Study Design for the Angioplasty Study in Cynomolgus Monkeys

| Group Number | Number of Animals Male | Number of Animals Female | Surgical Procedure on Day 1 | Test Article | Dose Level (mg/kg) | Dose Concentration (mg/mL) | Dose Volume (mL/kg) |
|---|---|---|---|---|---|---|---|
| 1 | 2 | 3* | Angioplasty | PBS | 0 | 0 | 0.5 |
| 2 | 3* | 2 | | Sunol-cH36 | 0.04 | 0.515 | 0.08 |
| 3 | 2 | 3* | | | 0.2 | | 0.4 |
| 4 | 3* | 2 | | | 1.0 | 10.3 | 0.1 |
| 5 | 2 | 2 | | | 5.0 | | 0.5 |

One animal from each of the indicated groups died on Day 1 after most of the Day 1 procedures were completed. One animal was added to each of these groups to provide a total of 2 males and 2 females per group.

For the pharmacodynamic component of this study, acute vascular thrombosis and platelet deposition at the sites of vascular injury were measured by gamma scintigraphy of radiolabeled platelets. Radiolabeled platelets were injected into each animal after treatment with the test article. Gamma camera images were acquired for 2 hours following the angioplasty procedure. Not all animals had all images acquired at the same time due to logistical and technical limitations, so the time of acquisition is only approximate. Region-of-interest analyses were performed at the site of injury and compared to that of background (i.e. soft tissue adjacent to the target injury site). A target injury site to background (T/B) ratio was calculated and the mean T/B ratio is presented in FIG. 13. The mean T/B ratio in Group 1 increased from 3 at 30 minutes to 3.55 at 2 hours suggesting that continued deposition of platelets is occurring at the injury site. Animals treated with Sunol-cH36 at the higher doses (0.2-5 mg/kg) have reduced T/B ratios indicating that Sunol-cH36 had an effect of inhibiting platelet deposition at the site of vessel injury.

TABLE 16

Gamma Scintigraphy Analysis of $^{111}$Indium-labeled Platelet Deposition

| Sunol-cH36/ Dose | Animal Number | Activity at 30 minutes Target | Activity at 30 minutes Background | Activity at 30 minutes T/B | Activity at 2 hours Target | Activity at 2 hours Background | Activity at 2 hours T/B |
|---|---|---|---|---|---|---|---|
| Group 1 | 1001 | 30 | 15 | 2.0 | 37 | 16 | 2.31 |
| 0 (PBS) | 1002 | 14 | 5 | 2.8 | 14 | 5 | 2.8 |
| | 1101* | 57 | 33 | 1.73 | 49 | 17 | 2.89 |
| | 1102 | 103 | 17 | 6.06 | 92 | 12 | 7.67 |

TABLE 16-continued

Gamma Scintigraphy Analysis of [111]Indium-labeled Platelet Deposition

| Sunol-cH36/ Dose | Animal Number | Activity at 30 minutes | | | Activity at 2 hours | | |
|---|---|---|---|---|---|---|---|
| | | arget | Background | T/B | arget | Background | T/B |
| | 1103 | 32 | 13 | 2.46 | 42 | 20 | 2.1 |
| | Mean ± S.D. | | 3.01 ± 1.75 | | | 3.55 ± 2.32 | |
| Group 2 | 2001* | 129 | 10 | 12.9 | 119 | 9 | 13.22 |
| 0.04 mg/kg | 2002 | 36 | 18 | 2.0 | 35 | 22 | 1.59 |
| | 2101 | 37 | 22 | 1.68 | 34 | 23 | 1.48 |
| | 2102 | 53 | 33 | 1.61 | 45 | 24 | 1.88 |
| | Mean ± S.D. | | 4.55 ± 5.57 | | | 4.54 ± 5.79 | |
| Group 3 | 3001 | 62 | 29 | 2.14 | 51 | 36 | 1.42 |
| 0.2 mg/kg | 3002 | 70 | 26 | 2.69 | 76 | 23 | 3.3 |
| | 3101 | 37 | 19 | 1.95 | 31 | 20 | 1.55 |
| | 3103 | 48 | 21 | 2.29 | 15 | 14 | 1.07 |
| | Mean ± S.D. | | 2.27 ± 0.31 | | | 1.84 ± 0.99 | |
| Group 4 | 4001* | 14 | 6 | 2.33 | 12 | 5 | 2.4 |
| 1.0 mg/kg | 4002 | 47 | 30 | 1.57 | 42 | 27 | 1.56 |
| | 4003 | 22 | 16 | 1.37 | 28 | 13 | 2.15 |
| | 4101 | 11 | 8 | 1.4 | 10 | 9 | 1.11 |
| | Mean ± S.D. | | 1.67 ± 0.45 | | | 1.81 ± 0.58 | |
| Group 5 | 5001 | 42 | 26 | 1.62 | 44 | 31 | 1.42 |
| 5.0 mg/kg | 5002 | 43 | 26 | 1.65 | 41 | 23 | 1.78 |
| | 5101 | 36 | 20 | 1.8 | 31 | 19 | 1.63 |
| | 5102 | 18 | 10 | 1.8 | 31 | 19 | 1.63 |
| | Mean ± S.D. | | 1.72 ± 0.1 | | | 1.62 ± 0.15 | |

*These animals were imaged but later died during the initial 24 hours of the study.

Example 7

Electrolytic Injury Model in Cynomolgus Monkeys

The electrolytic injury model used in this study is similar to that described for carotid artery thrombosis in cynomolgus monkeys (see Rote W E, Nedelman M A, Xu D-X, Manley P J, Weisman H, Cunnighharm M R, Lucchesi B R, *Stroke* 25:1223-1233 (1994)). In the electrolytic injury model, continuous anodal current is applied to the intimal surface of the carotid or femoral arteries. This treatment will lead to the denudation of the endothelium and a deep injury of the sub-endothelial layers. The resulting vessel wall injury and endothelial lesion provide stimuli (TF and collagen exposure) for coagulation and platelet activation, which then leads to the formation of a platelet-rich intravascular thrombus at the injury site. In this study, the efficacy of Sunol-cH$_{36}$ was tested in cynomolgus monkeys using the arterial thrombosis model induced by electrolytic injury. This thrombosis model mimics the clinical settings of unstable angina and non-ST-segment elevation myocardial infarction where atherosclerotic plaque rupture leads to exposure of thrombogenic surfaces resulting in coagulation and platelet activation.

Table 17 shows the result from a study with two animals. In two control procedures the vessels occluded earlier than in the procedures when cH36 was used. All procedures were conducted with heparin and aspirin present. This indicates that cH36 can retard or prevent occlusion in a thrombosis model where heparin and aspirin are not effective.

TABLE 17

Effect of Sunol-cH36 on Blocking Thrombotic Occlusion Induced by Arterial Injury

| | Time to Occlusion Animal No. | |
|---|---|---|
| | #1 | #2 |
| Placebo | 54 min | 25 min |
| Sunol-cH36, 5 mg/kg | >2 hr | 82 min* |

*Vessel re-perfused 8 min after occlusion for 9 min before reoccluding. Animals pre-treated with aspirin and bolus heparin followed by heparin infusion during procedure.

Although Examples 1-7 have been described with particular reference to the cH36 chimeric antibody, the work described could have been practiced with other suitable antibodies of the invention e.g, hFAT or Fab (where the Fab can be derived from cH36, HFAT or hOAT).

The invention has been described in detail with reference to preferred embodiments thereof. However, it will be appreciated that those skilled in the art, upon consideration of the disclosure, may make modification and improvements within the spirit and scope of the invention.

What is claimed is:

1. A method for treating thrombosis in a mammal, the method comprising administering to the mammal a therapeutically effective amount of an antibody, or fragment thereof, that binds specifically to human tissue factor (TF) to form a complex, wherein the antibody comprises: (a) a light chain comprising three hypervariable regions comprising the sequences of SEQ ID NOs: 170, 6, and 7, respectively, and four framework regions comprising the sequences of SEQ ID NOs: 74, 84, 94, and 104, respectively, and (b) a heavy chain comprising three hypervariable regions comprising the sequences of SEQ ID NOs: 163, 164, and 165, respectively, and four framework regions comprising the sequences of SEQ ID NOs: 115, 128, 141, and 154, respectively.

2. The method of claim 1, wherein after administration of the antibody or fragment, the mammal exhibits a blood clotting time of between from about 50 to about 350 seconds as determined by a standard prothrombin (PT) time assay.

3. The method of claim 1, wherein the amount of the administered antibody, or fragment is sufficient to inhibit platelet deposition time by at least about 50% as determined by a standard platelet deposition assay.

4. The method of claim 1, wherein the amount of the administered antibody, or fragment reduces platelet deposition as determined by vessel injury to blood ratio by at least about 50% as determined by a standard vessel injury to blood ratio assay.

5. The method of claim 1, wherein the amount of the administered antibody, or fragment increases vessel patency by at least about 100%.

6. The method of claim 1, wherein the mammal is a primate.

7. The method of claim 6, wherein the primate is a human patient.

8. The method of claim 1, wherein the antibody further comprises a light chain constant region having at least 95% amino acid sequence identity to SEQ ID NOS: 166 or 168.

9. The method of claim 8, wherein the antibody further comprises a light chain constant region comprising the sequence of SEQ ID NOS: 166 or 168.

10. The method of claim 1, wherein the antibody further comprises a heavy chain constant region having at least 95% amino acid sequence identity to SEQ ID NOS: 167 or 169.

11. The method of claim 1, wherein the humanized antibody further comprises a constant region with an IgG1 (hOAT) or IgG4 (hFAT) isotype.

12. The method of claim 1, wherein the human TF binding fragment is Fab, Fab', or F(ab)$_2$.

13. The method of claim 1, wherein the humanized antibody is a monoclonal antibody.

14. The method of claim 1, wherein the antibody further comprises a light chain constant region comprising a sequence of SEQ ID NOS: 167 or 169.

15. The method of claim 1, wherein the amount of the humanized antibody or fragment thereof, administered to the mammal is between about 0.01 to about 25 mg/kg.

16. The method of claim 1, wherein the thrombosis is associated with cardiovascular disease.

17. The method of claim 16, wherein the cardiovascular disease is at least one of coronary artery disease, acute coronary syndrome, and atherosclerosis.

18. The method of claim 1, wherein the thrombosis is associated with angioplasty or restenosis.

19. The method of claim 1 wherein the antibody further comprises a light chain constant region of SEQ ID NO: 166 and a heavy chain constant region of SEQ ID NO:167.

20. The method of claim 1 wherein the antibody further comprises a light chain constant region of SEQ ID NO: 168 and a heavy chain constant region of SEQ ID NO:169.

21. A method for treating thrombosis in a mammal comprising administering to the mammal a therapeutically effective amount of an antibody, or fragment thereof, that binds specifically to human tissue factor (TF) to form a complex, wherein the antibody comprises a variable light chain comprising: three hypervariable regions comprising the sequences of SEQ ID NOs: 170, 6, and 7, respectively, and four framework regions comprising the sequences of SEQ ID NOs: 74, 84, 94, and 104, respectively.

22. A method for treating thrombosis in a mammal comprising administering to the mammal a therapeutically effective amount of an antibody, or fragment thereof, that binds specifically to human tissue factor (TF) to form a complex, wherein the antibody comprises a variable heavy chain comprising: three hypervariable regions comprising the sequences of SEQ ID NOs: 163, 164, and 165, respectively, and four framework regions comprising the sequences of SEQ ID NOs: 115, 128, 141, and 154, respectively.

23. The method of claim 21 wherein the antibody further comprises a light chain constant region of SEQ ID NO: 166 or SEQ ID NO:168.

24. The method of claim 22 wherein the antibody further comprises a heavy chain constant region of SEQ ID NO: 167 or SEQ ID NO:169.

\* \* \* \* \*

SEQUENCE LISTING

<160> NUMBER OF SEQ ID NOS: 170

<210> SEQ ID NO 1
<211> LENGTH: 321
<212> TYPE: DNA
<213> ORGANISM: Murine sp.
<220> FEATURE:
<221> NAME/KEY: CDS
<222> LOCATION: (1)..(321)

```
<400> SEQUENCE: 1 gac att cag atg acc cag tct cct gcc tcc cag tct gca tct ctg gga      48
Asp Ile Gln Met Thr Gln Ser Pro Ala Ser Gln Ser Ala Ser Leu Gly
 1               5                  10                  15 gaa agt gtc acc atc aca tgc ctg gca agt cag acc att gat aca tgg      96
Glu Ser Val Thr Ile Thr Cys Leu Ala Ser Gln Thr Ile Asp Thr Trp
             20                  25                  30 tta gca tgg tat cag cag aaa cca ggg aaa tct cct cag ctc ctg att     144
Leu Ala Trp Tyr Gln Gln Lys Pro Gly Lys Ser Pro Gln Leu Leu Ile
         35                  40                  45 tat gct gcc acc aac ttg gca gat ggg gtc cca tca agg ttc agt ggc     192
Tyr Ala Ala Thr Asn Leu Ala Asp Gly Val Pro Ser Arg Phe Ser Gly
     50                  55                  60 agt gga tct ggc aca aaa ttt tct ttc aag atc agc agc cta cag gct     240
Ser Gly Ser Gly Thr Lys Phe Ser Phe Lys Ile Ser Ser Leu Gln Ala
 65                  70                  75                  80 gaa gat ttt gta aat tat tac tgt caa caa gtt tac agt tct cca ttc     288
Glu Asp Phe Val Asn Tyr Tyr Cys Gln Gln Val Tyr Ser Ser Pro Phe
                 85                  90                  95 acg ttc ggt gct ggg acc aag ctg gag ctg aaa                         321
Thr Phe Gly Ala Gly Thr Lys Leu Glu Leu Lys
                100                 105

<210> SEQ ID NO 2
<211> LENGTH: 107
<212> TYPE: PRT
<213> ORGANISM: Murine sp.

<400> SEQUENCE: 2

Asp Ile Gln Met Thr Gln Ser Pro Ala Ser Gln Ser Ala Ser Leu Gly
 1               5                  10                  15

Glu Ser Val Thr Ile Thr Cys Leu Ala Ser Gln Thr Ile Asp Thr Trp
             20                  25                  30

Leu Ala Trp Tyr Gln Gln Lys Pro Gly Lys Ser Pro Gln Leu Leu Ile
         35                  40                  45

Tyr Ala Ala Thr Asn Leu Ala Asp Gly Val Pro Ser Arg Phe Ser Gly
     50                  55                  60

Ser Gly Ser Gly Thr Lys Phe Ser Phe Lys Ile Ser Ser Leu Gln Ala
 65                  70                  75                  80

Glu Asp Phe Val Asn Tyr Tyr Cys Gln Gln Val Tyr Ser Ser Pro Phe
                 85                  90                  95

Thr Phe Gly Ala Gly Thr Lys Leu Glu Leu Lys
                100                 105

<210> SEQ ID NO 3
<211> LENGTH: 351
<212> TYPE: DNA
<213> ORGANISM: Murine sp.
<220> FEATURE:
<221> NAME/KEY: CDS
<222> LOCATION: (1)..(351)

<400> SEQUENCE: 3 gag atc cag ctg cag cag tct gga cct gag ctg gtg aag cct ggg gct      48
Glu Ile Gln Leu Gln Gln Ser Gly Pro Glu Leu Val Lys Pro Gly Ala
 1               5                  10                  15 tca gtg cag gta tcc tgc aag act tct ggt tac tca ttc act gac tac      96
Ser Val Gln Val Ser Cys Lys Thr Ser Gly Tyr Ser Phe Thr Asp Tyr
             20                  25                  30 aac gtg tac tgg gtg agg cag agc cat gga aag agc ctt gag tgg att     144
```

```
                Asn Val Tyr Trp Val Arg Gln Ser His Gly Lys Ser Leu Glu Trp Ile
                             35                  40                  45 gga tat att gat cct tac aat ggt att act atc tac gac cag aac ttc        192
Gly Tyr Ile Asp Pro Tyr Asn Gly Ile Thr Ile Tyr Asp Gln Asn Phe
             50                  55                  60 aag ggc aag gcc aca ttg act gtt gac aag tct tcc acc aca gcc ttc        240
Lys Gly Lys Ala Thr Leu Thr Val Asp Lys Ser Ser Thr Thr Ala Phe
 65                  70                  75                  80 atg cat ctc aac agc ctg aca tct gac gac tct gca gtt tat ttc tgt        288
Met His Leu Asn Ser Leu Thr Ser Asp Asp Ser Ala Val Tyr Phe Cys
                 85                  90                  95 gca aga gat gtg act acg gcc ctt gac ttc tgg ggc caa ggc acc act        336
Ala Arg Asp Val Thr Thr Ala Leu Asp Phe Trp Gly Gln Gly Thr Thr
            100                 105                 110 ctc aca gtc tcc tca                                                    351
Leu Thr Val Ser Ser
        115

<210> SEQ ID NO 4
<211> LENGTH: 117
<212> TYPE: PRT
<213> ORGANISM: Murine sp.

<400> SEQUENCE: 4

Glu Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr Asp Tyr
             20                  25                  30

Asn Val Tyr Trp Val Arg Gln Ser His Gly Lys Ser Leu Glu Trp Ile
         35                  40                  45

Gly Tyr Ile Asp Pro Tyr Asn Gly Ile Thr Ile Tyr Asp Gln Asn Phe
     50                  55                  60

Lys Gly Lys Ala Thr Leu Thr Val Asp Lys Ser Ser Thr Thr Ala Phe
 65                  70                  75                  80

Met His Leu Asn Ser Leu Thr Ser Asp Asp Ser Ala Val Tyr Phe Cys
                 85                  90                  95

Ala Arg Asp Val Thr Thr Ala Leu Asp Phe Trp Gly Gln Gly Thr Thr
            100                 105                 110

Leu Thr Val Ser Ser
        115

<210> SEQ ID NO 5
<211> LENGTH: 7
<212> TYPE: PRT
<213> ORGANISM: Murine sp.

<400> SEQUENCE: 5

Leu Ala Ser Gln Thr Ile Asp
 1               5

<210> SEQ ID NO 6
<211> LENGTH: 7
<212> TYPE: PRT
<213> ORGANISM: Murine sp.

<400> SEQUENCE: 6

Ala Ala Thr Asn Leu Ala Asp
 1               5

<210> SEQ ID NO 7
<211> LENGTH: 9
```

```
<212> TYPE: PRT
<213> ORGANISM: Murine sp.

<400> SEQUENCE: 7

Gln Gln Val Tyr Ser Ser Pro Phe Thr
 1               5

<210> SEQ ID NO 8
<211> LENGTH: 6
<212> TYPE: PRT
<213> ORGANISM: Murine sp.

<400> SEQUENCE: 8

Thr Asp Tyr Asn Val Tyr
 1               5

<210> SEQ ID NO 9
<211> LENGTH: 17
<212> TYPE: PRT
<213> ORGANISM: Murine sp.

<400> SEQUENCE: 9

Tyr Ile Asp Pro Tyr Asn Gly Ile Thr Ile Tyr Asp Gln Asn Phe Lys
 1               5                  10                  15

Gly

<210> SEQ ID NO 10
<211> LENGTH: 8
<212> TYPE: PRT
<213> ORGANISM: Murine sp.

<400> SEQUENCE: 10

Asp Val Thr Thr Ala Leu Asp Phe
 1               5

<210> SEQ ID NO 11
<211> LENGTH: 23
<212> TYPE: PRT
<213> ORGANISM: Murine sp.

<400> SEQUENCE: 11

Asp Ile Gln Met Thr Gln Ser Pro Ala Ser Gln Ser Ala Ser Leu Gly
 1               5                  10                  15

Glu Ser Val Thr Ile Thr Cys
            20

<210> SEQ ID NO 12
<211> LENGTH: 15
<212> TYPE: PRT
<213> ORGANISM: Murine sp.

<400> SEQUENCE: 12

Trp Tyr Gln Gln Lys Pro Gly Lys Ser Pro Gln Leu Leu Ile Tyr
 1               5                  10                  15

<210> SEQ ID NO 13
<211> LENGTH: 23
<212> TYPE: PRT
<213> ORGANISM: Homo sapiens

<400> SEQUENCE: 13

Asp Ile Gln Met Thr Gln Ser Pro Ala Ser Leu Ser Ala Ser Val Gly
 1               5                  10                  15

Asp Arg Val Thr Ile Thr Cys
```

```
<210> SEQ ID NO 14
<211> LENGTH: 15
<212> TYPE: PRT
<213> ORGANISM: Homo sapiens

<400> SEQUENCE: 14

Trp Tyr Leu Gln Lys Pro Gly Lys Ser Pro Gln Leu Leu Ile Tyr
1               5                   10                  15

<210> SEQ ID NO 15
<211> LENGTH: 32
<212> TYPE: PRT
<213> ORGANISM: Murine sp.

<400> SEQUENCE: 15

Gly Val Pro Ser Arg Phe Ser Gly Ser Gly Ser Gly Thr Lys Phe Ser
1               5                   10                  15

Phe Lys Ile Ser Ser Leu Gln Ala Glu Asp Phe Val Asn Tyr Tyr Cys
            20                  25                  30

<210> SEQ ID NO 16
<211> LENGTH: 10
<212> TYPE: PRT
<213> ORGANISM: Murine sp.

<400> SEQUENCE: 16

Phe Gly Ala Gly Thr Lys Leu Glu Leu Lys
1               5                   10

<210> SEQ ID NO 17
<211> LENGTH: 32
<212> TYPE: PRT
<213> ORGANISM: Homo sapiens

<400> SEQUENCE: 17

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Thr Tyr Tyr Cys
            20                  25                  30

<210> SEQ ID NO 18
<211> LENGTH: 10
<212> TYPE: PRT
<213> ORGANISM: Homo sapiens

<400> SEQUENCE: 18

Phe Gly Gln Gly Thr Lys Leu Glu Ile Lys
1               5                   10

<210> SEQ ID NO 19
<211> LENGTH: 30
<212> TYPE: PRT
<213> ORGANISM: Murine sp.

<400> SEQUENCE: 19

Glu Ile Gln Leu Gln Gln Ser Gly Pro Glu Leu Val Lys Pro Gly Ala
1               5                   10                  15

Ser Val Gln Val Ser Cys Lys Thr Ser Gly Tyr Ser Phe Thr
            20                  25                  30

<210> SEQ ID NO 20
<211> LENGTH: 14
```

```
<212> TYPE: PRT
<213> ORGANISM: Murine sp.

<400> SEQUENCE: 20

Trp Val Arg Gln Ser His Gly Lys Ser Leu Glu Trp Ile Gly
 1               5                  10

<210> SEQ ID NO 21
<211> LENGTH: 30
<212> TYPE: PRT
<213> ORGANISM: Homo sapiens

<400> SEQUENCE: 21

Gln Ile Gln Leu Val Gln Ser Gly Gly Glu Val Lys Lys Pro Gly Ala
 1               5                  10                  15

Ser Val Arg Val Ser Cys Lys Ala Ser Gly Tyr Ser Phe Thr
            20                  25                  30

<210> SEQ ID NO 22
<211> LENGTH: 14
<212> TYPE: PRT
<213> ORGANISM: Homo sapiens

<400> SEQUENCE: 22

Trp Val Arg Gln Ser Pro Gly Lys Gly Leu Glu Trp Ile Gly
 1               5                  10

<210> SEQ ID NO 23
<211> LENGTH: 32
<212> TYPE: PRT
<213> ORGANISM: Murine sp.

<400> SEQUENCE: 23

Lys Ala Thr Leu Thr Val Asp Lys Ser Ser Thr Thr Ala Phe Met His
 1               5                  10                  15

Leu Asn Ser Leu Thr Ser Asp Asp Ser Ala Val Tyr Phe Cys Ala Arg
            20                  25                  30

<210> SEQ ID NO 24
<211> LENGTH: 11
<212> TYPE: PRT
<213> ORGANISM: Murine sp.

<400> SEQUENCE: 24

Trp Gly Gln Gly Thr Thr Leu Thr Val Ser Ser
 1               5                  10

<210> SEQ ID NO 25
<211> LENGTH: 32
<212> TYPE: PRT
<213> ORGANISM: Homo sapiens

<400> SEQUENCE: 25

Lys Ala Thr Leu Thr Val Asp Lys Ser Thr Ser Thr Ala Tyr Met Glu
 1               5                  10                  15

Leu Ser Ser Leu Arg Ser Glu Asp Thr Ala Val Tyr Phe Cys Ala Arg
            20                  25                  30

<210> SEQ ID NO 26
<211> LENGTH: 11
<212> TYPE: PRT
<213> ORGANISM: Homo sapiens

<400> SEQUENCE: 26
```

Trp Gly Gln Gly Thr Thr Val Thr Val Ser Ser
 1               5                   10

```
<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 27
tttcgtacgt cttgtcccag atccagctgc agcagtc                    37

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 28
agcgaattct gaggagactg tgacagtggt gccttggccc cag             43

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 29
gtgaggcaga gccctggaaa gggccttgag tggattgg                   38

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 30
ccaatccact caaggccctt tccagggctc tgcctcac                   38

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 31
gcatctcaac agcctgagat ctgaagacac tgcagtttat ttctgtg         47

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 32
ctgcagtgtc ttcagatctc aggctgttga gatgcatgaa ggc             43

<210> SEQ ID NO 33
<211> LENGTH: 43
<212> TYPE: DNA
<213> ORGANISM: Artificial Sequence
```

```
<220> FEATURE:
<223> OTHER INFORMATION: Description of Artificial Sequence: Primer

<400> SEQUENCE: 33
gtcttcagat ctcaggctgc tgagctccat gaaggctgtg gtg                43

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 34
tacgactcac tatagggcga attgg                                    25

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 35
ctgttgacaa gtctaccagc acagcctaca tggagctcag cag                43

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 36
ctgctgagct ccatgtaggc tgtgctggta gacttgtcaa cag                43

<210> SEQ ID NO 37
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 37
gcactgaagc cccaggcttc accagctcac ctccagactg ctgcagc            47

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 38
ctggggcttc agtgcgggta tcctgcaagg cttctggtta ctcattcac          49

<210> SEQ ID NO 39
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 39
tcgtacgtct tgtcccagat ccagctggtg cagtctggag gtgagc             46
```

```
<210> SEQ ID NO 40
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 40
gcactgaagc cccaggcttc ttcacctcac ctccagactg cacc                    44

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 41
gcagtctgga cctgagctga agaagcctgg gg                                 32

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 42
ccccaggctt ttcagctca ggtccagact gc                                  32

<210> SEQ ID NO 43
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 43
gctggtgcag tctggacctg aggtgaagaa gcc                                33

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 44
ggcttcttca cctcaggtcc agactgcacc agc                                33

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 45
gcagtctgga cctgagctgg tgaagcctgg ggcttc                             36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 46
```

-continued gaagcccag gcttcaccag ctcaggtcca gactgc          36

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 47
cagtctggac ctgaggtggt gaagcctggg          30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 48
cccaggcttc accacctcag gtccagactg          30

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 49
ttcgaaaagt gtacttacgt ttgatctcca gcttggtccc ag          42

<210> SEQ ID NO 50
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 50
accggtgata tccagatgac ccagtctcc          29

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 51
ggttagcatg gtatctgcag aaaccaggg          29

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 52
ccctggtttc tgcagatacc atgctaacc          29

<210> SEQ ID NO 53
<211> LENGTH: 25
<212> TYPE: DNA
<213> ORGANISM: Artificial Sequence

```
<220> FEATURE:
<223> OTHER INFORMATION: Description of Artificial Sequence: Primer

<400> SEQUENCE: 53
tacgactcac tatagggcga attgg                                            25

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 54
ccacagatgc agacagggag gcaggagact g                                     31

<210> SEQ ID NO 55
<211> LENGTH: 51
<212> TYPE: DNA
<213> ORGANISM: Artificial Sequence
<220> FEATURE:
<223> OTHER INFORMATION: Description of Artificial Sequence: Primer

<400> SEQUENCE: 55
ttcgaaaagt gtacttacgt ttgatctcca gcttggtacc agcaccgaac g               51

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 56
cctgtctgca tctgtgggag atagggtcac catcacatgc                            40

<210> SEQ ID NO 57
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 57
gatctccagc ttggtaccct gaccgaacgt gaatgg                                36

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 58
gtaggctgct gatcgtgaaa gaaaagtctg tgccagatcc                            40

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Primer

<400> SEQUENCE: 59
cacgatcagc agcctacagc ctgaagattt tgtaaattat tactgtc                    47
```

```
<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 60
gcagcctaca gcctgaagat tttgcaactt attactgtca acaag            45

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 61
cttgttgaca gtaataagtt gcaaaatctt caggctgtag gctgc            45

<210> SEQ ID NO 62
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 62
cagcagccta cagcctgaag attttgcaaa ttattactgt caac              44

<210> SEQ ID NO 63
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 63
gttgacagta ataatttgca aaatcttcag gctgtaggct gctg              44

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 64
cagtggatct ggcacaaagt tttctttcac gatcagcagc                   40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 65
gctgctgatc gtgaaagaaa actttgtgcc agatccactg                   40

<210> SEQ ID NO 66
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 66
```

```
ctgcagaaac cagggcaatc tcctcagctc ctg                                    33

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 67
caggagctga ggagattgcc ctggtttctg cag                                    33

<210> SEQ ID NO 68
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-03 FR1 amino acid sequence

<400> SEQUENCE: 68

Asp Ile Gln Met Thr Gln Ser Pro Ala Ser Gln Ser Ala Ser Leu Gly
 1               5                  10                  15

Glu Ser Val Thr Ile Thr Cys
            20

<210> SEQ ID NO 69
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-04 FR1 amino acid sequence

<400> SEQUENCE: 69

Asp Ile Gln Met Thr Gln Ser Pro Ala Ser Gln Ser Ala Ser Leu Gly
 1               5                  10                  15

Glu Ser Val Thr Ile Thr Cys
            20

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-05 FR1 amino acid sequence

<400> SEQUENCE: 70

Asp Ile Gln Met Thr Gln Ser Pro Ala Ser Leu Ser Ala Ser Val Gly
 1               5                  10                  15

Asp Arg Val Thr Ile Thr Cys
            20

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-06 FR1 amino acid sequence

<400> SEQUENCE: 71

Asp Ile Gln Met Thr Gln Ser Pro Ala Ser Gln Ser Ala Ser Leu Gly
 1               5                  10                  15
```

```
Glu Ser Val Thr Ile Thr Cys
            20

<210> SEQ ID NO 72
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-07 FR1 amino acid sequence

<400> SEQUENCE: 72

Asp Ile Gln Met Thr Gln Ser Pro Ala Ser Gln Ser Ala Ser Leu Gly
 1               5                  10                  15

Glu Ser Val Thr Ile Thr Cys
            20

<210> SEQ ID NO 73
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-08 FR1 amino acid sequence

<400> SEQUENCE: 73

Asp Ile Gln Met Thr Gln Ser Pro Ala Ser Gln Ser Ala Ser Leu Gly
 1               5                  10                  15

Glu Ser Val Thr Ile Thr Cys
            20

<210> SEQ ID NO 74
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-09 FR1 amino acid sequence

<400> SEQUENCE: 74

Asp Ile Gln Met Thr Gln Ser Pro Ala Ser Leu Ser Ala Ser Val Gly
 1               5                  10                  15

Asp Arg Val Thr Ile Thr Cys
            20

<210> SEQ ID NO 75
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-10 FR1 amino acid sequence

<400> SEQUENCE: 75

Asp Ile Gln Met Thr Gln Ser Pro Ala Ser Leu Ser Ala Ser Val Gly
 1               5                  10                  15

Asp Arg Val Thr Ile Thr Cys
            20

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-11 FR1 amino acid sequence
```

```
<400> SEQUENCE: 76

Asp Ile Gln Met Thr Gln Ser Pro Ala Ser Leu Ser Ala Ser Val Gly
 1               5                  10                  15

Asp Arg Val Thr Ile Thr Cys
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      humanized LC-12 FR1 amino acid sequence

<400> SEQUENCE: 77

Asp Ile Gln Met Thr Gln Ser Pro Ala Ser Leu Ser Ala Ser Val Gly
 1               5                  10                  15

Asp Arg Val Thr Ile Thr Cys
            20

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      humanized LC-03 FR2 amino acid sequence

<400> SEQUENCE: 78

Trp Tyr Gln Gln Lys Pro Gly Lys Ser Pro Gln Leu Leu Ile Tyr
 1               5                  10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      humanized LC-04 FR2 amino acid sequence

<400> SEQUENCE: 79

Trp Tyr Leu Gln Lys Pro Gly Lys Ser Pro Gln Leu Leu Ile Tyr
 1               5                  10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      humanized LC-05 FR2 amino acid sequence

<400> SEQUENCE: 80

Trp Tyr Leu Gln Lys Pro Gly Lys Ser Pro Gln Leu Leu Ile Tyr
 1               5                  10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      humanized LC-06 FR2 amino acid sequence

<400> SEQUENCE: 81

Trp Tyr Leu Gln Lys Pro Gly Lys Ser Pro Gln Leu Leu Ile Tyr
 1               5                  10                  15
```

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-07 FR2 amino acid sequence

<400> SEQUENCE: 82

Trp Tyr Leu Gln Lys Pro Gly Lys Ser Pro Gln Leu Leu Ile Tyr
 1               5                  10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-08 FR2 amino acid sequence

<400> SEQUENCE: 83

Trp Tyr Leu Gln Lys Pro Gly Lys Ser Pro Gln Leu Leu Ile Tyr
 1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-09 FR2 amino acid sequence

<400> SEQUENCE: 84

Trp Tyr Leu Gln Lys Pro Gly Lys Ser Pro Gln Leu Leu Ile Tyr
 1               5                  10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-10 FR2 amino acid sequence

<400> SEQUENCE: 85

Trp Tyr Leu Gln Lys Pro Gly Lys Ser Pro Gln Leu Leu Ile Tyr
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-11 FR2 amino acid sequence

<400> SEQUENCE: 86

Trp Tyr Leu Gln Lys Pro Gly Lys Ser Pro Gln Leu Leu Ile Tyr
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
humanized LC-12 FR2 amino acid sequence

```
<400> SEQUENCE: 87

Trp Tyr Leu Gln Lys Pro Gly Gln Ser Pro Gln Leu Leu Ile Tyr
 1               5                  10                  15

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-03 FR3 amino acid sequence

<400> SEQUENCE: 88

Gly Val Pro Ser Arg Phe Ser Gly Ser Gly Ser Gly Thr Lys Phe Ser
 1               5                  10                  15

Phe Lys Ile Ser Ser Leu Gln Ala Glu Asp Phe Val Asn Tyr Tyr Cys
                20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-04 FR3 amino acid sequence

<400> SEQUENCE: 89

Gly Val Pro Ser Arg Phe Ser Gly Ser Gly Ser Gly Thr Lys Phe Ser
 1               5                  10                  15

Phe Lys Ile Ser Ser Leu Gln Ala Glu Asp Phe Val Asn Tyr Tyr Cys
                20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-05 FR3 amino acid sequence

<400> SEQUENCE: 90

Gly Val Pro Ser Arg Phe Ser Gly Ser Gly Ser Gly Thr Lys Phe Ser
 1               5                  10                  15

Phe Lys Ile Ser Ser Leu Gln Ala Glu Asp Phe Val Asn Tyr Tyr Cys
                20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-06 FR3 amino acid sequence

<400> SEQUENCE: 91

Gly Val Pro Ser Arg Phe Ser Gly Ser Gly Ser Gly Thr Lys Phe Ser
 1               5                  10                  15

Phe Lys Ile Ser Ser Leu Gln Ala Glu Asp Phe Val Asn Tyr Tyr Cys
                20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic
``` humanized LC-07 FR3 amino acid sequence

<400> SEQUENCE: 92

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Val Asn Tyr Tyr Cys
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-08 FR3 amino acid sequence

<400> SEQUENCE: 93

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Thr Tyr Tyr Cys
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-09 FR3 amino acid sequence

<400> SEQUENCE: 94

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Thr Tyr Tyr Cys
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-10 FR3 amino acid sequence

<400> SEQUENCE: 95

Gly Val Pro Ser Arg Phe Ser Gly Ser Gly Ser Gly Thr Asp Phe Ser
1               5                   10                  15

Phe Thr Ile Ser Ser Leu Gln Pro Glu Asp Phe Ala Asn Tyr Tyr Cys
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-11 FR3 amino acid sequence

<400> SEQUENCE: 96

Gly Val Pro Ser Arg Phe Ser Gly Ser Gly Ser Gly Thr Lys Phe Ser
1               5                   10                  15

Phe Thr Ile Ser Ser Leu Gln Pro Glu Asp Phe Ala Asn Tyr Tyr Cys
            20                  25                  30

<210> SEQ ID NO 97

```
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized LC-12 FR3 amino acid sequence

<400> SEQUENCE: 97

Gly Val Pro Ser Arg Phe Ser Gly Ser Gly Ser Gly Thr Lys Phe Ser
1               5                   10                  15

Phe Thr Ile Ser Ser Leu Gln Pro Glu Asp Phe Ala Asn Tyr Tyr Cys
            20                  25                  30

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-03 FR4 amino acid sequence

<400> SEQUENCE: 98

Phe Gly Ala Gly Thr Lys Leu Glu Ile Lys
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-04 FR4 amino acid sequence

<400> SEQUENCE: 99

Phe Gly Ala Gly Thr Lys Leu Glu Ile Lys
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-05 FR4 amino acid sequence

<400> SEQUENCE: 100

Phe Gly Gln Gly Thr Lys Leu Glu Ile Lys
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-06 FR4 amino acid sequence

<400> SEQUENCE: 101

Phe Gly Gln Gly Thr Lys Leu Glu Ile Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-07 FR4 amino acid sequence
```

-continued

```
<400> SEQUENCE: 102

Phe Gly Gln Gly Thr Lys Leu Glu Ile Lys
 1               5                  10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-08 FR4 amino acid sequence

<400> SEQUENCE: 103

Phe Gly Gln Gly Thr Lys Leu Glu Ile Lys
 1               5                  10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-09 FR4 amino acid sequence

<400> SEQUENCE: 104

Phe Gly Gln Gly Thr Lys Leu Glu Ile Lys
 1               5                  10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-10 FR4 amino acid sequence

<400> SEQUENCE: 105

Phe Gly Gln Gly Thr Lys Leu Glu Ile Lys
 1               5                  10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-11 FR4 amino acid sequence

<400> SEQUENCE: 106

Phe Gly Gln Gly Thr Lys Leu Glu Ile Lys
 1               5                  10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      humanized LC-12 FR4 amino acid sequence

<400> SEQUENCE: 107

Phe Gly Gln Gly Thr Lys Leu Glu Ile Lys
 1               5                  10

<210> SEQ ID NO 108
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      humanized HC-01 FR1 amino acid sequence

<400> SEQUENCE: 108

Gln Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr
             20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-02 FR1 amino acid sequence

<400> SEQUENCE: 109

Gln Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr
             20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-03 FR1 amino acid sequence

<400> SEQUENCE: 110

Gln Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr
             20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-04 FR1 amino acid sequence

<400> SEQUENCE: 111

Gln Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr
             20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-05 FR1 amino acid sequence

<400> SEQUENCE: 112

Gln Ile Gln Leu Gln Gln Ser Gly Pro Glu Leu Val Lys Pro Gly Ala
 1               5                  10                  15

Ser Val Gln Val Ser Cys Lys Thr Ser Gly Tyr Ser Phe Thr
             20                  25                  30
```

```
<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-06 FR1 amino acid sequence

<400> SEQUENCE: 113

Gln Met Gln Leu Gln Gln Ser Gly Gly Glu Leu Val Lys Pro Gly Ala
 1               5                  10                  15

Ser Val Arg Val Ser Cys Lys Ala Ser Gly Tyr Ser Phe Thr
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-07 FR1 amino acid sequence

<400> SEQUENCE: 114

Gln Ile Gln Leu Val Gln Ser Gly Gly Glu Leu Val Lys Pro Gly Ala
 1               5                  10                  15

Ser Val Arg Val Ser Cys Lys Ala Ser Gly Tyr Ser Phe Thr
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-08 FR1 amino acid sequence

<400> SEQUENCE: 115

Gln Ile Gln Leu Val Gln Ser Gly Gly Glu Val Lys Lys Pro Gly Ala
 1               5                  10                  15

Ser Val Arg Val Ser Cys Lys Ala Ser Gly Tyr Ser Phe Thr
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-08R1 FR1 amino acid sequence

<400> SEQUENCE: 116

Gln Ile Gln Leu Val Gln Ser Gly Gly Glu Val Lys Lys Pro Gly Ala
 1               5                  10                  15

Ser Val Arg Val Ser Cys Lys Ala Ser Gly Tyr Ser Phe Thr
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-11 FR1 amino acid sequence

<400> SEQUENCE: 117

Gln Ile Gln Leu Val Gln Ser Gly Pro Glu Val Lys Lys Pro Gly Ala
```

```
                1               5                  10                 15
Ser Val Arg Val Ser Cys Lys Ala Ser Gly Tyr Ser Phe Thr
                20                 25                 30

<210> SEQ ID NO 118
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-12 FR1 amino acid sequence

<400> SEQUENCE: 118

Gln Ile Gln Leu Val Gln Ser Gly Pro Glu Leu Lys Lys Pro Gly Ala
1               5                   10                  15
Ser Val Arg Val Ser Cys Lys Ala Ser Gly Tyr Ser Phe Thr
                20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-09 FR1 amino acid sequence

<400> SEQUENCE: 119

Gln Ile Gln Leu Val Gln Ser Gly Pro Glu Leu Val Lys Pro Gly Ala
1               5                   10                  15
Ser Val Arg Val Ser Cys Lys Ala Ser Gly Tyr Ser Phe Thr
                20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      humanized HC-10 FR1 amino acid sequence

<400> SEQUENCE: 120

Gln Ile Gln Leu Val Gln Ser Gly Pro Glu Val Val Lys Pro Gly Ala
1               5                   10                  15
Ser Val Arg Val Ser Cys Lys Ala Ser Gly Tyr Ser Phe Thr
                20                  25                  30

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-01 FR2 amino acid sequence

<400> SEQUENCE: 121

Trp Val Arg Gln Ser His Gly Lys Ser Leu Glu Trp Ile Gly
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-02 FR2 amino acid sequence

<400> SEQUENCE: 122
```

Trp Val Arg Gln Ser Pro Gly Lys Gly Leu Glu Trp Ile Gly
 1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-03 FR2 amino acid sequence

<400> SEQUENCE: 123

Trp Val Arg Gln Ser Pro Gly Lys Gly Leu Glu Trp Ile Gly
 1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-04 FR2 amino acid sequence

<400> SEQUENCE: 124

Trp Val Arg Gln Ser Pro Gly Lys Gly Leu Glu Trp Ile Gly
 1               5                   10

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-05 FR2 amino acid sequence

<400> SEQUENCE: 125

Trp Val Arg Gln Ser Pro Gly Lys Gly Leu Glu Trp Ile Gly
 1               5                   10

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-06 FR2 amino acid sequence

<400> SEQUENCE: 126

Trp Val Arg Gln Ser Pro Gly Lys Gly Leu Glu Trp Ile Gly
 1               5                   10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-07 FR2 amino acid sequence

<400> SEQUENCE: 127

Trp Val Arg Gln Ser Pro Gly Lys Gly Leu Glu Trp Ile Gly
 1               5                   10

<210> SEQ ID NO 128
<211> LENGTH: 14
<212> TYPE: PRT
<213> ORGANISM: Artificial Sequence
<220> FEATURE:

<223> OTHER INFORMATION: Description of Artificial Sequence: Synthetic
      humanized HC-08 FR2 amino acid sequence

<400> SEQUENCE: 128

Trp Val Arg Gln Ser Pro Gly Lys Gly Leu Glu Trp Ile Gly
 1               5                  10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-08R1 FR2 amino acid sequence

<400> SEQUENCE: 129

Trp Val Arg Gln Ser Pro Gly Lys Gly Leu Glu Trp Ile Gly
 1               5                  10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-11 FR2 amino acid sequence

<400> SEQUENCE: 130

Trp Val Arg Gln Ser Pro Gly Lys Gly Leu Glu Trp Ile Gly
 1               5                  10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-12 FR2 amino acid sequence

<400> SEQUENCE: 131

Trp Val Arg Gln Ser Pro Gly Lys Gly Leu Glu Trp Ile Gly
 1               5                  10

<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-09 FR2 amino acid sequence

<400> SEQUENCE: 132

Trp Val Arg Gln Ser Pro Gly Lys Gly Leu Glu Trp Ile Gly
 1               5                  10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      humanized HC-10 FR2 amino acid sequence

<400> SEQUENCE: 133

Trp Val Arg Gln Ser Pro Gly Lys Gly Leu Glu Trp Ile Gly
 1               5                  10

<210> SEQ ID NO 134

```
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-01 FR3 amino acid sequence

<400> SEQUENCE: 134

Lys Ala Thr Leu Thr Val Asp Lys Ser Ser Thr Thr Ala Phe Met His
 1               5                  10                  15

Leu Asn Ser Leu Thr Ser Asp Asp Ser Ala Val Tyr Phe Cys Ala Arg
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-02 FR3 amino acid sequence

<400> SEQUENCE: 135

Lys Ala Thr Leu Thr Val Asp Lys Ser Ser Thr Thr Ala Phe Met His
 1               5                  10                  15

Leu Asn Ser Leu Thr Ser Asp Asp Ser Ala Val Tyr Phe Cys Ala Arg
            20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-03 FR3 amino acid sequence

<400> SEQUENCE: 136

Lys Ala Thr Leu Thr Val Asp Lys Ser Ser Thr Thr Ala Phe Met His
 1               5                  10                  15

Leu Asn Ser Leu Arg Ser Glu Asp Thr Ala Val Tyr Phe Cys Ala Arg
            20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-04 FR3 amino acid sequence

<400> SEQUENCE: 137

Lys Ala Thr Leu Thr Val Asp Lys Ser Ser Thr Thr Ala Phe Met Glu
 1               5                  10                  15

Leu Ser Ser Leu Arg Ser Glu Asp Thr Ala Val Tyr Phe Cys Ala Arg
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-05 FR3 amino acid sequence

<400> SEQUENCE: 138

Lys Ala Thr Leu Thr Val Asp Lys Ser Thr Ser Thr Ala Tyr Met Glu
 1               5                  10                  15
```

```
Leu Ser Ser Leu Arg Ser Glu Asp Thr Ala Val Tyr Phe Cys Ala Arg
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-06 FR3 amino acid sequence

<400> SEQUENCE: 139

Lys Ala Thr Leu Thr Val Asp Lys Ser Thr Ser Thr Ala Tyr Met Glu
  1               5                  10                  15

Leu Ser Ser Leu Arg Ser Glu Asp Thr Ala Val Tyr Phe Cys Ala Arg
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-07 FR3 amino acid sequence

<400> SEQUENCE: 140

Lys Ala Thr Leu Thr Val Asp Lys Ser Thr Ser Thr Ala Tyr Met Glu
  1               5                  10                  15

Leu Ser Ser Leu Arg Ser Glu Asp Thr Ala Val Tyr Phe Cys Ala Arg
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-08 FR3 amino acid sequence

<400> SEQUENCE: 141

Lys Ala Thr Leu Thr Val Asp Lys Ser Thr Ser Thr Ala Tyr Met Glu
  1               5                  10                  15

Leu Ser Ser Leu Arg Ser Glu Asp Thr Ala Val Tyr Phe Cys Ala Arg
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-08R1 FR3 amino acid sequence

<400> SEQUENCE: 142

Lys Ala Thr Leu Thr Val Asp Lys Ser Thr Ser Thr Ala Tyr Met Glu
  1               5                  10                  15

Leu Ser Ser Leu Arg Ser Glu Asp Thr Ala Val Tyr Phe Cys Ala Arg
            20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-11 FR3 amino acid sequence
```

```
<400> SEQUENCE: 143

Lys Ala Thr Leu Thr Val Asp Lys Ser Thr Ser Thr Ala Tyr Met Glu
 1               5                   10                  15

Leu Ser Ser Leu Arg Ser Glu Asp Thr Ala Val Tyr Phe Cys Ala Arg
            20                  25                  30

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-12 FR3 amino acid sequence

<400> SEQUENCE: 144

Lys Ala Thr Leu Thr Val Asp Lys Ser Thr Ser Thr Ala Tyr Met Glu
 1               5                   10                  15

Leu Ser Ser Leu Arg Ser Glu Asp Thr Ala Val Tyr Phe Cys Ala Arg
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-09 FR3 amino acid sequence

<400> SEQUENCE: 145

Lys Ala Thr Leu Thr Val Asp Lys Ser Thr Ser Thr Ala Tyr Met Glu
 1               5                   10                  15

Leu Ser Ser Leu Arg Ser Glu Asp Thr Ala Val Tyr Phe Cys Ala Arg
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      humanized HC-10 FR3 amino acid sequence

<400> SEQUENCE: 146

Lys Ala Thr Leu Thr Val Asp Lys Ser Thr Ser Thr Ala Tyr Met Glu
 1               5                   10                  15

Leu Ser Ser Leu Arg Ser Glu Asp Thr Ala Val Tyr Phe Cys Ala Arg
            20                  25                  30

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-01 FR4 amino acid sequence

<400> SEQUENCE: 147

Trp Gly Gln Gly Thr Thr Val Thr Val Ser Ser
 1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
``` humanized HC-02 FR4 amino acid sequence

<400> SEQUENCE: 148

Trp Gly Gln Gly Thr Thr Val Thr Val Ser Ser
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-03 FR4 amino acid sequence

<400> SEQUENCE: 149

Trp Gly Gln Gly Thr Thr Val Thr Val Ser Ser
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-04 FR4 amino acid sequence

<400> SEQUENCE: 150

Trp Gly Gln Gly Thr Thr Val Thr Val Ser Ser
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-05 FR4 amino acid sequence

<400> SEQUENCE: 151

Trp Gly Gln Gly Thr Thr Val Thr Val Ser Ser
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-06 FR4 amino acid sequence

<400> SEQUENCE: 152

Trp Gly Gln Gly Thr Thr Val Thr Val Ser Ser
1               5                   10

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-07 FR4 amino acid sequence

<400> SEQUENCE: 153

Trp Gly Gln Gly Thr Thr Val Thr Val Ser Ser
1               5                   10

<210> SEQ ID NO 154
<211> LENGTH: 11

```
<212> TYPE: PRT
<213> ORGANISM: Artificial Sequence
<220> FEATURE:
<223> OTHER INFORMATION: Description of Artificial Sequence: Synthetic
      humanized HC-08 FR4 amino acid sequence

<400> SEQUENCE: 154

Trp Gly Gln Gly Thr Thr Val Thr Val Ser Ser
 1               5                  10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-08R1 FR4 amino acid sequence

<400> SEQUENCE: 155

Trp Gly Gln Gly Thr Thr Val Thr Val Ser Ser
 1               5                  10

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-11 FR4 amino acid sequence

<400> SEQUENCE: 156

Trp Gly Gln Gly Thr Thr Val Thr Val Ser Ser
 1               5                  10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-12 FR4 amino acid sequence

<400> SEQUENCE: 157

Trp Gly Gln Gly Thr Thr Val Thr Val Ser Ser
 1               5                  10

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-09 FR4 amino acid sequence

<400> SEQUENCE: 158

Trp Gly Gln Gly Thr Thr Val Thr Val Ser Ser
 1               5                  10

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      humanized HC-10 FR4 amino acid sequence

<400> SEQUENCE: 159

Trp Gly Gln Gly Thr Thr Val Thr Val Ser Ser
 1               5                  10
```

```
<210> SEQ ID NO 160
<211> LENGTH: 5
<212> TYPE: PRT
<213> ORGANISM: Murine sp.

<400> SEQUENCE: 160

Asp Tyr Asn Val Tyr
 1               5

<210> SEQ ID NO 161
<211> LENGTH: 17
<212> TYPE: PRT
<213> ORGANISM: Murine sp.

<400> SEQUENCE: 161

Tyr Ile Asp Pro Tyr Asn Gly Ile Thr Ile Tyr Asp Gln Asn Phe Lys
 1               5                  10                  15

Gly

<210> SEQ ID NO 162
<211> LENGTH: 8
<212> TYPE: PRT
<213> ORGANISM: Murine sp.

<400> SEQUENCE: 162

Asp Val Thr Thr Ala Leu Asp Phe
 1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      humanized HC-08 CDR1 amino acid sequence

<400> SEQUENCE: 163

Asp Tyr Asn Val Tyr
 1               5

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic
      humanized HC-08 CDR2 amino acid sequence

<400> SEQUENCE: 164

Tyr Ile Asp Pro Tyr Asn Gly Ile Thr Ile Tyr Asp Gln Asn Leu Lys
 1               5                  10                  15

Gly

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      humanized HC-08 CDR3 amino acid sequence

<400> SEQUENCE: 165

Asp Val Thr Thr Ala Leu Asp Phe
 1               5
```

<210> SEQ ID NO 166
<211> LENGTH: 107
<212> TYPE: PRT
<213> ORGANISM: Homo sapiens

<400> SEQUENCE: 166

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 167
<211> LENGTH: 332
<212> TYPE: PRT
<213> ORGANISM: Homo sapiens

<400> SEQUENCE: 167

```
Glu Phe Ala Ser Thr Lys Gly Pro Ser Val Phe Pro Leu Ala Pro Ser
  1               5                  10                  15

Ser Lys Ser Thr Ser Gly Gly Thr Ala Ala Leu Gly Cys Leu Val Lys
             20                  25                  30

Asp Tyr Phe Pro Glu Pro Val Thr Val Ser Trp Asn Ser Gly Ala Leu
         35                  40                  45

Thr Ser Gly Val His Thr Phe Pro Ala Val Leu Gln Ser Ser Gly Leu
     50                  55                  60

Tyr Ser Leu Ser Ser Val Val Thr Val Pro Ser Ser Ser Leu Gly Thr
 65                  70                  75                  80

Gln Thr Tyr Ile Cys Asn Val Asn His Lys Pro Ser Asn Thr Lys Val
                 85                  90                  95

Asp Lys Lys Val Glu Pro Lys Ser Cys Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
```

```
                        225                 230                 235                 240
Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 168
<211> LENGTH: 107
<212> TYPE: PRT
<213> ORGANISM: Homo sapiens

<400> SEQUENCE: 168

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 169
<211> LENGTH: 329
<212> TYPE: PRT
<213> ORGANISM: Homo sapiens

<400> SEQUENCE: 169

Glu Phe Ala Ser Thr Lys Gly Pro Ser Val Phe Pro Leu Ala Pro Cys
1               5                   10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125
```

```
Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325

<210> SEQ ID NO 170
<211> LENGTH: 11
<212> TYPE: PRT
<213> ORGANISM: Murine sp.

<400> SEQUENCE: 170

Leu Ala Ser Gln Thr Ile Asp Thr Trp Leu Ala
1               5                   10
```